(12) United States Patent
Goodman et al.

(10) Patent No.: US 11,998,197 B2
(45) Date of Patent: Jun. 4, 2024

(54) DEVICES FOR INSTRUMENT USE RECORDING, DEVICES FOR RECORDING INSTRUMENT REPROCESSING EVENTS, AND RELATED SYSTEMS AND METHODS

(71) Applicant: INTUITIVE SURGICAL OPERATIONS, INC., Sunnyvale, CA (US)

(72) Inventors: Jack Goodman, Ann Arbor, MI (US); Wesley Chung Joe, Fremont, CA (US); Tyler J. Morrissette, Niantic, CT (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 0 days.

(21) Appl. No.: 17/916,139

(22) PCT Filed: Apr. 1, 2021

(86) PCT No.: PCT/US2021/025372
§ 371 (c)(1),
(2) Date: Sep. 30, 2022

(87) PCT Pub. No.: WO2021/202869
PCT Pub. Date: Oct. 7, 2021

(65) Prior Publication Data
US 2023/0115444 A1 Apr. 13, 2023

Related U.S. Application Data

(60) Provisional application No. 63/025,563, filed on May 15, 2020, provisional application No. 63/003,986, (Continued)

(51) Int. Cl.
*A61B 17/072* (2006.01)
*A61B 17/12* (2006.01)
(Continued)

(52) U.S. Cl.
CPC ...... *A61B 17/072* (2013.01); *A61B 17/07207* (2013.01); *A61B 17/12* (2013.01);
(Continued)

(58) Field of Classification Search
CPC ............... A61B 17/068; A61B 17/072; A61B 17/07207; A61B 17/083; A61B 17/115;
(Continued)

(56) References Cited

U.S. PATENT DOCUMENTS 4,592,498 A 6/1986 Braun et al.
4,606,343 A 8/1986 Conta et al.
(Continued)

FOREIGN PATENT DOCUMENTS

CN 101011273 A 8/2007
CN 101321606 A 12/2008
(Continued)

OTHER PUBLICATIONS

International Search Report and Written Opinion for Application No. PCT/US2021/025372, dated Sep. 3, 2021, 20 pages.
(Continued)

*Primary Examiner* — Scott A Smith
(74) *Attorney, Agent, or Firm* — JONES ROBB, PLLC

(57) ABSTRACT

An instrument can include a shaft with a proximal end portion and a distal end portion, an end effector at the distal end portion of the shaft, and a transmission mechanism at the proximal end portion of the shaft. The transmission mechanism can include a driven input device engageable with an external drive mechanism. The instrument can include an indicator operably coupled to the driven input device and moveable through each of a plurality of consecutive positions, each of the plurality of consecutive positions being associated with a unique indicium of a non-zero number of available uses left of the instrument. In
(Continued)

response to the driven input device being driven, the indicator moves from a current position of the plurality of positions to a subsequent position of the plurality of positions. The instrument can also include a device configured to record occurrence of a change in an environmental condition to which the instrument is subjected.

20 Claims, 36 Drawing Sheets

Related U.S. Application Data filed on Apr. 2, 2020, provisional application No. 63/003,987, filed on Apr. 2, 2020.

(51) Int. Cl.
*A61B 17/128* (2006.01)
*A61B 34/30* (2016.01)
*A61B 17/00* (2006.01)
*A61B 17/068* (2006.01)
*A61B 17/10* (2006.01)
*A61B 90/10* (2016.01)

(52) U.S. Cl.
CPC .......... *A61B 17/1285* (2013.01); *A61B 34/30* (2016.02); *A61B 2017/00017* (2013.01); *A61B 17/068* (2013.01); *A61B 2017/07214* (2013.01); *A61B 17/105* (2013.01); *A61B 17/128* (2013.01); *A61B 90/10* (2016.02)

(58) Field of Classification Search
CPC ... A61B 17/105; A61B 17/12; A61B 17/1222; A61B 17/128; A61B 17/1285; A61B 2017/00017; A61B 2017/07214; A61B 34/30; A61B 90/10
USPC .............. 227/19, 175.1, 176.1, 175.2, 180.1; 606/139, 219
See application file for complete search history.

(56) References Cited

U.S. PATENT DOCUMENTS

| | | | |
|---|---|---|---|
| 4,619,391 A | 10/1986 | Sharkany et al. | |
| 4,951,860 A | 8/1990 | Peters et al. | |
| 5,313,935 A | 5/1994 | Kortenbach et al. | |
| 5,359,993 A | 11/1994 | Slater et al. | |
| 5,397,046 A | 3/1995 | Savage et al. | |
| 5,397,323 A | 3/1995 | Taylor et al. | |
| 5,630,431 A | 5/1997 | Taylor | |
| 5,766,126 A | 6/1998 | Anderson | |
| 5,991,355 A | 11/1999 | Dahlke | |
| 6,331,181 B1 | 12/2001 | Tierney et al. | |
| 6,468,265 B1 | 10/2002 | Evans et al. | |
| 6,601,748 B1 | 8/2003 | Fung et al. | |
| 7,477,927 B2 | 1/2009 | Stoianovici et al. | |
| 7,835,823 B2 | 11/2010 | Sillman et al. | |
| 8,241,271 B2 | 8/2012 | Millman et al. | |
| 8,852,208 B2 | 10/2014 | Gomez et al. | |
| 8,939,894 B2 | 1/2015 | Morrissette et al. | |
| 9,283,043 B2 | 3/2016 | Tsao et al. | |
| 9,295,524 B2 | 3/2016 | Schena et al. | |
| 9,358,074 B2 | 6/2016 | Schena et al. | |
| 9,398,935 B2 | 7/2016 | Kim et al. | |
| 9,655,680 B2 | 5/2017 | Shim et al. | |
| 9,782,198 B2 | 10/2017 | Elhawary et al. | |
| 9,980,829 B2 | 5/2018 | Miles et al. | |
| 10,188,391 B2 | 1/2019 | Viola et al. | |
| 10,285,694 B2 | 5/2019 | Viola et al. | |
| 10,470,829 B2 | 11/2019 | Alden et al. | |
| 10,758,234 B2* | 9/2020 | Malkowski | A61B 17/083 |
| 11,344,378 B2 | 5/2022 | Alden et al. | |
| 11,399,846 B2* | 8/2022 | Williams | A61B 17/1285 |
| 11,510,682 B2* | 11/2022 | Zergiebel | A61B 17/1222 |
| 11,583,291 B2* | 2/2023 | Baril | A61B 17/1285 |
| 2005/0043718 A1 | 2/2005 | Madhani et al. | |
| 2007/0151389 A1 | 7/2007 | Prisco et al. | |
| 2008/0135600 A1 | 6/2008 | Hiranuma et al. | |
| 2008/0262654 A1 | 10/2008 | Omori et al. | |
| 2009/0071554 A1 | 3/2009 | Beckman et al. | |
| 2009/0099520 A1 | 4/2009 | Millman et al. | |
| 2010/0193569 A1 | 8/2010 | Yates et al. | |
| 2011/0137323 A1 | 6/2011 | Malkowski et al. | |
| 2012/0143211 A1 | 6/2012 | Kishi | |
| 2013/0123798 A1* | 5/2013 | Tsao | A61B 90/11 606/130 |
| 2013/0253480 A1 | 9/2013 | Kimball et al. | |
| 2014/0194699 A1 | 7/2014 | Roh et al. | |
| 2015/0338728 A1 | 11/2015 | Amron | |
| 2016/0354166 A1 | 12/2016 | Popovic et al. | |
| 2016/0361048 A1* | 12/2016 | Alden | A61B 34/30 |
| 2017/0007335 A1 | 1/2017 | Popovic et al. | |
| 2017/0165847 A1 | 6/2017 | Popovic et al. | |
| 2019/0029707 A1 | 1/2019 | Asher et al. | |
| 2020/0078107 A1* | 3/2020 | Alden | A61B 34/30 |

FOREIGN PATENT DOCUMENTS

| | | |
|---|---|---|
| CN | 201281819 Y | 7/2009 |
| EP | 1790294 A1 | 5/2007 |
| EP | 2484304 A2 | 8/2012 |
| EP | 2659847 A1 | 11/2013 |
| JP | H08248838 A | 9/1996 |
| JP | 2006081687 A | 3/2006 |
| JP | 2006292805 A | 10/2006 |
| WO | WO-2008067143 A2 | 6/2008 |
| WO | WO-2009039058 A1 | 3/2009 |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
International Preliminary Report on Patentability for Application No. PCT/US2021/025372 dated Oct. 13, 2022, 12 pages.

* cited by examiner

DEVICES FOR INSTRUMENT USE RECORDING, DEVICES FOR RECORDING INSTRUMENT REPROCESSING EVENTS, AND RELATED SYSTEMS AND METHODS

This application is a U.S. national stage application under 35 U.S.C. § 371(c) of International PCT Application No. PCT/US2021/025372, filed Apr. 1, 2021, which claims the benefit of priority to U.S. Provisional Application No. 63/003,986, filed Apr. 2, 2020; U.S. Provisional Application No. 63/003,987, filed Apr. 2, 2020; and U.S. Provisional Application No. 63/025,563 filed May 15, 2020, each of which is incorporated by reference herein in its entirety.

TECHNICAL FIELD

Aspects of the present disclosure relate to devices, systems, and methods for recording a number of times an instrument is used and for conveying such use information to an individual and/or to a control system controlling use of the instruments. Further aspects of the present disclosure relate to recording occurrences of a medical instrument being subjected to one or more environmental conditions associated with a reprocessing procedure or other event for which recording an occurrence is desirable. Related devices, systems, and methods also are disclosed.

INTRODUCTION

Various instruments can be used to perform procedures such as surgical procedures, other medical procedures, or non-medical procedures. For example, medical instruments can be used with manipulators of teleoperated computer-assisted surgical systems. Other surgical instruments can include hand-held, manually operated instruments. Industrial instruments can similarly include instruments used with computer-assisted systems or manually operated systems. In many cases, such instruments have a predetermined lifespan such that use of the instrument may be prohibited or not recommended once the predetermined lifespan has expired, regardless of whether the instrument is still operational. Such a predetermined lifespan may be indicated by various factors, such as the susceptibility of components of the instrument to wear or other degradation, design limits related to fatigue life, ability of the instrument to withstand repeated cleaning and/or sterilization processes, or other factors, including regulatory requirements.

Uses of such instruments may be tracked manually, such as by keeping a manual record based on an instrument identification number. Further, for instruments that electronically couple with a system such as a teleoperated computer-assisted manipulator system, such uses can be tracked electronically, for example relying on instrument identification data stored at the instrument, and the number of uses can be conveyed through an electronic display associated with the manipulator system. However, the latter type of approach does not convey use information when the instrument is disconnected from the manipulator system, and the former is prone to error and also may pose challenges to access the manually-kept record.

In addition, in many cases, it is desirable to subject instruments after use to one or more types of cleaning processes, such as, for example, washing and/or sterilizing, to ensure sufficient cleanliness and/or sterility of the instrument prior to another use of the instrument. As used herein, the term "reprocessing" is intended to encompass any of the processes, or combinations thereof, used to prepare an instrument for a subsequent use. Reprocessing can include, but is not limited to, any one or more of washing, thermal disinfection, ultrasonic cleaning, autoclaving, and sterilizing.

Because of various factors, it may be desirable, and in some cases required by regulation, to limit the number of times an instrument can be reprocessed and subsequently used. Thus, a need exists to track the number of times an instrument has been subjected to reprocessing. Because challenges exist in tracking such information manually, and because such manual tracking can be time-intensive, it is desirable to automate such tracking of the reprocessing of instruments.

A need exists to track the number of times an instrument has been used in a manner that does not require additional effort for users or support staff, and that provides the usage information that is accessible from the instrument regardless of whether the instrument is connected to a manipulator system (or other powered system). In addition, there exists a need for reliable and robust devices, systems, and methods that keep an accurate record of reprocessing to which an instrument is subjected. Further, there exists a need for devices, systems, and methods that store and convey information to an individual and/or a control system regarding the number of times an instrument has been subjected to reprocessing. Moreover, there exists a need to record, store, and/or convey information regarding changes in environmental conditions to which an instrument is subjected, which changes can include any one or more of temperature excursions, pressure excursions, and subjection to various forms of energy (such as ultrasonic) to which an instrument is subjected.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one embodiment of the present disclosure, an instrument includes a shaft with a proximal end portion and a distal end portion, an end effector at the distal end portion of the shaft, and a transmission mechanism at the proximal end portion of the shaft. The transmission mechanism includes a driven input device engageable with an external drive mechanism. The instrument includes an indicator operably coupled to the driven input device and moveable through each of a plurality of consecutive positions, each of the plurality of consecutive positions being associated with a unique indicium of a non-zero number of available uses left of the instrument. In response to the driven input device being driven, the indicator moves from a current position of the plurality of positions to a subsequent position of the plurality of positions.

In accordance with at least another embodiment of the present disclosure, a method of indicating a number of available uses of an instrument includes coupling an instrument with a manipulator system, operating a driven input device of the instrument by actuating a drive mechanism of the manipulator, and moving an indicator of the instrument from a current position of a plurality of positions to a subsequent position of the plurality of positions. The subsequent position of the indicator is associated with indicia indicating a fewer non-zero number of available uses than indicia associated with the current position.

In accordance with at least another embodiment of the present disclosure, a medical device comprises a first indicator moveable through a first plurality of positions and a second indicator movable through a second plurality of positions. Each position of the first plurality of positions is associated with a unique indicia of a number of available uses remaining on the instrument. Each position of the second plurality of positions is associated with an occurrence of a change in an environmental condition to which the instrument is subjected.

In accordance with at least another embodiment of the present disclosure, a device for recording occurrence of a change in environmental conditions to which a medical instrument is subjected can include a state-change element transitionable between a first state and a second state in response to a change, the amount of which may be predetermined, in the environmental conditions. The device can include a counter mechanism operably coupled to the state-change element. The counter mechanism can be incrementally movable in response to transition of the state-change element from the first state to the second state. A user-accessible storage device can be operably coupled to the counter mechanism, and the user-accessible storage device can be configured to store and provide information representing a number of transitions of the state-change element.

In accordance with at least another embodiment of the present disclosure, a device for recording occurrence of a change of environmental conditions to which a medical instrument is subjected comprises an electronic non-volatile memory and a voltage source in a circuit with the memory. The memory is operably coupled to the voltage source such that on the condition the device is exposed to the change in environmental conditions, the voltage source applies a voltage to the memory.

In accordance with at least another embodiment of the present disclosure, a device for recording occurrence of a change in an environmental condition to which a medical instrument is subjected includes a state-change element transitionable between a first state and a second state in response to a predetermined change in the environmental condition. A counter mechanism is operably coupled to the state-change element, and the counter mechanism is incrementally movable in response to transition of the state-change element from the first state to the second state. A visual indicator is operably coupled to the counter mechanism, and the visual indicator is configured to display information representing a number of transitions of the state-change element. An indicator flag is configured to obscure view of the visual indicator on the condition that the visual indicator reaches a predetermined value of the information representing the number of transitions of the state-change element.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more embodiments of the present teachings and together with the description explain certain principles and operation. In the drawings.

DETAILED DESCRIPTION

Figure 1:
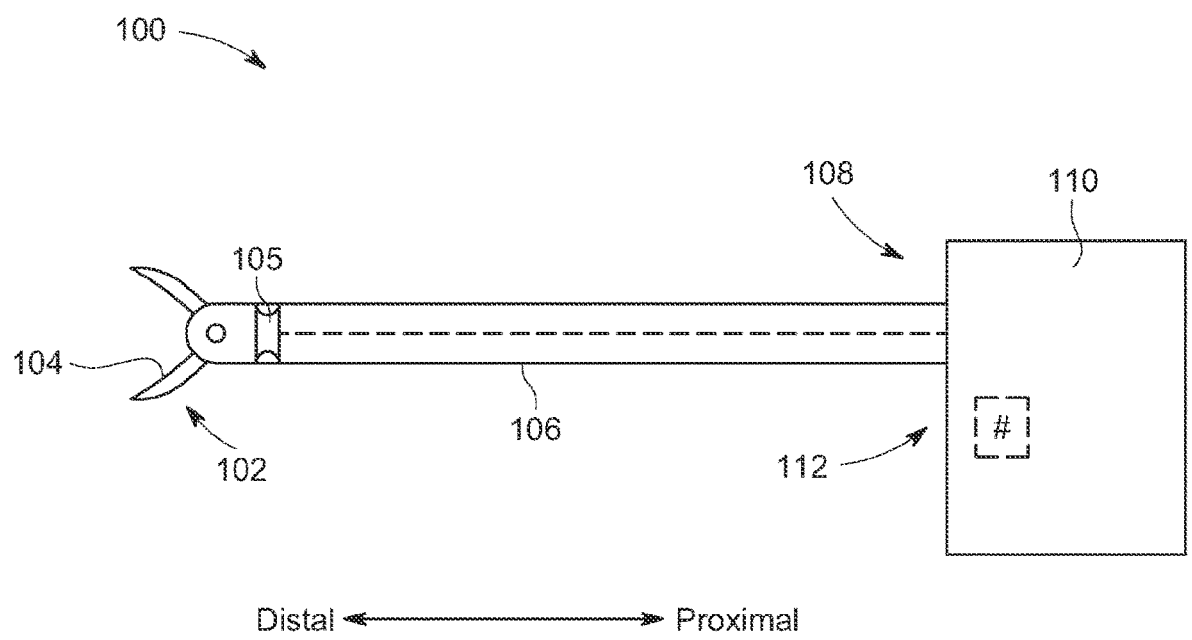
FIG. 1 is a schematic side view of an instrument comprising a device for recording use of the instrument according to an exemplary embodiment of the present disclosure.

The present disclosure provides various devices for recording uses of an instrument and for conveying such use information, and related systems, and methods. Such recording devices can be included with, or integrated with, a tool such as a surgical or industrial instrument. Recording devices according to the present disclosure can operate based on a mechanical input to the recording device that occurs when the instrument is coupled with a manipulator system, such as a manipulator system that operates at least in part with computer assistance or a manually operated manipulator system.

The recording devices of various exemplary embodiments can include various components configured to be operably coupled with a drive mechanism of the manipulating system. The drive mechanism can be configured to drive the components with a specified input based on, for example, an initial connection to a manipulating system, use of the instrument with the manipulating system for a specified time period, use of the instrument for a specified series of actions or number of actions, or other specific criterion chosen to represent a use of the instrument. Examples of various criteria that can be used to determine when a use should be counted are provided in U.S. Pat. No. 7,835,823 (filed Nov. 6, 2006), and U.S. Patent App. Pub. No. US 2016/0361048 A1 (filed Mar. 17, 2015), the entire contents of each of which are incorporated by reference herein.

The recording devices can be configured to convey information, such as for example by way of indicia exhibiting the number of remaining uses of a plurality of available (i.e., non-zero) remaining uses of the instrument. Additionally or alternatively, the indicia can exhibit the number of times the instrument has been used. Other recording devices according to the present disclosure can be configured to display a remaining available fraction, or a used fraction, of a total life of the instrument. Such devices can be implemented with a gauge-type approach, such as similar to a vehicle gas gauge, or other types of analog and/or digital indicators. The indicia can include, without limitation, visual indicia, tactile indicia, auditory indicia, or any indicia that provide a form of feedback to a user.

The indicia can be provided on an indicator of the instrument that is accessible regardless of whether the instrument is connected to any manipulating system or other powered system to which the instrument is coupled when in use. In this way, the indicia can represent a mechanical form of "non-volatile" memory. The indicia can be positioned and designed to be easily recognized and understood by a user of the instrument or personnel tasked with transporting, storing, tracking, or otherwise handling the instrument. For example, the indicia can be visual indicia configured to be viewable through an aperture (which may be covered or uncovered) in a housing of the instrument.

The indicia can be in the form of an integer number of uses remaining, an integer number of uses the instrument has undergone, a fractional indication of usable life remaining or usable life already used, or another type of indicator. Other types of indicators can include gauge-type indicators, indicators based on color coding, or other indication schemes, such as using tactile, auditory, or other feedback. Further, the indicators associated with the indicia can include features that maintain the indicia in a given configuration upon removal of the instrument from the manipulator, and such features can maintain the indicator in the given configuration until a subsequent use of the instrument causes the recording device to advance the indicator to another configuration in response to use of the instrument.

Regardless of the particular form of the indicia, embodiments of the present disclosure can provide information regarding how many out of multiple total uses of a predetermined lifespan of an instrument remain. Such information can be useful to provide additional information about the life left of an instrument to assist in planning for procedures in which an instrument is to be used, which in certain cases may require multiple uses of an instrument. Accordingly, knowing that an instrument has enough uses or not can be helpful to personnel when choosing an instrument for a particular procedure.

In addition to information regarding the number of uses to which an instrument has been subjected, it can be desirable to provide information regarding a number of reprocessing procedures to which an instrument has been subjected. Thus, in addition to recording devices that record a number of uses of the instrument, the present disclosure provides devices for recording one or more events, such as a change in environmental conditions occurring during a reprocessing procedure, to which the instrument is subjected. Such reprocessing procedures can involve application of heat and result in a temperature excursion, application of ultrasonic or other mechanical energy, exposure to pressure cycles, or other conditions. In various embodiments, such reprocessing recording devices can operate based on exposure to temperature changes, exposure to pressure changes, and/or application of various forms of energy (e.g., ultrasonic energy) to which an instrument may be subjected, so as to be able to record a number of instances the instrument has been so subjected.

Such reprocessing recording devices can be mechanical devices made of relatively few moving parts. Moreover, in some embodiments, the reprocessing recording devices do not require a constant electrical power source to operate. Further, reprocessing recording devices according to various exemplary embodiments can operate reliably and independently within relatively extreme environments, such as in one or more of wet or vaporous environments, environments that have chemicals, environments with relatively high or relatively low temperatures, including washing, sterilization and/or autoclave temperatures for example, environments having high humidity levels, environments at relatively high or low pressures, and environments subjected to various energy modes, such as, for example, in an ultrasonic washer environment, fluidic flushing, and/or mechanical agitation.

Provision of an instrument including both a use recording device and a reprocessing recording device according the present disclosure can ensure that the instrument can reliably provide to the user useful information regarding how many uses and reprocessing events to which the instrument has been subjected, and thus the ultimate fitness of the instrument for use.

Instrument Use Recording Devices, Systems, and Methods

Referring now to FIG. 1, a schematic side view of an instrument 100 according to an exemplary embodiment of the present disclosure is shown. The instrument 100 includes a distal end portion 102 which may include an end effector 104, which can include, without limitation, surgical tools such as shears, forceps, needles, electro-surgical tools, imaging or other sensing devices, suturing devices, or any other medical or non-medical equipment. A shaft 106 extends from the distal end portion 102 to a proximal end portion 108 of the instrument 100. The proximal end portion 108 can be or include a transmission mechanism 110 configured to be operably coupled with a surgical manipulator system, such as teleoperated surgical systems that operate at least in part with computer assistance, such as the DA VINCI® Surgical Systems commercialized by Intuitive Surgical, Inc., of Sunnyvale, California, or it can be manually controlled with manually operated (e.g., handheld) actuators (not shown). Optionally, the instrument 100 can include a wrist 105 coupling the end effector 104 to a distal end portion of the shaft 106 to provide one or more degrees of freedom of movement of the end effector 104 relative to the shaft 106.

The instrument 100 includes a device for recording use of the instrument, which can include an indicator 112 comprising indicia reflecting information concerning the number of uses of the instrument that have occurred over a predetermined lifespan, as will be described in further detail below a generic hashtag is shown in FIG. 1 to represent the indicia that may be displayed. The use recording device can be integrated into a housing of the instrument 100, as in the exemplary embodiment of FIG. 1. The use recording device can record and convey information, such as via visual indicia, concerning the number of uses of a predetermined lifespan of an instrument (e.g., one or both of the number of uses out of a predetermined number of uses or the remaining uses available) for the instrument 100. Such recording may be based on actuation of an input device of the instrument by a drive device, such as the drive device of a manipulator to which the instrument and thereby the input device is operably coupled. An input device of the instrument actuated by a drive device can be referred to herein as a driven input device.

Figure 2:
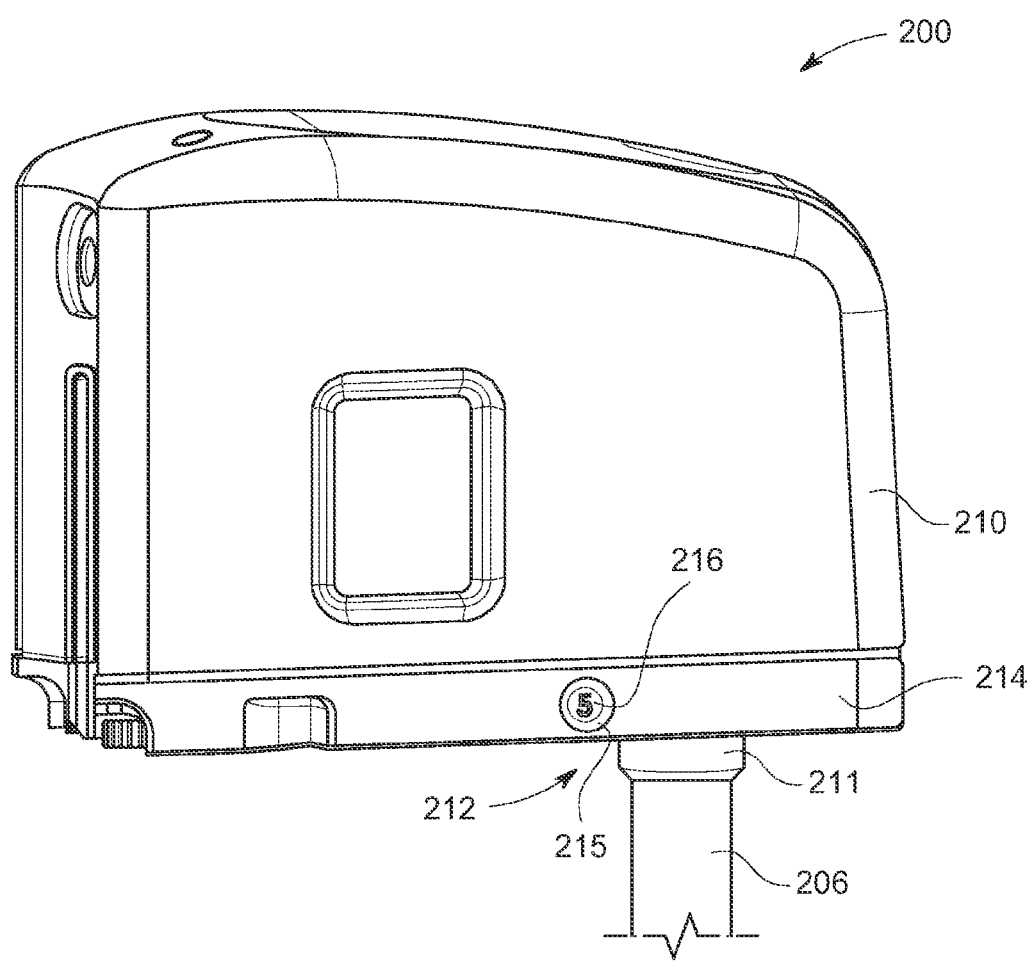
FIG. 2 is a side perspective view of a portion of an instrument comprising a device for recording use of the instrument according to another exemplary embodiment of the present disclosure.

Referring now to FIG. 2, a transmission mechanism portion of an instrument (the shaft and distal end portion not shown for simplicity in FIG. 2) comprising a use recording device according to an exemplary embodiment of the present disclosure is shown. FIG. 2 shows a perspective view primarily showing a side of the transmission mechanism 210 of an instrument 200 with an indicator 212 visible on the side of the instrument 200. A shaft 206 of the instrument 200 generally extends from the collar 211 at the bottom of the transmission mechanism 210. The indicator 212 is configured to be viewable from an exterior of the instrument 200. For example, a housing portion of the transmission mechanism 210 can include an aperture, transparent window, or other feature that reveals the indicator such that the indicator is viewable from the exterior of the instrument 200. The indicator can include, as discussed above, one or more of integer numbers, fractional indicators, gauge-type indicators, a color-coded indicator scheme, or other indicators. Additionally, non-visual types of indicators are contemplated, such as tactile indicators (e.g., braille integers in addition to or in place of the visual integers, or other tactile indicators), auditory indicators, or indicators utilizing other types of feedback.

In the device shown in FIG. 2, a housing portion 214 of the transmission mechanism 210 (which, in FIG. 2, is a base of the instrument) includes an aperture 215 through which a visual indicia 216 is shown. The indicia 216 visible through the aperture 215 is an integer number representing a number of remaining available (non-zero) uses of the instrument 200. In addition to, or in place of the indicia shown in FIG. 2, other types of indicia can be exposed through the aperture 215, such as color-coded indicators, gauge indicators such as a tapered bar graph, tactile indicators, etc. as discussed herein. Indicia as used herein refers to one or more indicium that alone or collectively indicate or convey information.

As discussed above, the indicator can be operably coupled with an external drive mechanism, such as a drive mechanism of a manipulator to which the instrument 200 is attached. Manipulators can include, for example, manipulator systems such as those discussed below in connection with FIGS. 13 and 14, manually operated instruments, or other manipulator systems. The indicator can have a plurality of unique positions, each representing a number of remaining available uses of the instrument. A change in the position of the indicator results in a different indicia being exposed through the aperture 215. Such a change in position can be accomplished by actuation of the drive mechanism of the manipulator system to which the instrument is coupled, such as a manual manipulator system or a teleoperated manipulator system that operates at least in part with computer assistance.

Figure 3:
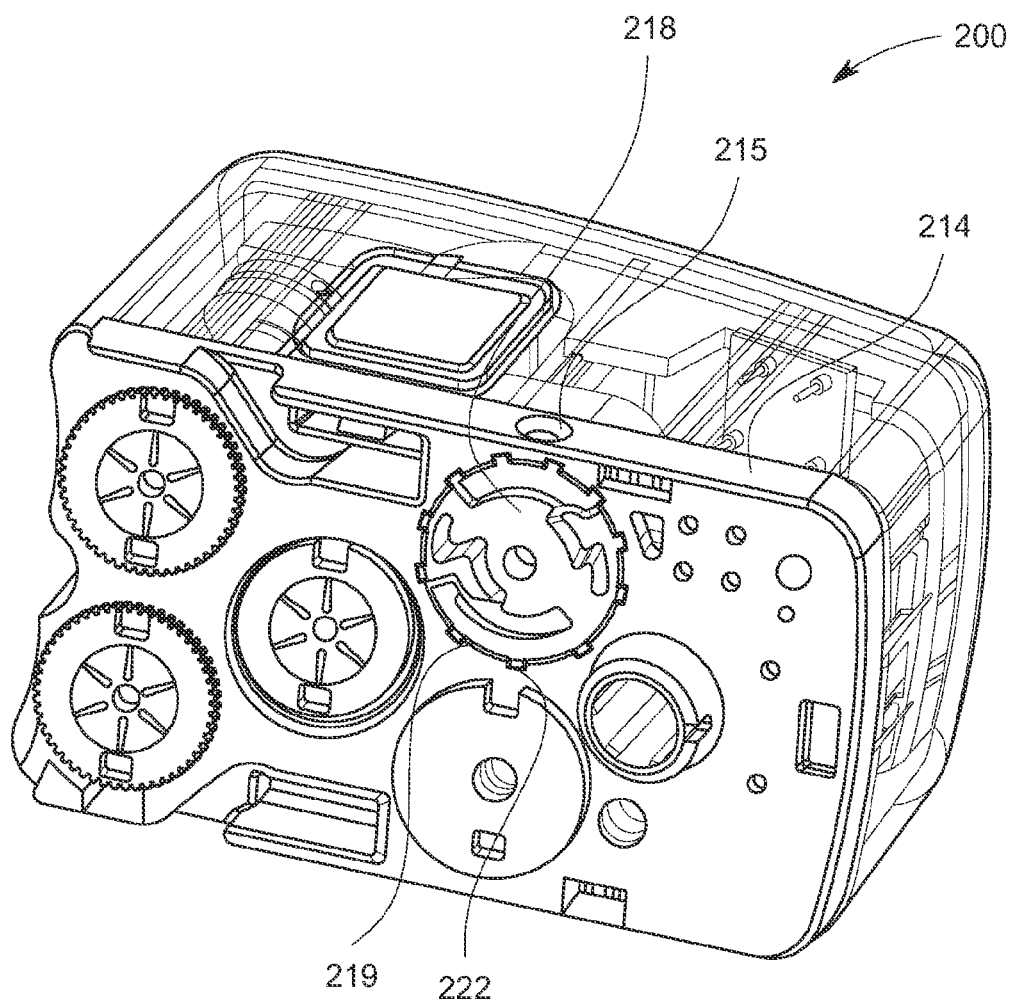
FIG. 3 is a bottom perspective view of the portion of the instrument of FIG. 2.

FIG. 3 shows the transmission mechanism 210 of the instrument 200 of FIG. 2 in a perspective view primarily showing the drive interface side of the instrument 200. The drive interface comprises a plurality of input discs configured to be respectively coupled to drive output members (e.g., of a manipulator system in the case of a teleoperated computer-assisted surgical system). The plurality of input discs include a rotatable disc 218 used for the indicator. The rotatable disc 218 is engageable with a drive mechanism of a manipulator system, as will be discussed in greater detail below. The rotatable disc 218 is positioned within a cavity 219 of the housing portion 214, and a portion of an outer lateral sidewall 220 (FIG. 4) of the rotatable disc 218 is viewable through the aperture 215.

Figure 4:
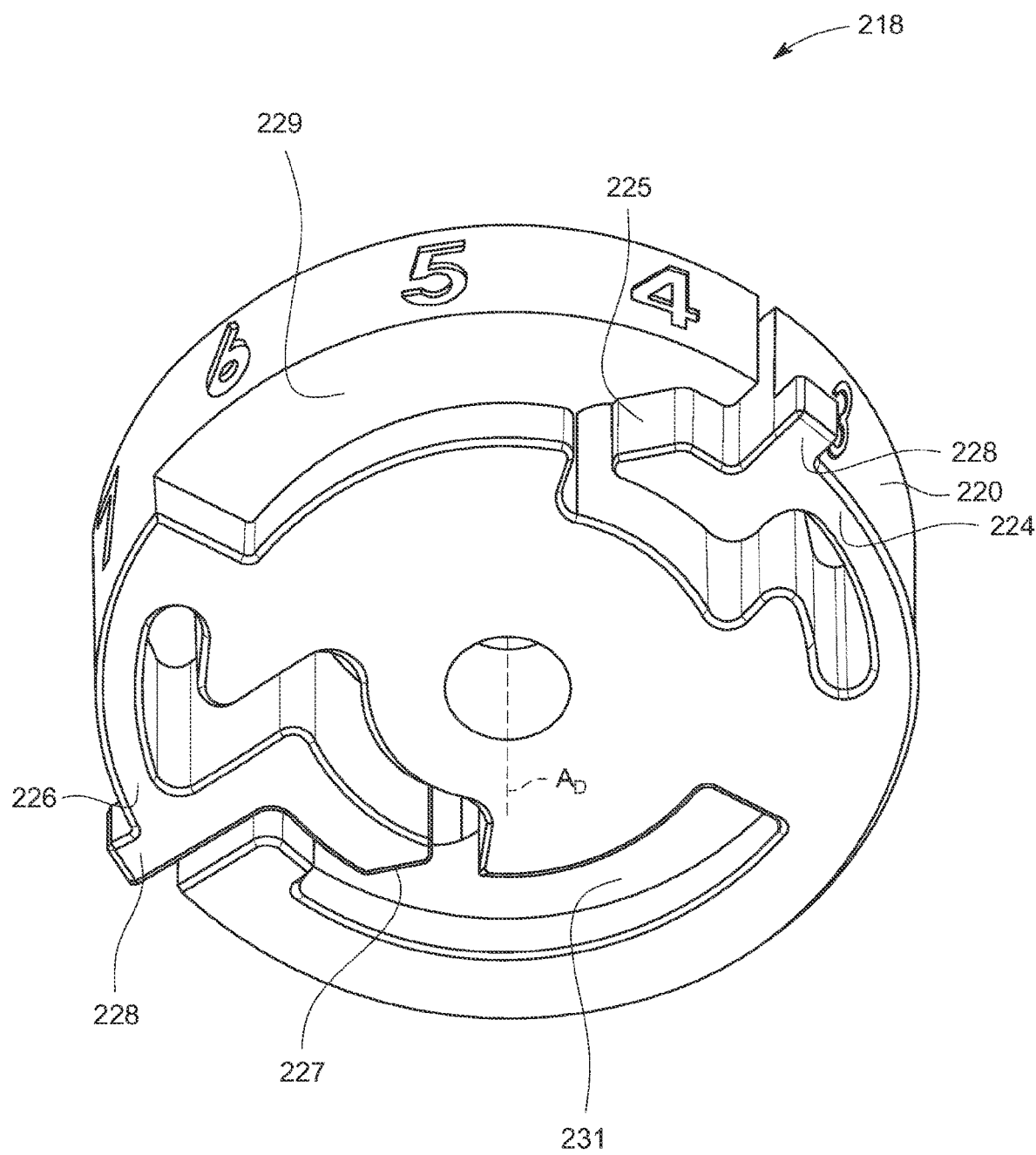
FIG. 4 is a perspective view of a rotatable disc of the device for recording use of the instrument according to the embodiment of FIG. 2.

Referring now to FIG. 4, the rotatable disc 218 is shown in an exploded view removed from the cavity 219 (FIG. 3) of the housing portion 214 (FIG. 3) of the instrument 200. As illustrated in FIG. 4, the rotatable disc 218 includes visual indicia in the form of integer numbers displayed around an outer lateral sidewall 220 of the rotatable disc 218. The integer numbers may be printed, molded, embossed, or otherwise provided on the outer lateral sidewall 220 of the rotatable disc 218. As discussed above, other types of indicia may be provided in place of, or in addition to, the integer numbers, such as a tapered bar graph indicator or other type of fractional indicator that shows a proportion of the life of the tool remaining. Those of ordinary skill in the art will appreciate a variety of other indicia, e.g., the alternative approaches discussed above, can be used to convey remaining uses or approximate remaining uses of a predetermined lifespan of an instrument. The rotatable disc 218 can have a plurality of consecutive positions, with each position corresponding to a differing one of the indicia being visible from external the instrument that represents a non-zero number of available uses of the instrument remaining.

The use recording device can include various features configured to prevent inadvertent movement of its mechanical components when the transmission mechanism 210 of the instrument 200 is not coupled with the manipulating system, such as during storage, transport, or other handling of the instrument 200. Such features can include locking mechanisms that prevent inadvertent back driving or forward driving of the use recording device, which could lead to inadvertent and incorrect change in the information being conveyed by the indicator.

For example, in the device shown in FIGS. 2-4, the rotatable disc 218 and the housing portion 214 each can include features configured to prevent inadvertent rotation of the rotatable disc 218 when the instrument 200 is not coupled with the manipulating system. Referring again to FIG. 3, the cavity 219 of the housing portion 214 includes a plurality of notches 222 formed on an inside lateral wall of the cavity 219, generally so as to surround the rotatable disc 218. The rotatable disc 218 includes features configured to engage the plurality of notches 222 of the cavity 219. As best viewed in FIG. 4, the rotatable disc 218 includes first and second flexural members 224 and 226, each with a radial extension 228 extending therefrom and configured to engage with the housing portion 214 within the notches 222 (FIG. 3) in the cavity 219 to prevent rotation of the rotatable disc 218, as discussed further below. The notches 222 and the radial extensions 228 can be arranged such that each position of the radial extensions 228 within a pair of notches 222 is associated with a different indicia (e.g., a different integer number, different bar graph height, etc.) being displayed through the aperture.

With continued reference to FIG. 4, the first and second flexural members 224 and 226 each include cam surfaces 225 and 227 inclined with respect to a radial direction. The cam surfaces 225 and 227 are located at respective free ends of the flexural members 224 and 226. The rotatable disc 218 also includes relieved portions 229, 231 adjacent the cam surfaces 225, 227 and extending circumferentially around a portion of the rotatable disc 218. In the device disclosed in connection with FIGS. 2-4, the relieved portions 229, 231 are offset relative to a rotational axis $A_D$ of the rotatable disc 218.

In the embodiment shown, the two flexural members 224, 226 are disposed generally diametrically opposite one another on the rotatable disc 218. Those having ordinary skill in the art would appreciate that one or more flexural members can be used without departing from the scope of the present disclosure.

Figure 5:
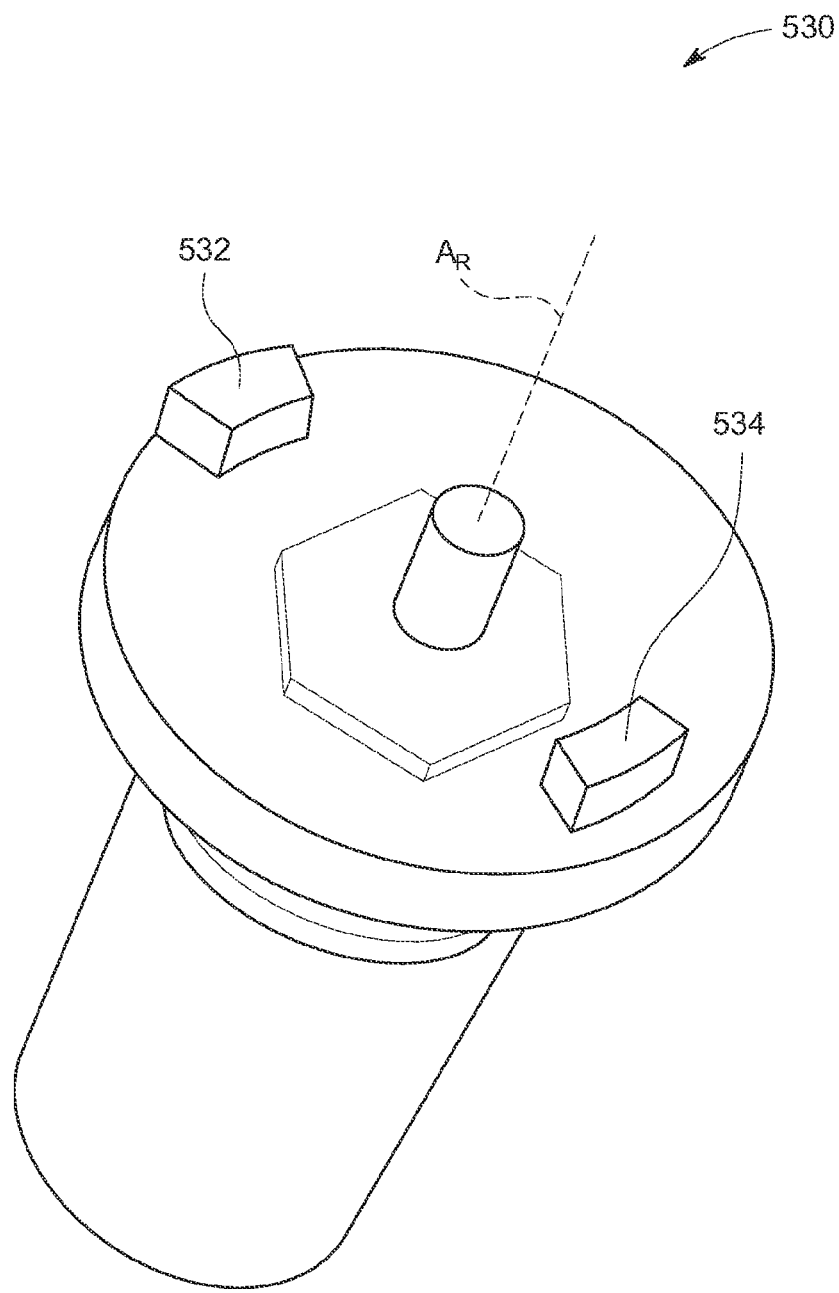
FIG. 5 is a perspective view of a drive mechanism for coupling to an instrument according to an exemplary embodiment of the present disclosure.

As discussed above, components of use recording devices of the present disclosure, such as the rotatable disc 218, can be configured to operably engage with external drive mechanisms, such as output drive mechanisms associated with manipulator systems with which instruments of the present disclosure are used. For example, the use recording devices of the present disclosure can be configured to engage with a rotatable output drive mechanism of a manipulator system. Referring now to FIG. 5, an output drive mechanism 530 of a manipulator system (such as the manipulator systems show in FIGS. 13 and 14 below) is shown in isolation. The drive mechanism 530 includes features configured to interact with the mechanical components of the use recording device. While the drive mechanism 530 of FIG. 5 is a drive disc, a person of ordinary skill in the art will appreciate that other configurations of drive mechanisms are possible within the scope of the disclosure.

The drive mechanism 530 includes one or more protrusions, such as two protrusions 532 and 534. The two protrusions are positioned at different circumferential and radial locations on the drive mechanism 530. For example, in the embodiment of FIG. 5, the protrusions 532 and 534 are located diametrically opposite one another relative to a rotational axis $A_R$ of the drive mechanism 530, and the protrusions 532 and 534 are also radially offset from one another. That is, each of the protrusions 532 and 534 are at different radial distances from the rotational axis $A_R$ of the drive mechanism 530.

Figure 6:
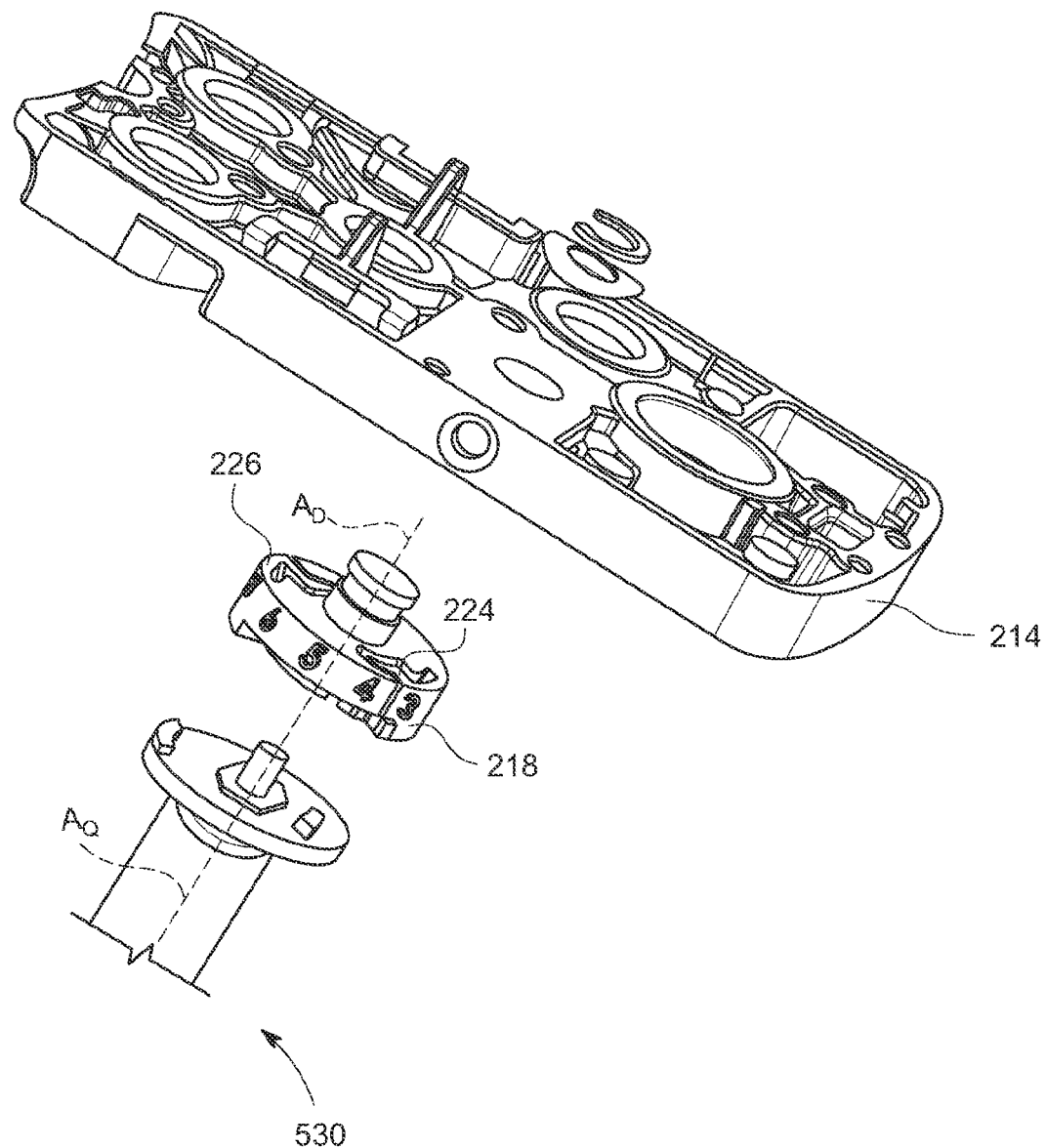
FIG. 6 is an exploded view of a base of an instrument, a rotatable disc of a device for recording use of the instrument, and a drive mechanism according to an embodiment of the present disclosure.

FIG. 6 shows an exploded view of the base of the housing portion 214 of the instrument 200 (FIG. 2), the rotatable disc 218 (FIG. 4), and the drive mechanism 530 (FIG. 5). When the instrument 200 is coupled with the manipulator (e.g., the drive interface of the transmission mechanism 210 is coupled with manipulators as discussed below in connection with FIGS. 13 and 14), the output drive mechanism 530 rotational axis $A_R$ is aligned with the rotational axis $A_D$ of the rotatable disc 218, as indicated by the broken connection line. As the instrument 200 is coupled with the manipulator, the protrusions 532 and 534 of the drive mechanism 530 are received within the relieved portions 229, 231 (FIG. 4) of the rotatable disc 218. Once the instrument and manipulator are coupled and ready for use or when use of the instrument and manipulator has begun, a control system (such as control system 1362 associated with system 1300 shown in FIG. 13 or control system 1462 shown in FIG. 14) operably coupled to the manipulator can evaluate, based on any of the criteria discussed above, whether a use should be decremented from the use recording device. As used in the discussion below, a life being "decremented" from the use recording device can include any and all of an integer displayed being decreased to show fewer remaining uses, increased to show a greater number of uses the instrument has undergone, an increase or decrease in a fractional-type display, or any other change in visual or other indicia displayed at the indicator of the use recording device that can provide an indication of the number of uses left for the instrument.

Figure 7A:
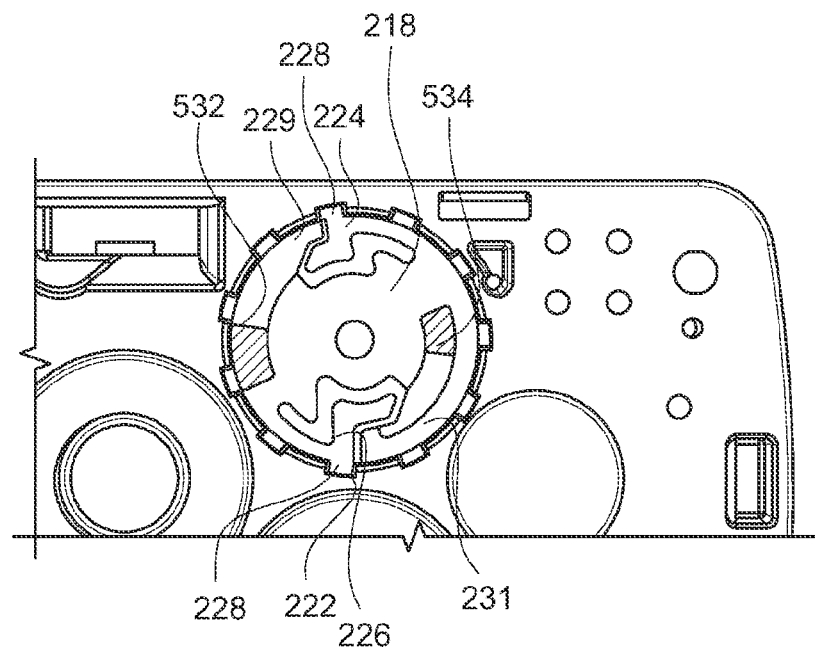
FIGS. 7A-7D show bottom views of the device of FIG. 3 with a rotatable disc of the device for recording use of the instrument in varying positions.

Operation of the use recording device when coupled with the manipulator is discussed in connection with FIGS. 7A-7D. Referring now to 7A, a bottom plan view of the device of FIG. 3 is illustrated, with the protrusions 532 and 534 of the drive mechanism 530 shown received within the relieved portions 229, 231 in an initial position representative of the relationship of the drive mechanism 530 (FIG. 6) and rotatable disc 218 when the instrument 200 is initially coupled with the manipulator system. As those having ordinary skill in the art are familiar with, the manipulator system can include self-indexing capability to place the drive mechanism 530 in the initial position relative to the rotatable disc 218 as shown in FIG. 7A. For example, the drive mechanism 530 can be spring-loaded, such that the drive mechanism 530 can be placed in contact with the rotatable disc 218 regardless of the relative rotational orientations of the components. Stated another way, the drive mechanism 530 and/or protrusions 532, 534 can be biased along the direction of rotational axis $A_R$ such that the protrusions 532, 534 do not have to be aligned with the relieved portions 229, 231 for the drive mechanism 530 to be coupled to the rotatable disc 218. In such exemplary embodiments, upon coupling, the manipulator can drive the drive mechanism 530 in the counterclockwise direction (relative to the view of FIG. 7A) until the biased protrusions reach and enter the relieved portions 229, 231. The drive mechanism 530 is driven further counterclockwise until the protrusions 532, 534 abut the end of the relieved portions 229, 231 rotationally opposite the cam surfaces 225, 227 and the associated flexural members 224, 226 due to engagement of the radial extensions 228 in notches 222. In this configuration, the drive mechanism 530 (not shown except for the protrusions 532, 534) is indexed at the initial position shown in FIG. 7A, and information about this initial position can be stored by, e.g., an electronic controller of the manipulator system.

In the state shown in FIG. 7A, at least a portion of the rotatable disc 218 is viewable through the aperture 215 (FIG. 2) to show the desired indicia of remaining predetermined lifespan. In a non-limiting embodiment, for example, the indicia are one integer number of the plurality of integer numbers provided on the rotatable disc 218 representing a unique indication of a specific number of available uses is shown through the aperture 215.

Figure 7B:
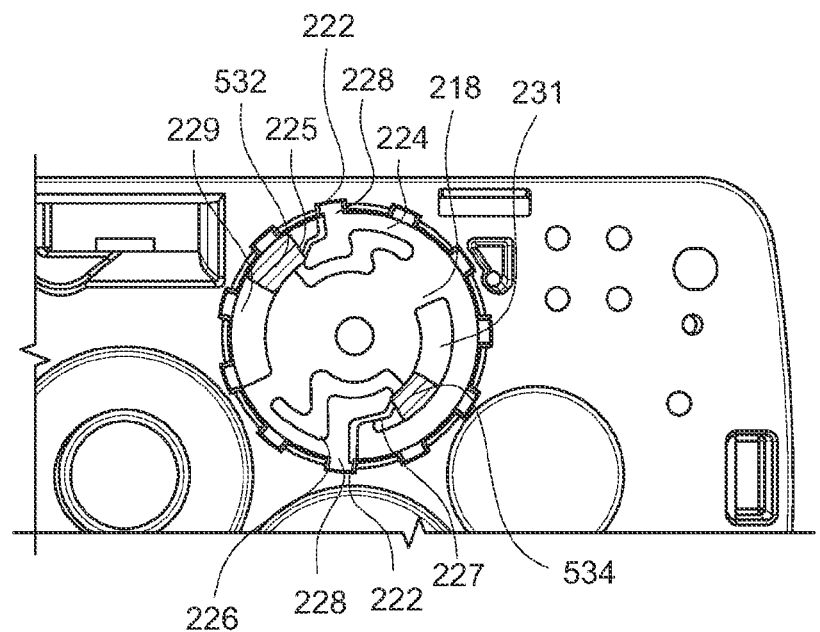
Figure 13:
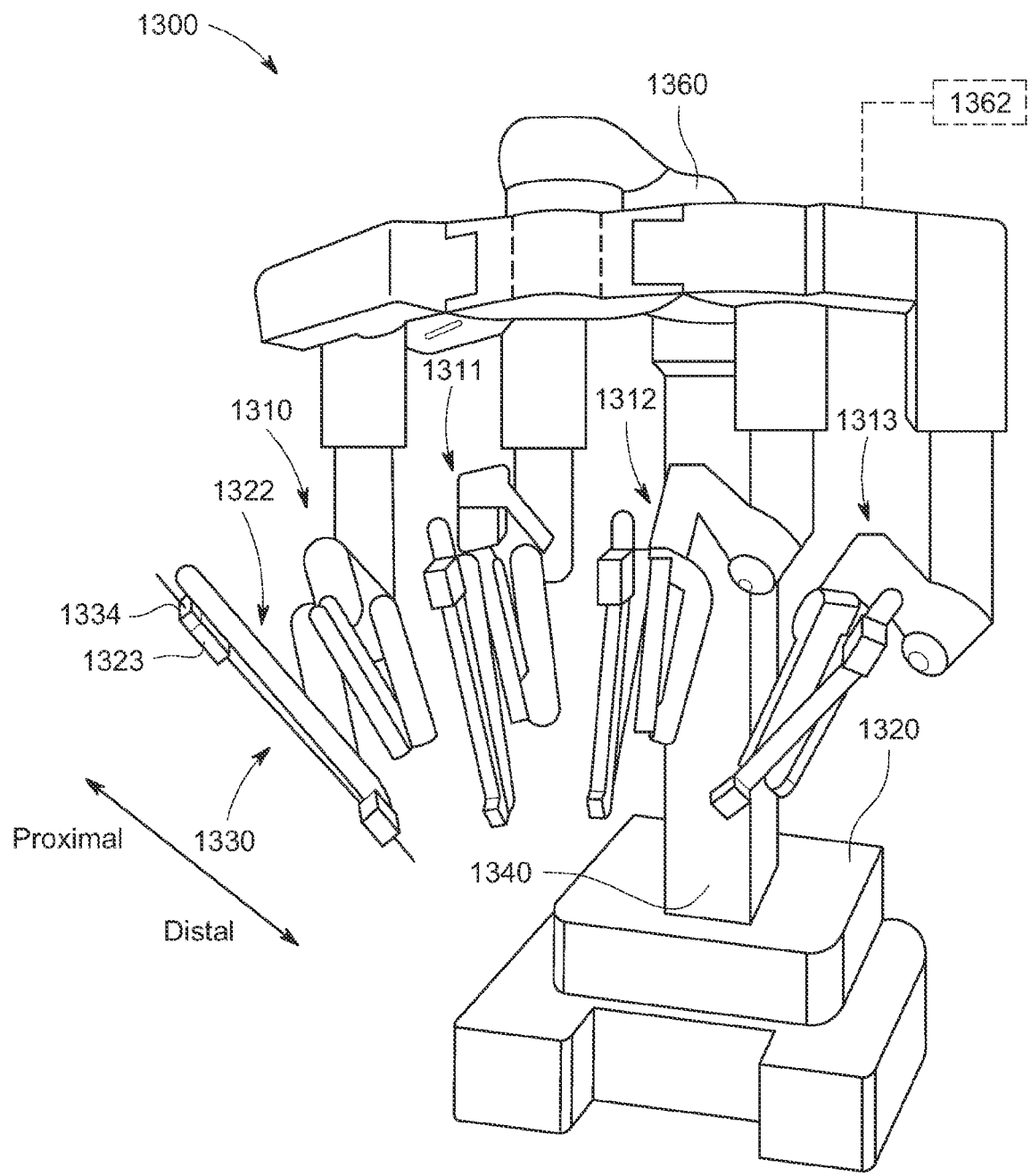
FIG. 13 is a perspective view of a manipulator system with one instrument installed according to an embodiment of the disclosure.
Figure 14:
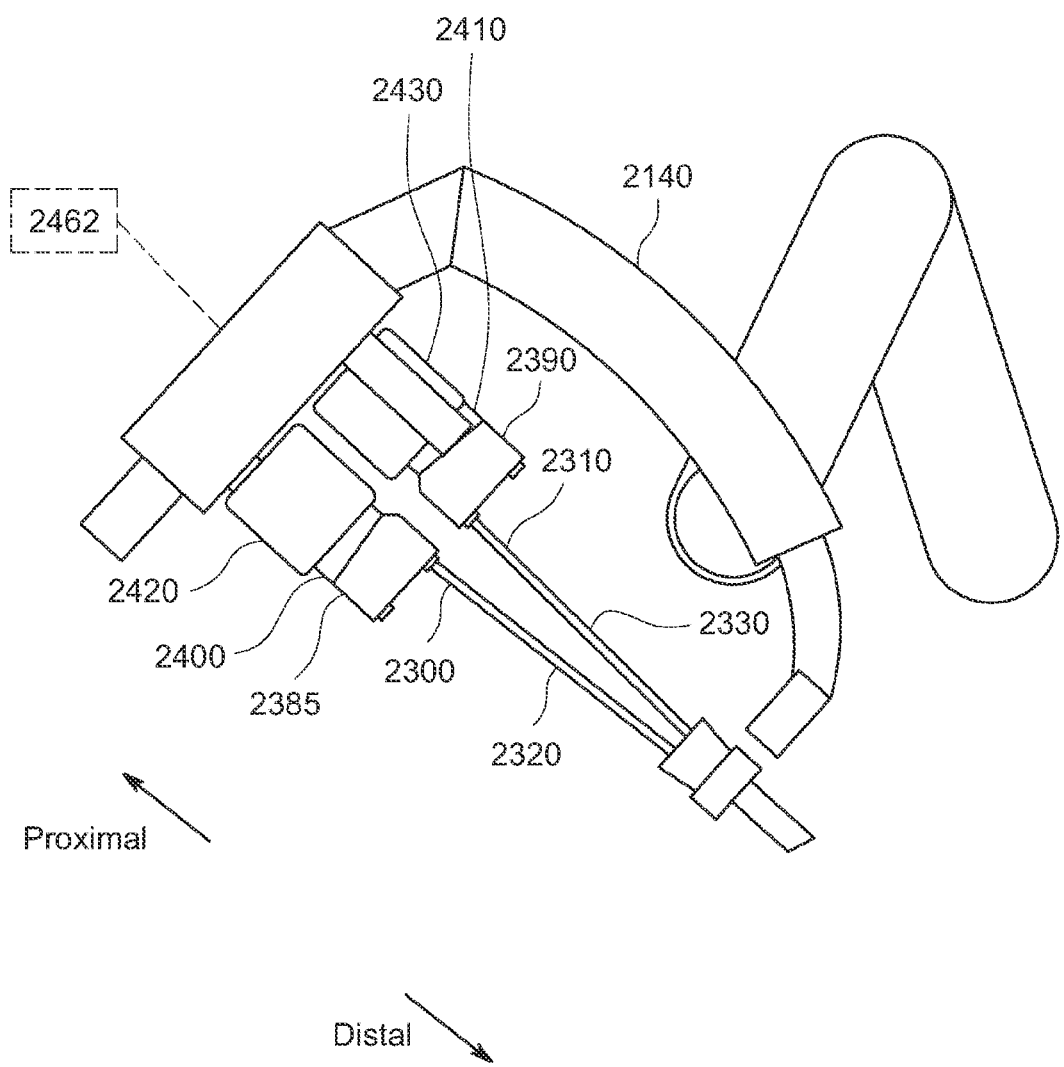
FIG. 14 is a schematic view of an embodiment of a manipulator arm of a manipulator system with two instruments in an installed position according to another embodiment of the present disclosure.

Referring to FIG. 7B, once the control system (such as control system 1362 associated with system 1300 shown in FIG. 13 or control system 1462 shown in FIG. 14) determines that a use should be decremented from the use recording device, the control system causes the drive mechanism 530 (FIG. 6) to be actuated, e.g., rotated in the clockwise direction as viewed in FIG. 7B, to advance the use the indicator via rotation of the rotatable disc 218. As the drive mechanism 530 rotates, the protrusion 532 contacts the cam surface 225 and the protrusion 534 contacts the cam surface 227. Contact between the protrusions 532 and 534 and the cam surfaces 225 and 227 and continued torque applied by the drive mechanism 530 causes the flexural members 224 and 226 to deflect radially inward, pulling the radial extensions 228 radially inward and out of the notches 222 of the cavity 219, thereby disengaging the flexural member 224 and 226 from the notches 222 and enabling rotation of the rotatable disc 218.

Figure 7C:
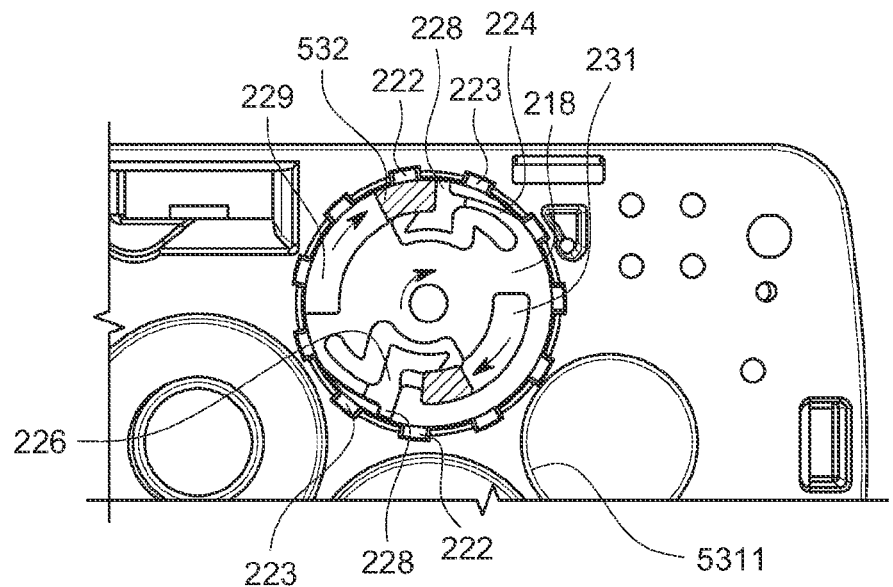
Figure 7D:
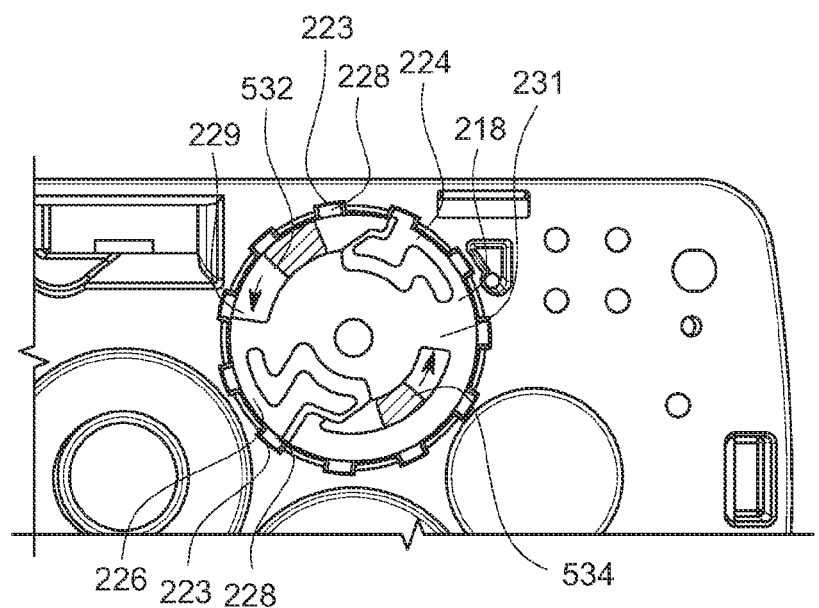

Referring to FIG. 7C, as the drive mechanism 530 (FIG. 6) continues to rotate in the clockwise direction, the rotatable disc 218 rotates with the drive mechanism 530 until the radial extensions 228 align with a set of notches 223 adjacent to the notches 222 in which the radial extensions 228 were previously located. The drive mechanism 530 stops clockwise rotation and rotates briefly counterclockwise so that the protrusions 532 and 534 disengage cam surfaces 225 and 227, thereby enabling the flexural members 224, 226 to return to an undeflected state and the radial extensions 228 to reenter notches 223, as shown in FIG. 7D.

Once the flexural members 224, 226 enter the adjacent set of notches 223, another integer number of the plurality of integer numbers is visible through the aperture 215 (FIG. 2). For example, according to one exemplary embodiment, if the number 5 was viewable through the aperture 215 in the position of the rotatable disc 218 shown in FIG. 7A, after the decrementing procedure of FIGS. 7B and 7C, the number 4 would then be visible through the aperture 215 in the position of FIG. 7D, representing a unique indication showing one fewer available uses than the position of the rotatable disc 218 in FIG. 7A.

The manipulator can be controlled via the control system (such as control system 1362 associated with system 1300 shown in FIG. 13 or control system 1462 shown in FIG. 14) to rotate the drive mechanism 530 only as far as necessary to move the rotatable disc 218 from one set of notches 222 to an adjacent set of notches 223, with such movement representing a decrement of a single available use. Additionally or alternatively, the manipulator can be programmed to decrement multiple uses by driving the rotatable disc 218 through multiple adjacent sets of notches 222 based on a length of use, type of use, or other factors. The number of notches 222 may be equal to the number of uses/decrements or may be different from the number of uses/decrements, depending on various factors such as the total number of uses envisioned, the diameter of the rotatable disc 218, and other considerations.

Once the drive mechanism 530 has decremented the use recording device 213, the drive mechanism 530 can remain stationary until the instrument 200 is decoupled from the manipulator. The rotatable disc is held in place by the radial extensions 228 within the notches 222 and thereby reliably displays the appropriate number, or fraction, or other desired indicia to provide information of remaining uses of a predetermined lifespan of the instrument 200, even while the instrument 200 is stored, transported, and otherwise handled until the next use.

Figure 8:
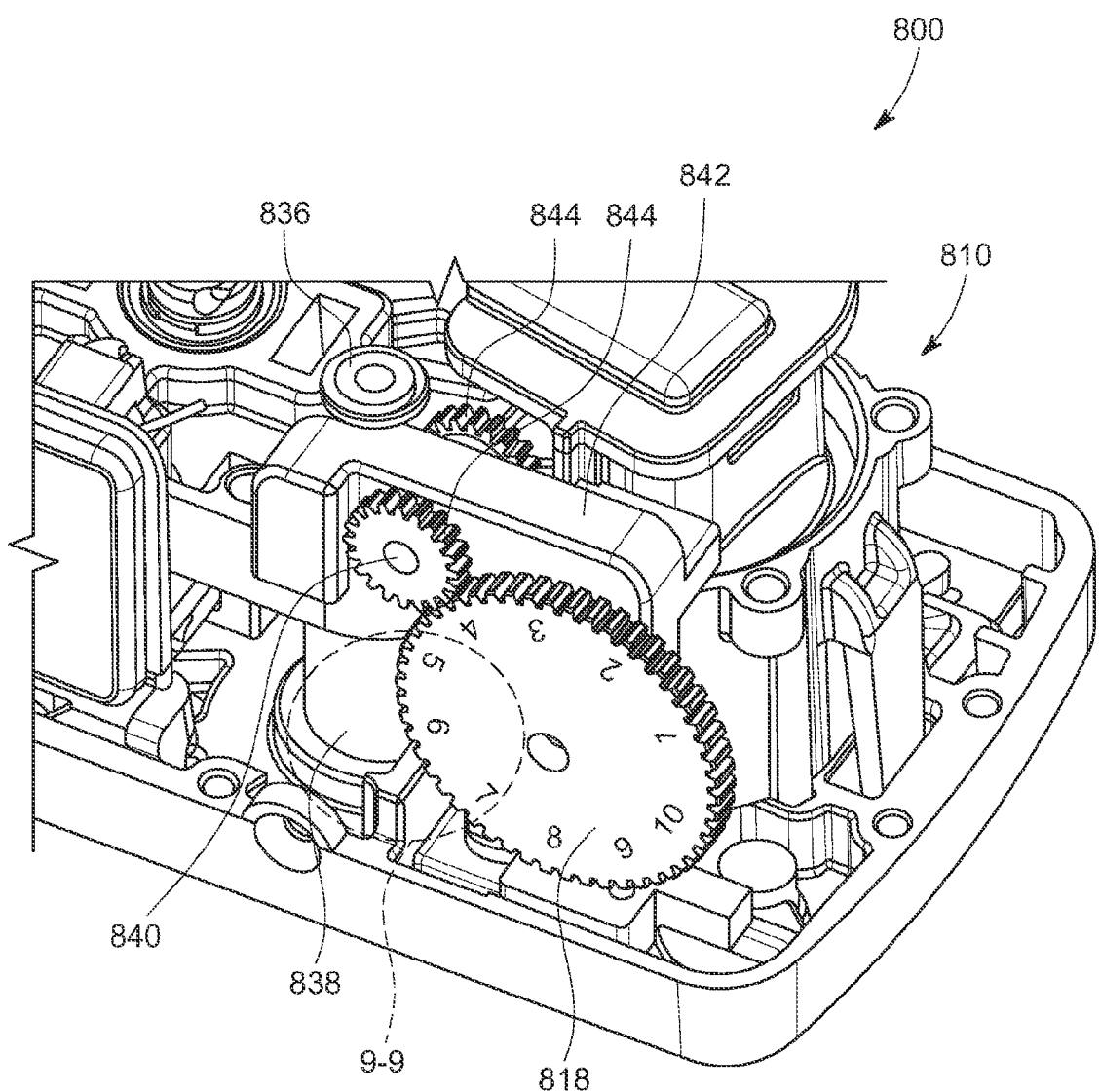
FIG. 8 is a partial perspective view of a portion of an instrument and device for recording use of the instrument according to another exemplary embodiment of the present disclosure, with a housing portion removed to reveal features of the device for recording use of the instrument.

Referring now to FIG. 8, another embodiment of a use recording device of an instrument according to the present disclosure is shown. In FIG. 8, a portion of a transmission mechanism 810 of an instrument is shown with the outer housing omitted to show internal components. In the embodiment of FIG. 8, the transmission mechanism 810 includes a use recording device that comprises a worm drive 836 that is directly connected to an input shaft 838. The input shaft 838 in turn can be coupled to an external output drive mechanism, such as the drive mechanism 530 described in connection with FIG. 5 above. Unlike the embodiment of FIGS. 2-7D, the input shaft 838 includes recesses (not shown) within which protrusions 532 and 534 can be received and may or may not include flexural members like those discussed in connection with the use recording device 213 described above. In the embodiment of FIG. 8, other components (e.g., stop 848 and detents 846 discussed herein) function as a locking mechanism to prevent inadvertent movement (e.g., undesired back driving or forward driving) of the recording device. The input shaft 838 can alternatively include any interface that enables torque transmission between the input shaft 838 and an external output drive mechanism (e.g., a manual drive mechanism or from a teleoperated computer-assisted manipulator system).

The worm drive 836 is operably engaged with a rotatable disc 818 that includes indicia, such as the integer numbers shown in FIG. 8, or any of the other types of indicia discussed above. The omitted housing portion of the instrument 800 can include an aperture (like aperture 215 (FIG. 2)) through which a single integer of the numbers on the rotatable disc 818 is displayed. In the embodiment of FIG. 8, the rotatable disc 818 is operably engaged with the worm drive 836 via a rotatable countershaft 840 carried by a bracket 842. The countershaft 840 carries pinion gears 844, one of which engages the worm drive 836 and the other of which engages the rotatable disc 818.

Figure 9:
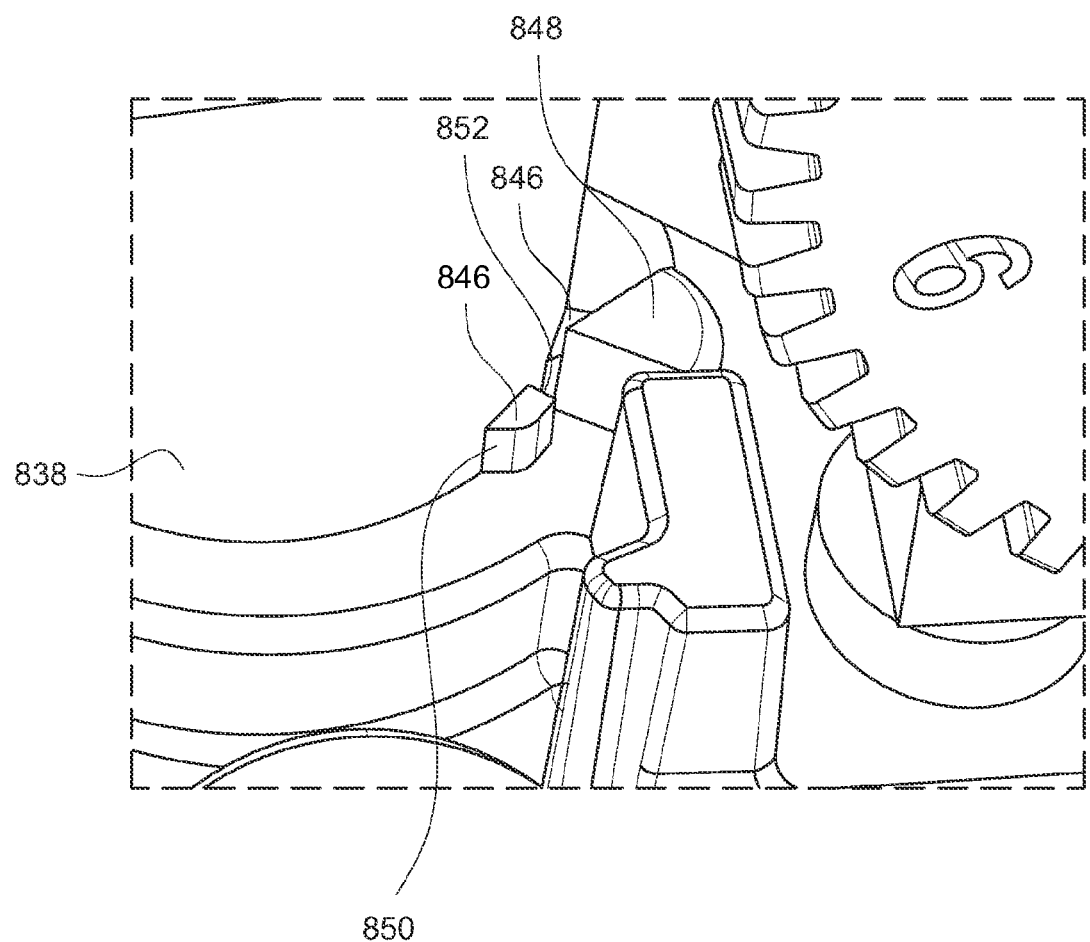
FIG. 9 is a detail view of portion 9-9 the device shown in FIG. 8.

The use recording device 814 includes features to prevent back-driving of the rotatable disc 818 and ensure the rotatable disc 818 remains in the same indicated position when the instrument is disconnected from an external drive mechanism (e.g., of a manipulator system or otherwise) and stored, transported, or otherwise handled. For example, referring now to FIG. 9, an enlarged detailed perspective view of portion 9-9 of FIG. 8 is shown. The input shaft 838 includes one or more detents 846 positioned to contact one or more stops 848 on the housing 815 of the instrument 800. The detents 846 have a ramped leading edge 850 and a flat trailing edge 852. Torque applied by the drive mechanism (e.g., drive mechanism 530 in FIG. 5) is sufficient to drive the ramped leading edge 850 past the stop 848 as the input shaft 838 rotates in the clockwise direction of FIG. 9, but interference between the flat trailing edge 852 and the stop 848 prevents back-driving of the input shaft 838 in the counterclockwise direction of FIG. 9. Other configurations of components to prevent back driving of the use recording device are within the scope of the disclosure, such as, without limitation, systems similar to the flexural members 224, 226 of the device of FIGS. 2-4, ratcheting mechanisms, or other arrangements.

Figure 10:
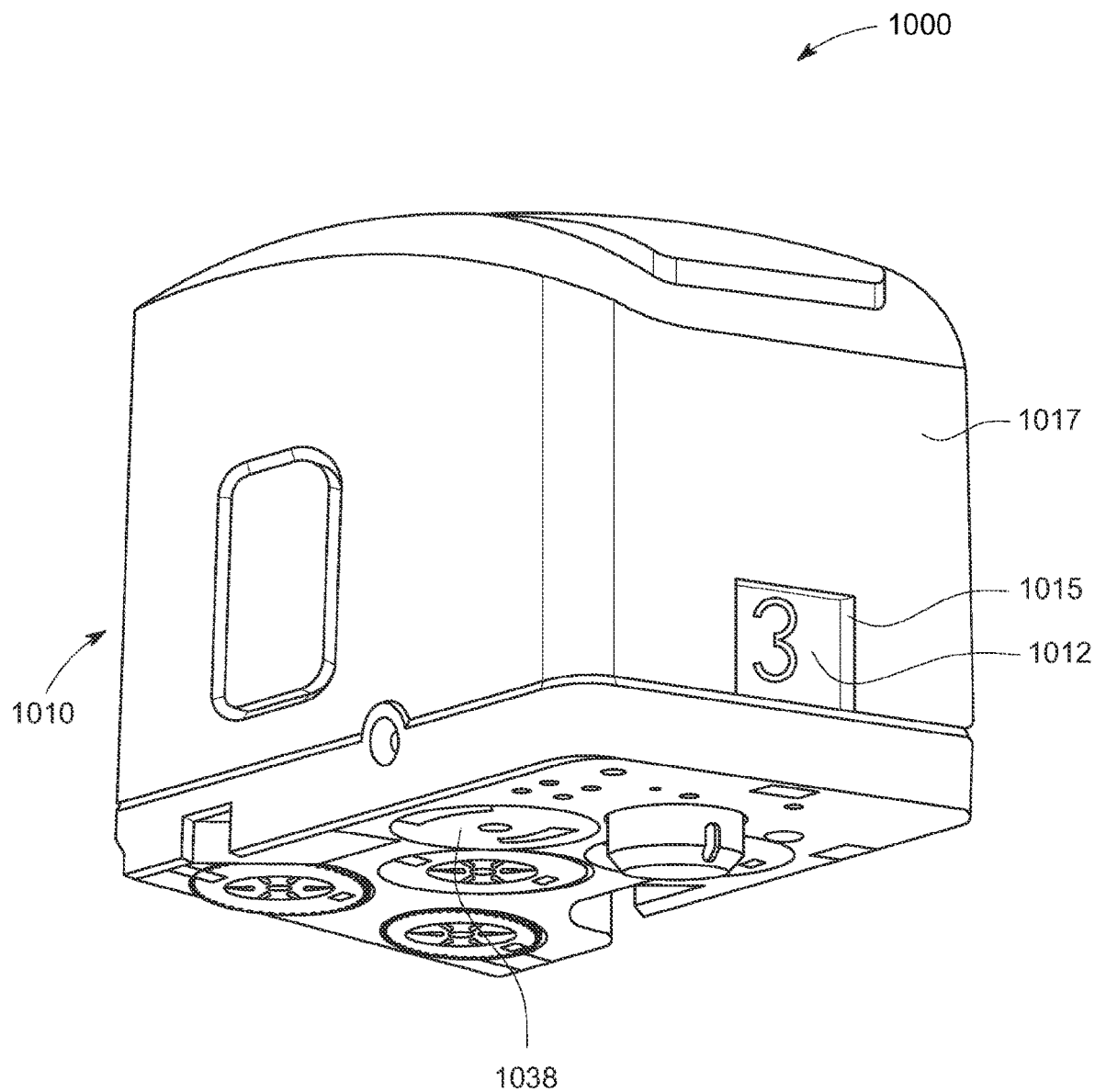
FIG. 10 is a perspective view of a portion of an instrument and device for recording use of the instrument according to another exemplary embodiment of the present disclosure.

Referring now to FIG. 10, a perspective view of another embodiment of a transmission mechanism portion of an instrument that comprises a use recording device is illustrated. The transmission mechanism 1010 includes visual display 1012 showing indicia (the 3 in FIG. 10 is exemplary only) that is viewable through an aperture 1015 in the housing 1017 of the transmission mechanism 1010.

Figure 11:
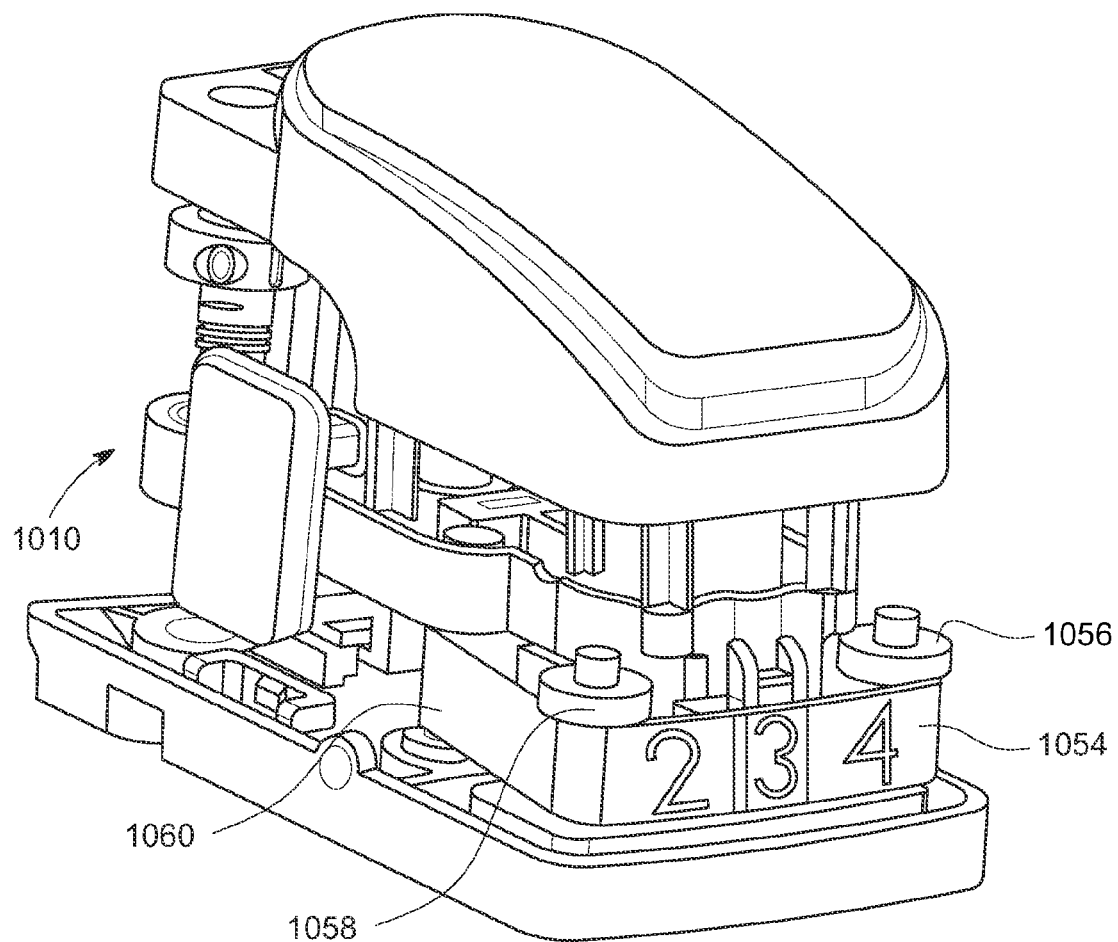
FIG. 11 is a perspective view of the portion of the instrument of FIG. 10 with a housing portion removed to reveal features of the present disclosure.

FIG. 11 shows the transmission mechanism 1010 of FIG. 10 with the housing 1017 removed to reveal components of the use recording device. The use recording device includes a scroll 1054 comprising, e.g., a polymer film, fibrous sheet material, or other pliable substrate. The scroll 1054 includes visual indicia such as integer numbers, a tapered graph indicator, or other visual indicia as discussed above. The scroll 1054 extends around a feed pulley 1056, passes around an idler pulley 1058, and wraps around a winding pulley 1060. The winding pulley 1060 is operably coupled to an input device 1038 (FIG. 10), which can be engaged with an external output drive mechanism of a manipulator system, such as manipulator systems discussed in connection with FIGS. 13 and 14 below, or a manual manipulator. Such engagement can include any of the arrangements discussed above, or other engagement arrangements as would be apparent to one having ordinary skill in the art. When the instrument 1000 is engaged with a manipulator system, the manipulator system can actuate the output drive mechanism (such as output drive mechanism 530 in FIG. 5) to rotate the input device 1038 as discussed above with reference to FIG. 10. Rotation of the input device 1038 rotates the winding pulley 1060 and causes the scroll 1054 wrap around the winding pulley 1060 and to unwrap from the feed pulley 1056, advancing the portion of the scroll 1054 shown through the aperture 1015.

As the scroll 1054 wraps around the winding pulley 1060, the effective diameter of the winding pulley 1060 increases due to the thickness of the material of the scroll 1054 wrapped around it. Thus, for a given amount of rotation of the winding pulley 1060, a greater additional portion of the scroll 1054 will be wrapped around the winding pulley 1060 depending on how much of the scroll 1054 is already present on the winding pulley 1060. To accommodate this, the indicia on the scroll 1054 can be provided at successively greater spacings such that as greater amounts of the scroll 1054 are wrapped around the winding pulley 1060, each indicium still appears in the aperture 1015. Alternatively, the manipulator system can be programmed to advance the winding pulley by a lesser rotational amount for each rotation, thereby permitting equally-spaced indicia on the scroll 1054 to each properly appear in the aperture 1015.

Figure 15:
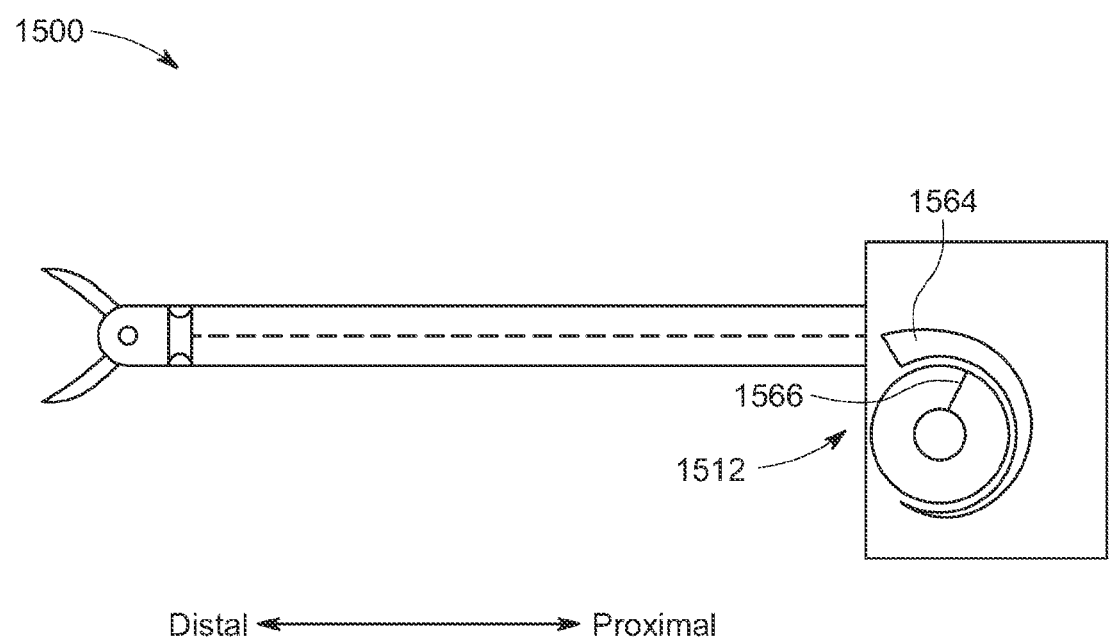
FIG. 15 is a schematic side view of an instrument comprising a device for recording use of the instrument according to another exemplary embodiment of the present disclosure.

While the embodiments shown and described above in connection with FIGS. 2-11 include indicia featuring integer numbers, as discussed above, other configurations of indicia are within the scope of the disclosure. For example, FIG. 15 shows an instrument 1500 with a use recording device, of which a visual display 1512 comprising a tapered graph 1564 is shown in FIG. 15. The visual display 1512 includes a pointer 1566 coupled to a use recording device that can be or include the use recording device components discussed above in connection with FIGS. 2-11, or another system. As the instrument 1500 is used, the pointer 1566 on the incrementally movable component (e.g., rotatable disc 218 (FIG. 2), rotatable disc 828 (FIG. 8), or scroll 1054 (FIG. 10)) moves along the tapered graph 1564 and the position of the pointer relative to the tapered icon indicates a fraction of life of the instrument 1500 remaining. Alternatively, the tapered icon could be in the form of a bar graph, gradually increasing dots, gradually changing colored segments (e.g., green, yellow, orange, red), or have another configuration. Further, rather than having a pointer move in response to use, the tapered icon can optionally be placed on a moving component of the use recording device, such as on rotatable disc 218 (FIG. 2,) 828 (FIG. 8), or scroll 1054 (FIG. 10) or other component, and a stationary pointer or other indicator can be provided, e.g., on the housing of the instrument 1500. Similar to the embodiment in which the pointer moves, relative position of the tapered graph and pointer indicates the fraction of instrument life remaining. Further, rather than providing a pointer, a portion of the tapered graph can be exposed, e.g., through an aperture of the housing, and the portion of the tapered graph exposed indicates the fraction of instrument life remaining.

Figure 12:
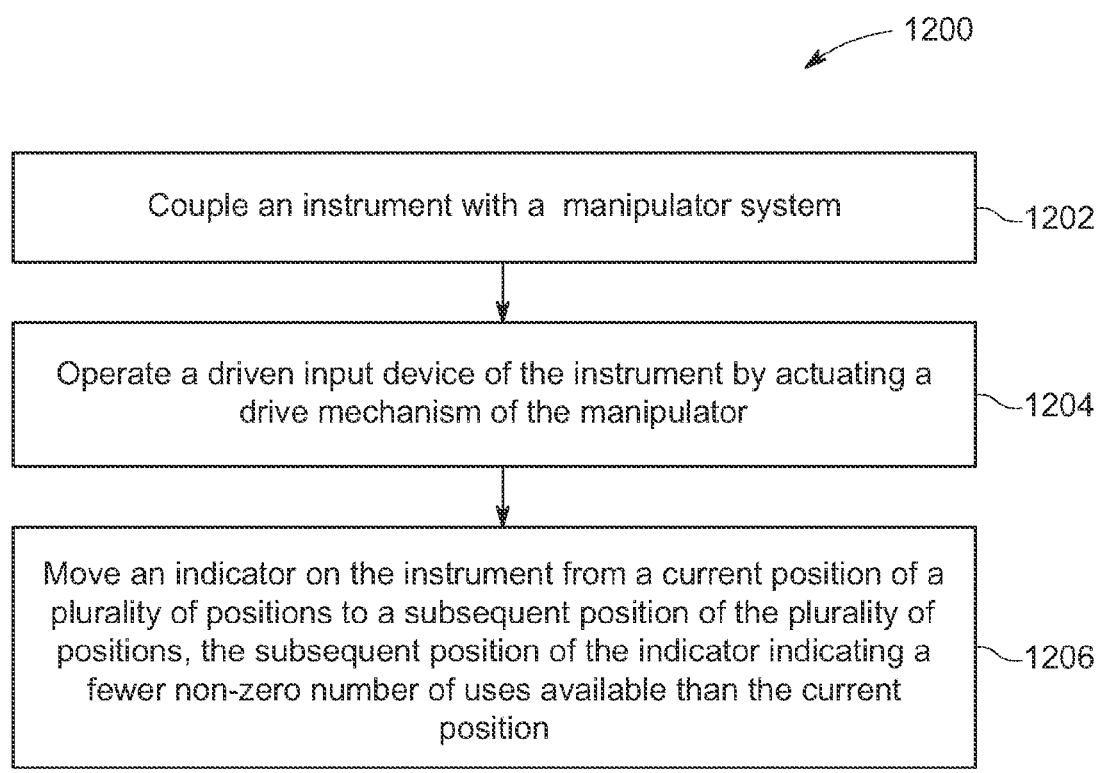
FIG. 12 is a flow chart showing a workflow for operating a device for recording use of an instrument according to an exemplary embodiment of the disclosure.

FIG. 12 is a flowchart showing a workflow 1200 for recording and indicating a number of remaining available uses of an instrument. At 1202, the method includes coupling an instrument with a manipulator system, such as a teleoperated system that works in part with computer-assistance, or a manual manipulator system. For example, instruments 100, 200, 800 can be coupled with a manipulator system such as the manipulator systems discussed in connection with FIGS. 13 and 14 below. At 1204, the method includes operating a driven input device of the instrument by actuating an external drive mechanism such as an output drive mechanism of the manipulator system. For example, the rotatable disc 218, input shaft 838, or input shaft 1038 is rotated by an external output drive mechanism. At 1206, the method includes moving an indicator on the instrument from a current position of a plurality of positions to a subsequent position of the plurality of positions, the subsequent position of the indicator having indicia indicating a fewer non-zero number of uses available than the current position. For example, the rotatable discs 218, 818 or the scroll 1054 can be moved to display a different indicium representing a specific number of remaining uses available, which number is decreased from an initial number or non-numerical indicia according to the examples discussed herein.

While the various indicators disclosed herein show a series of consecutive integer numbers reflecting one use per position, other configurations are contemplated, including non-consecutive series of integer numbers. For example, based on the configuration and programming of the manipulator system, uses could be counted down by multiples. For example, the rotatable disc or other indicators could have consecutive positions that count down by 2 s, 3 s, 5 s, 10 s, etc., and the manipulator could correspondingly be programmed to decrement a position every 2, 3, 5, 10, etc. uses. Further, the indicators disclosed herein could be used only to indicate a portion of a series of uses the instrument can undergo. For example, the indicator could be used to indicate only the last 10, 5, or other number of uses of a greater number of total available uses. In such embodiments, the manipulator system could be programmed to begin decrementing the indicator devices only once an initial number of uses are completed. For example, for an instrument with, e.g., 30 total available uses, the manipulator could be programmed to allow 20 uses before beginning to decrement a 10-use counter for the final 10 uses of the instrument. Other arrangements, such as irregular counts on the indicators, such as showing an irregular series of 20, 10, 9, 8, 7, etc. down to 0 available uses are also contemplated within the disclosure.

Embodiments of the present disclosure provide reliable and robust devices that record and display one or both of a number of times an instrument has been used, or a number of available remaining uses of the instrument. Such devices can be easily viewed by personnel when the device is unconnected to a manipulator system, such as in storage or during transport.

Instrument Reprocessing Recording Devices, Systems, and Methods

Further embodiments of the present disclosure include various devices, and related systems and methods, for recording one or more events, such as a change in environmental conditions occurring during a reprocessing procedure, to which an instrument, such as a medical instrument, is subjected. Such reprocessing procedures can involve application of heat and result in a temperature excursion, application of ultrasonic or other mechanical energy, exposure to pressure cycles, or other conditions. In various embodiments, recording devices according to the present disclosure can operate based on exposure to temperature changes, exposure to pressure changes, and/or application of various forms of energy (e.g., ultrasonic energy) to which an instrument may be subjected, such as during a reprocessing procedure, so as to be able to record a number of instances the instrument has been so subjected. These reprocessing recording devices can be mechanical devices made of relatively few moving parts. Moreover, in some embodiments, the recording devices do not require a constant electrical power source to operate. Further, recording devices according to various exemplary embodiments can operate reliably and independently within relatively extreme environments, such as in one or more of wet or vaporous environments, environments that have chemicals, environments with relatively high or relatively low temperatures, including washing, sterilization and/or autoclave temperatures for example, environments having high humidity levels, environments at relatively high or low pressures, and environments subjected to various energy modes, such as, for example, in an ultrasonic washer environment, fluidic flushing, and/or mechanical agitation.

Reprocessing recording devices according to various embodiments can optionally comprise devices, such as electronic devices and/or analog devices, for storing and allowing readout of information regarding the number of occurrences of recorded events to which an instrument has been subjected, such as during a reprocessing procedure. In various embodiments, such storage and indication devices also may not require any external power source. Moreover, the reprocessing recording devices according to various embodiments incorporate features to mitigate damage to the electronics and other components that could otherwise occur as a result of the environments to which an instrument may be subjected, for example, either during use or during reprocessing.

Reprocessing recording devices according to various embodiments of the present disclosure can include one or more state-change elements, such as, but not limited to, for example, temperature-responsive elements, pressure-responsive elements, or vibration-responsive elements, that undergo a change of state in response to a change in an environmental condition. Such changes in condition can include one or more of a temperature change, a pressure change, a change in humidity, a change in mechanical agitation, and other changes in environmental conditions to which the element may be subjected and designed to respond to by a change in state. In a non-limiting embodiment, an amount of change that causes the state-change element to change states may be predetermined and/or may be associated with a reprocessing procedure to which the instrument is subjected.

For example, one or more temperature-responsive elements can be configured to transition from a first state to a second state when a temperature transitions from a first temperature to at least a second temperature. In an exemplary embodiment, the first temperature may be below a predetermined threshold temperature and the second temperature may be at or above the predetermined threshold temperature. Such temperature-responsive elements can include various components such as shape-memory components, wax motors, bimetallic components, temperature-sensitive electronic switches, bladders or other reservoirs containing substances that undergo state and/or volume changes in response to temperature changes, or other components. These components are designed to undergo a state change, such as a change in physical dimension, shape, position, and/or phase so as to apply a force or other action as a result of reaching a predetermined temperature threshold, which in an exemplary embodiment may be associated with reprocessing.

Other state-change elements can include pressure-responsive elements, such as, but not limited to pressure-responsive actuators that generate movement based on application of pressures deviating from a set pressure, such as an atmospheric pressure, energy harvesting devices that generate an electrical current based on application of mechanical energy, such as ultrasonic vibration, or other devices that exhibit a change in state based on a change in conditions to which the element is exposed.

The state-change elements can be operably coupled with a counter mechanism that records the occurrence of an event associated with a change in environmental conditions to which the state-change element is responsive to cause it to change state. As a nonlimiting example, the event may be one associated with a reprocessing procedure. The counter mechanism and the state-change element can be operably coupled such that as the instrument comprising the reprocessing recording device undergoes a reprocessing procedure, the counter mechanism increments to reflect the occurrence that the instrument was subjected to such reprocessing procedure. For example, the counter mechanism can be incrementally movable in response to each change in state of the state-change element from the first state to the second state. That is, the counter mechanism can record a number of transitions of the state-change element from the first state to the second state.

In various exemplary embodiments, the counter mechanism can comprise or be operably coupled with a storage device that stores and/or provides information indicative of a number of recorded occurrences of one or more exposures to a change in environmental condition, such as temperature, pressure, or energy excursion (e.g., to at least a predetermined threshold), etc., which may be associated with a reprocessing procedure to which an instrument has been subjected. In some cases, the information may be, for example, a remaining number of reprocessing procedures to which the instrument can be subjected. For example, the storage device can be a visual indicator, such as an incremental counter that displays one or both of a number of reprocessing procedures to which the instrument has been subjected and a remaining number of reprocessing procedures to which the instrument can be subjected. In other embodiments, the storage device can include a gauge-type indicator that shows a proportion of reprocessing procedures used, or reprocessing procedures remaining, out of a total overall amount of acceptable reprocessing procedures, similar to a vehicle gas gauge for example. Additionally, or alternatively, the counter mechanism can comprise or be operably coupled to an electronic non-volatile memory as a storage device, which can be later read out electronically, such as when coupled to a surgical system. Storage devices according to the present disclosure including indicators and electrical storage devices can be referred to as "user-accessible storage devices" herein.

In some aspects of the disclosure, the recording device can be configured to render the instrument inoperable after the counter mechanism has counted a specified number of temperature, pressure, energy, or other environmental exposure conditions of a predetermined level to which the instrument has been subjected, for example, such as conditions associated with reprocessing procedures. For example, in an embodiment, in addition to or in lieu of providing information regarding the number of reprocessing procedures an instrument has been subjected to or the number of such acceptable procedures remaining, a lockout (rendering the instrument unusable) of the instrument may occur. Such a lockout may be used, for example, for an instrument that is intended to be a single-use device and not designed to be reprocessed for subsequent use.

Figure 16:
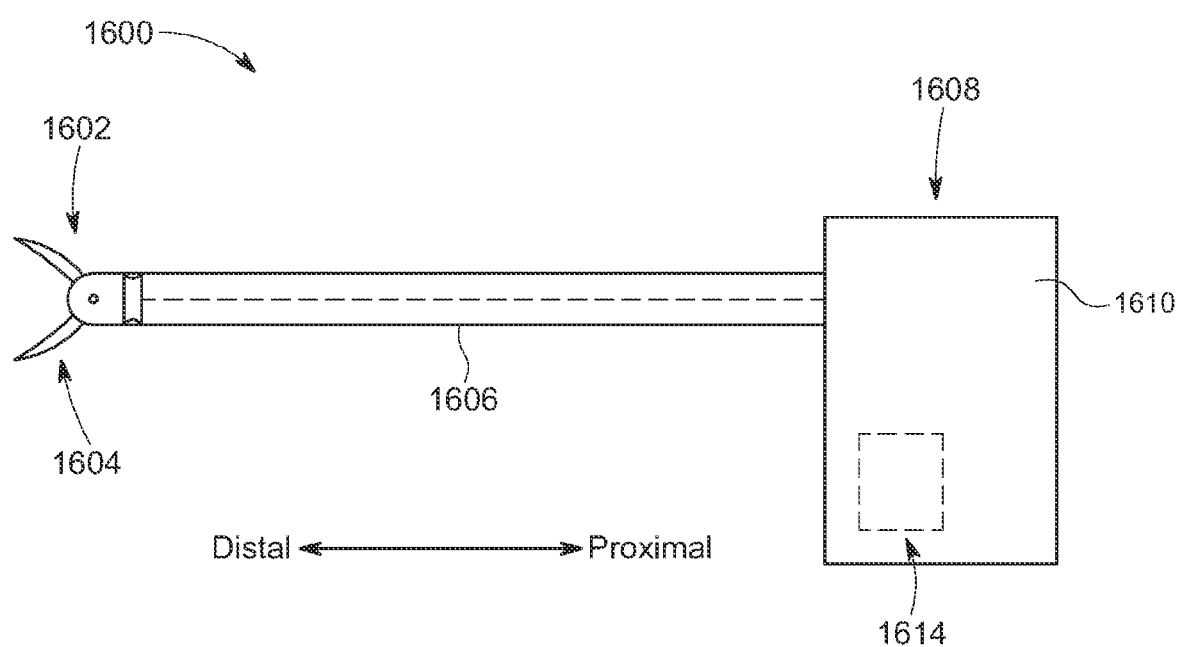
FIG. 16 is a schematic side view of an instrument equipped with a device for recording a reprocessing procedure to which the instrument is subjected according to an exemplary embodiment of the present disclosure.

Referring now to FIG. 16, a schematic view of an instrument 1600 according to an exemplary embodiment of the disclosure is shown. The instrument 1600 includes a shaft 1606 extending from a distal end portion 1602 at which an end effector 1604 is located to a proximal end portion 1608 at which a transmission mechanism 1610 is located (1610 showing the outer housing of a transmission mechanism). The end effector 1604 can include, without limitation, a surgical tool such as shears, forceps, an electro-surgical tool, an imaging device or other sensor, a suturing tool, or any other medical or non-medical tool. The transmission mechanism 1610 can include various drive mechanisms (e.g., gears, capstans, linkages, input disks etc.) connected to various cables and rods to control motion and operation of the shaft and end effector, as those having ordinary skill in the art are familiar with. The transmission mechanism 1610 can optionally be configured to operably couple with a computer-controlled (e.g., teleoperated) surgical manipulator system, such as, by way of non-limiting example, any of the manipulator systems that are part of the teleoperated surgical systems that operate at least in part with computer assistance, such as the da Vinci® Surgical Systems commercialized by Intuitive Surgical, Inc., of Sunnyvale, California Those of ordinary skill in the art would appreciate, however, that the instruments, devices, and techniques discussed herein can be implemented using other types of teleoperated, computer-assisted surgery platforms. In yet other embodiments, the transmission mechanism 1610 can include actuators (not shown) for manual control of various functions/movement of the instrument 1600, and the instrument 1600 can be a manually operated instrument.

The instrument 1600 further comprises a recording device 1614 for recording one or more changes in environmental condition to which the instrument is subjected. The recording device 1614 can be mounted to or otherwise integrated as part of the housing of the transmission mechanism 1610 or another portion of the instrument 1600. The recording device 1614 can record, and optionally store and provide information indicative of occurrences of temperature, pressure, and/or applied energy excursions, which may be, for example, associated with the number of reprocessing procedures to which the instrument 1600 has been exposed. Such recording may be based, for example, on a change of state of a state-change element operably coupled with a recording device.

Figure 17:
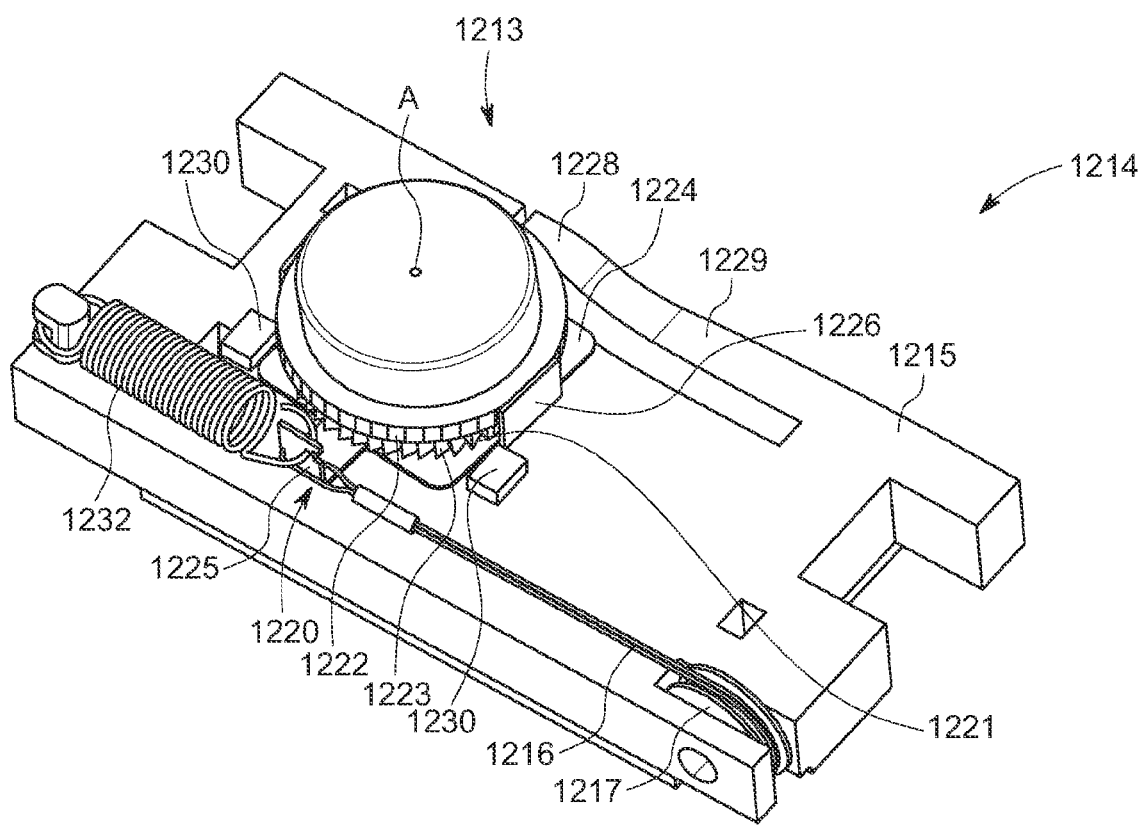
FIG. 17 is a perspective view of a device for recording a reprocessing procedure according to another embodiment of the present disclosure.
Figure 18A:
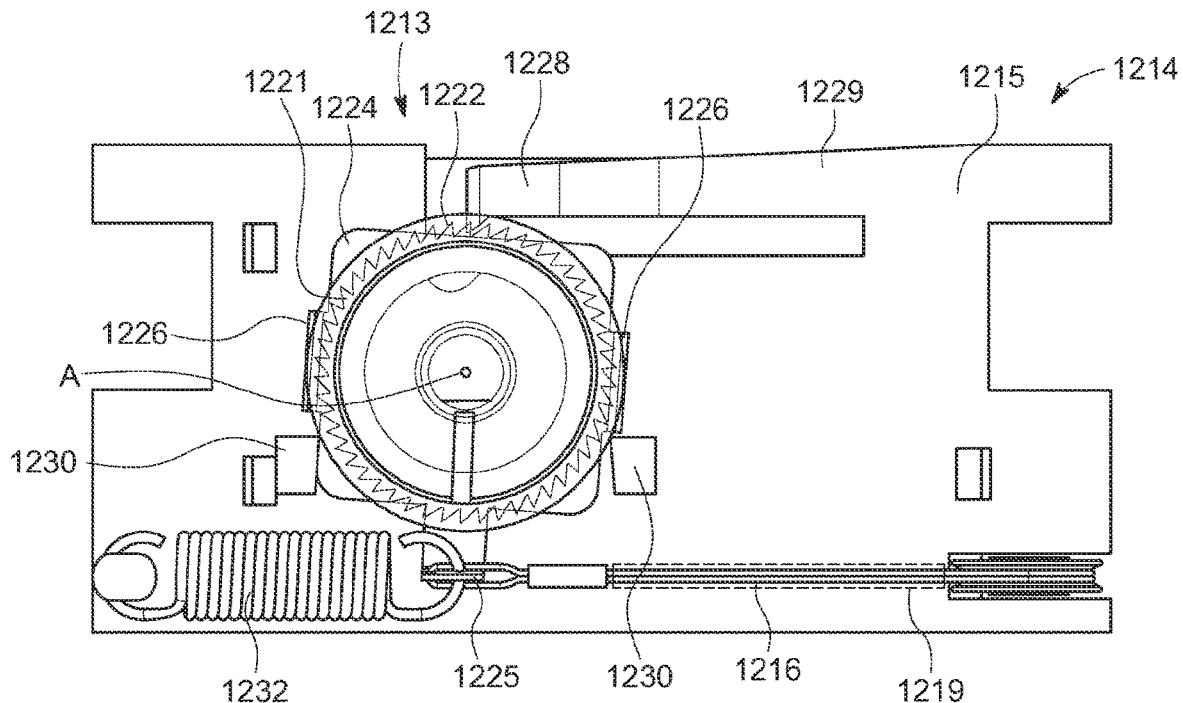
FIG. 18A is a plan view of the device of FIG. 17, showing the device in a first state according to an embodiment of the present disclosure.
Figure 18B:
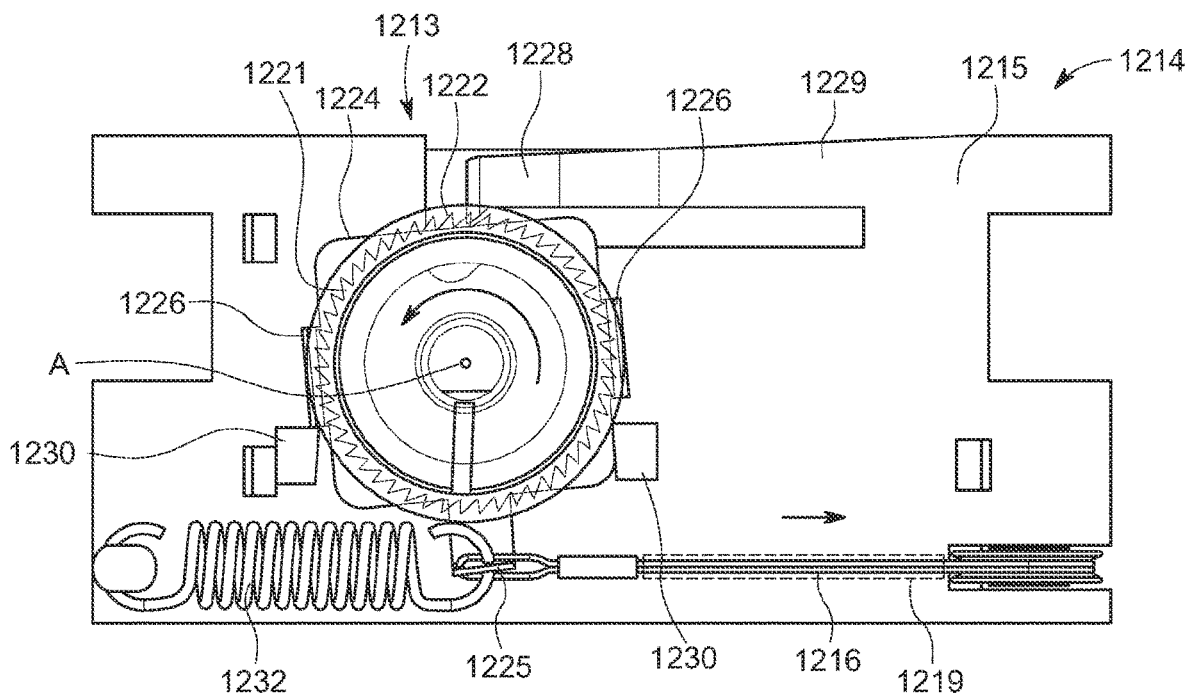
FIG. 18B shows the device of FIG. 18A in a second state according to an embodiment of the present disclosure.

Referring now to FIGS. 17, 18A, and 18B, a reprocessing recording device according to an exemplary embodiment of the present disclosure is shown. The environment exposure recording device 1214 is shown in FIG. 17 isolated from the instrument 1600 of FIG. 16 to facilitate illustration, but as discussed above, the recording device 1214 can also be integrated as part of a component of the instrument 1600, such as a backend transmission mechanism, as would be appreciated by one of ordinary skill in the art. The recording device 1214 includes a temperature-responsive, state-change element configured to undergo a change of state based on exposure to a temperature change, such as an elevation in temperature associated with a reprocessing event (e.g., washing with or without ultrasonic energy, and/or autoclaving, drying, etc.). Further, a person having ordinary skill in the art would understand that temperature changes such as excursions to a lower temperature could be recorded instead of, or in addition to, elevations in temperature.

The temperature-responsive element can be or include materials that change in physical configuration, such as one or more of a physical dimension (e.g., length, width, height, shape, and/or volume, etc.), or another change in state (e.g., position, rigidity, electrical charge, color, and/or phase) in response to exposure to a temperature above (or below) a specified threshold temperature. The threshold temperature can be defined by the conditions of a reprocessing procedure to which the instrument will be subjected. For example, the threshold temperature can be chosen to be greater than temperatures to which the instrument will be subjected during normal use and below a maximum temperature to which the instrument will be subjected during reprocessing. For example, an autoclave procedure may involve temperatures at or above 120° C. for a specified period of time, while a washing (e.g., ultrasonic washing) process may include temperatures elevated beyond normal ambient (e.g., room) temperatures but below autoclaving temperatures, or even below 100° C. The threshold temperature of the temperature-responsive element can be chosen such that the recording device only records an autoclave procedure, such as by choosing a threshold temperature above, e.g., 100° C., 120° C., or another threshold temperature, or to record both washing at elevated temperatures and autoclaving, such as by choosing a threshold temperature above the temperature used for washing, (such as a temperature in a range of, for example, from 70° C. to 90° C., depending on the temperature used during the washing process). Those having ordinary skill in the art will appreciate how to design and configure devices according to the present disclosure to respond to more than one type of temperature excursion if desired, such as to record differing types of reprocessing procedures with differing temperature characteristics using differing temperature-responsive, state-change elements.

In the exemplary device of FIGS. 17, 18A, and 18B, the temperature-responsive element is a wire, cable, or other similar member, made from a shape memory metal, such as nickel-titanium alloy (e.g., nitinol). Other embodiments can include other temperature-responsive elements, including but not limited to, wax motors, bimetallic components, temperature-sensitive electronic switches, or other components. These temperature-responsive elements can be configured to undergo a change in state upon a change in temperature, such as heating to at least a threshold temperature.

The shape-memory wire 1216 is operably coupled with a counter mechanism 1213 such that the counter mechanism 1213 records a change of state of the shape-memory wire 1216 resulting from exposure to temperatures elevated above the specified threshold temperature. One end portion of the shape-memory wire 1216 is routed around a pulley 1217, and an opposite end portion (not shown in FIG. 17; shown as 1216A in FIGS. 23A and 23B described further below) of the shape-memory wire 1216 is fixed to a base 1215 of the reprocessing recording device 1214.

In the device of FIGS. 17, 18A, and 18B, the counter mechanism 1213 is configured to incrementally move based on a change of state of the shape-memory wire 1216. For example, in the embodiment of FIGS. 17, 18A, and 18B, the counter mechanism 1213 comprises a ratcheting mechanism 1220. The ratcheting mechanism 1220 comprises a ratchet wheel 1221 having ratchet teeth 1222 that engage with one or more drive pawls 1226 mounted to a drive pawl carrier 1224. The ratchet wheel 1221, through engagement with the drive pawls 1226 and operation of the drive pawl carrier 1224 described further below, moves incrementally for each temperature excursion above the specified threshold temperature. As discussed in greater detail below, the ratcheting mechanism 1220 can include or be operably coupled with a user-accessible storage mechanism, such as the exemplary visual indicators 1418 (FIG. 19), 2018 (FIGS. 20A and 20B), 2118 (FIG. 21), 2218 (FIG. 22), electronic storage devices such as the exemplary electronic recording device described below in connection with FIGS. 23A and 23B, or other devices.

With reference to FIGS. 18A and 18B, the pawl carrier 1224 is rotatable about an axis A. The drive pawl carrier 1224 carries at least one drive pawl 1226. In the embodiment of FIGS. 17, 18A, and 18B, the drive pawl carrier 1224 includes two drive pawls 1226 positioned diametrically opposite one another on the pawl carrier 1224, but such configuration is not limiting and other numbers and arrangements of drive pawls 1226 would be apparent to those having ordinary skill in the art. The end portion of the shape-memory wire 1216 opposite to the end portion wrapped around the pulley 1217 is fixed to the drive pawl carrier 1224 in any appropriate manner. For example, in the embodiment of FIGS. 17, 18A, and 18B, the end portion of the shape-memory wire 1216 is crimped to form a loop and the loop is secured around an extension tab 1225 that extends from a side of the drive pawl carrier 1224. Further, one or more hard stops 1230 are positioned to provide interference with the rotation of the drive pawl carrier 1224 so as to limit the extent of rotation of which the pawl carrier 1224, and thus rotation of the ratchet wheel 1221, is capable with each incremental advancement.

The ratcheting mechanism 1220 can include features configured to prevent back-driving of the ratcheting mechanism 1220. For example, the ratcheting mechanism can include a locking pawl 1228 configured to engage with anti-backup ratchet teeth (not shown). The locking pawl 1228 allows movement of the ratchet wheel 1221 in the drive direction but prevents the ratchet wheel 1221 from rotating in a direction opposite the drive direction once advanced (e.g., the locking pawl 1228 permits movement of the ratchet wheel in the counterclockwise direction shown in FIGS. 18A and 18B and prevents the ratchet wheel 1221 from rotating clockwise). While in the embodiment of FIGS. 17, 18A, and 18B, the locking pawl 1228 engages with separate anti-backup ratchet teeth, in other exemplary embodiments the locking pawl 1228 can be configured to engage with ratchet teeth 1222. That is, in some designs, both the drive pawls 1226 and locking pawl 1228 can engage the same set of ratchet teeth, as will be apparent to one of ordinary skill in the art.

The locking pawl 1228 can be coupled to (e.g., integrated with) a flexure arm 1229. In the device of FIGS. 17, 18A, and 18B, the flexure arm 1229 is molded as part of the base 1215, and elastic deformation of the flexure arm 1229 permits rotation of the ratchet wheel 1221 in the drive direction as the anti-backup ratchet teeth 1223 deflect the locking pawl 1228 away from the ratchet wheel 1221. As would be readily understood, the flexure arm 1229 could alternatively be hinged to the base 1215, and one or more biasing members, such as springs, provided to ensure the locking pawl 1228 returns to an un-deflected position in engagement with the anti-backup ratchet teeth to prevent back-driving of the ratchet wheel 1221.

The reprocessing recording device 1214 can also be configured to bias the pawl carrier 1224 in an initial position (e.g., the position shown in FIG. 18A). In the device of FIG. 18A, a biasing element in the form of an extension spring 1232 is coupled to the pawl carrier 1224 to bias the pawl carrier 1224 to a biased position. The extension spring 1232 is fixed to the base 1215 of the recording device 1214 at one end and to the drive pawl carrier 1224 at a location proximate where the shape-memory wire 1216 is fixed, for example, to the extension tab 1225 in the embodiment of FIGS. 17, 18A, and 18B. The extension spring 1232 generally extends and retracts along the direction the shape-memory wire 1216 extends and contracts. While the extension spring 1232, hard stops 1230, and the locking pawl 1228 are shown in FIGS. 17, 18A, and 18B as being either integral with or coupled to the base 1215, one of ordinary skill in the art will understand that the base 1215 can be a separate component of the instrument 1600 (FIG. 16), or can be integrated with a housing or main chassis of the instrument 1600, such as a back end transmission mechanism 1610 (FIG. 16).

The counter mechanism 1213 operation is actuated by the shape-memory wire 1216's exposure to temperature excursions. For example, the shape-memory wire 1216 reduces in length when heated to or above the specified threshold temperature, due to a transition from martensitic state to austenitic state of the nitinol material. As the shape-memory wire 1216 shortens, tension generated in the shape-memory wire 1216 acts against the biasing force of the extension spring 1232, extending the spring 1232 and causing the drive pawl carrier 1224 to rotate, e.g., in the counter-clockwise direction as viewed in FIGS. 18A and 18B. The drive pawls 1226 engage the ratchet teeth 1222 of the visual indicator 1218 and rotate the ratchet wheel 1221 in the counterclockwise direction. While the drive pawls 1226 rotate the ratchet wheel 1221 in the counterclockwise direction in FIGS. 18A and 18B, other possible arrangements are within the scope of the disclosure, including rotation of the ratchet wheel 1221 in the clockwise direction.

As shown in FIG. 18B, the drive pawl carrier 1224 is rotated to a predetermined limit in the counterclockwise direction until it engages with the hard stops 1230 that prevent further rotation of the pawl carrier 1224. As the ratchet wheel 1221 rotates with the pawl carrier 1224 due to engagement of the drive pawls 1226 with the ratchet teeth 1222, the locking pawl 1228 rides over one or more of the anti-backup ratchet teeth 1223 as the ratchet wheel 1221 assumes a new rotated position, at which position the locking pawl 1228 prevents counter-rotation (e.g., in the clockwise position as described above). As will be apparent to one of ordinary skill in the art, the described ratcheting functionality of the drive pawls 1226 and locking pawl 1228 in conjunction with the ratcheting teeth 1222 and anti-backup ratcheting teeth 1223 can be obtained by the profile of the respective teeth, the orientation and shape of the drive pawls, and other factors of which those having ordinary skill in the art would readily appreciate.

Upon cooling from the elevated temperature to resume its martensitic state, the shape-memory wire 1216 lengthens, removing the force exerted against the biasing force of the extension spring 1232 and allowing the extension spring 1232 to retract and return the drive pawl carrier 1224 to the initial position shown in FIG. 18A. The ratchet wheel 1221 remains in the new rotated position due to engagement of the locking pawl 1228 with the ratchet teeth 1222.

The length of the shape memory wire 1216 can be chosen such that a total change in length of the shape-memory wire is sufficient to move the drive pawl carrier 1224 the required amount to cause the ratchet wheel 1221 to assume a new position. In the embodiment of FIGS. 17, 18A, and 18B, wrapping the shape-memory wire 1216 around the pulley 1217 provides additional length in a small footprint of the recording device 1214 to accommodate a greater total length change if needed. Other configurations of the shape memory elements, including the use of more than one pulley and directional change, zig-zag patterns, or any configuration by which the shape memory element is provided with sufficient length are within the scope of the disclosure. Additionally, while the embodiment of FIGS. 17, 18A, and 18B includes the pulley 1217 to reduce friction on the shape-memory wire 1216, arrangements with or without pulleys are possible. The arrangement of the wire also may be such as to extend generally straight with no changes in length, depending on the available room in the instrument and the total length change required by the design of the ratcheting mechanism.

Rotational advancement of the ratchet wheel 1221 can correspond to a change in the indicated number of reprocessing cycles available for the instrument to be subjected to (or the number of indicated reprocessing cycles the instrument has undergone), as discussed below in connection with FIGS. 19-22.

In the embodiment of FIGS. 17, 18A, and 18B, the temperature-responsive element is a wire 1216 made from a shape memory metal, such as nickel-titanium alloy (e.g., nitinol). Other embodiments can include other temperature-responsive elements, including but not limited to, wax motors, bimetallic components, temperature-sensitive electronic switches, bladders or other reservoirs containing substances that undergo phase changes, dimension changes, position changes, volume changes, or other changes in response to temperature changes, or other components. These temperature-responsive elements can be configured to undergo a change in state upon heating to the specified threshold temperature. Additionally, while the embodiment of FIGS. 17, 18A, and 18B includes a shape memory alloy wire that shortens in response to elevated temperatures, other configurations, such as a shape memory alloy wire that lengthens in response to elevated temperatures or alters other dimensions responsive to elevated temperatures, are within the scope of the disclosure.

In some cases, an autoclave procedure can include several temperature and/or pressure cycles during a single procedure. For example, an autoclave can be configured to repeatedly cycle the pressure in the autoclave environment from a high-pressure environment to a low (e.g., at or near vacuum) pressure environment back to high pressure to ensure steam is driven into crevices and other relatively inaccessible areas of the instrument. The temperature of the autoclave environment likewise cycles according to the pressure change based on the physical relationship between pressure and temperature of a closed system, as will be clear to one of ordinary skill in the art. To avoid the temperature-responsive elements undergoing the change in state for each individual cycle of the pressure in the autoclave environment, the temperature responsive element can be tailored to provide a response time long enough that the change in state does not occur repeatedly for each pressure cycle. Alternatively, pressure-responsive state-change elements such as those discussed in connection with FIG. 28, or other state-change elements as discussed herein, can be used.

Various approaches can be used to configure the temperature-responsive element with the desired response time. One approach can include configuring the thermal mass of the temperature-responsive element such that the temperature-responsive element provides the desired response times. For example, a temperature-responsive element with a relatively greater thermal mass will typically exhibit a relatively longer response time. Another approach for adjusting the response time of the temperature-responsive element can include providing insulating material around the temperature-responsive element to slow the flow of heat to and from the temperature-responsive element. For example, in the device of FIGS. 17, 18A, and 18B, the shape-memory alloy wire 1216 can be surrounded by an insulating material, such as an insulating tube 1219. Insulating materials can include, for example and not limitation, polymer materials, ceramic materials, composite materials, and any other material that exhibits the desired insulating properties (e.g., desired rate of heat transfer given the volume and configuration of the insulating material, temperature/pressure cycle times to which the device is exposed, and other factors as would be apparent to one of ordinary skill in the art).

Figure 19:
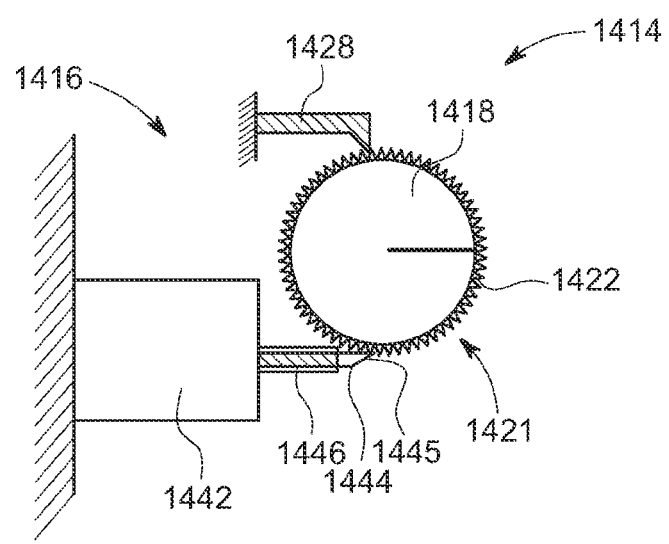
FIG. 19 is a schematic view of a device for recording a reprocessing procedure according to another exemplary embodiment of the present disclosure.

With reference now to FIG. 19, an exemplary embodiment of a reprocessing recording device 1414 that uses a wax motor 1416 as the temperature-responsive state-change element is shown. The wax motor 1416 includes a volume of wax enclosed within a reservoir 1442. The reservoir 1442 is in communication with a piston 1444 in a bore 1446. A counter mechanism comprises a ratchet wheel 1421 positioned adjacent the wax motor 1416 includes ratchet teeth 1422. Similar to the embodiment of FIGS. 17, 18A, and 18B, a locking pawl 1428 engages with the ratchet teeth 1422 to permit rotation of the ratchet wheel 1421 in one direction while preventing rotation in the reverse direction. The ratchet wheel 1421 can be operably coupled to or include user-accessible storage device, such as, for example, a visual indicator 1418 that can function similarly to, for example and without limitation, any and all of the various storage devices described herein.

Upon being exposed to at least the specified threshold temperature, the wax in the reservoir 1442 expands, and forces the piston 1444 through the bore 1446. The piston 1444 can be configured to interact with a counting mechanism and/or storage device similar to those discussed elsewhere herein. For example, the piston 1444 can include a drive pawl 1445 that engages the ratchet teeth 1422 on the ratchet wheel 1421, rotating the ratchet wheel 1421 to a new rotational position. Upon cooling, the piston 1444 retracts, while the locking pawl 1428 holds the ratchet wheel 1421 in the new rotational position. Persons having ordinary skill in the art will appreciate that the wax motor 1416 could be replaced by a similar device using substances with temperature-dependent characteristics other than wax, such as other substances that undergo changes in phase, viscosity, volume, or other changes upon exposure to temperature excursions. For example, in some embodiments water could be used as a temperature-activate substance. Because water undergoes a significant volume change at 100° C., and typical autoclave processes exposes the instrument to temperature excursions above 100° C., a water-containing reservoir could be configured to operate similar to the wax motor 1416 discussed in connection with FIG. 19. Further, specifying the threshold temperature can be done, for example and without limitation, as discussed above in connection with the exemplary embodiments associated with FIGS. 17, 18A, and 18B.

In the device shown in FIG. 19, the ratchet wheel 1421 includes an indicator 1418. The indicator 1418 can, in conjunction with other indicia on the device 1414, store and/or provide information about the number of reprocessing procedures which the device 1414 has undergone.

For example, as discussed above, recording devices according to the exemplary embodiments of the present disclosure can be operably coupled with storage devices store information about the tracking of the counter mechanism and provide information to users regarding the same. Such user-accessible storage mechanisms can include, without limitation, mechanical visual indicators such as those shown and discussed in connection with FIGS. 20-22, and/or electronic devices, such as an electronic memory recording device like that shown and discussed in connection with FIG. 23.

For example, as described above, the visual indicator can be part of the ratchet wheel 1221 discussed in detail in connection with FIGS. 17, 18A, and 18B or the ratchet wheel 1421 discussed in connection with FIG. 19. Thus, the temperature-responsive elements, such as the shape-memory wire 1216 (FIGS. 17, 18A, and 18B) or the wax motor 1416 (FIG. 19) and the visual indicator (for example, indicator 1418 (FIG. 19), 2018 (FIGS. 20A and 20B), or 2118 (FIG. 21)) are coupled such that the visual indicator moves incrementally for each temperature excursion above the specified threshold temperature.

Figure 20A:
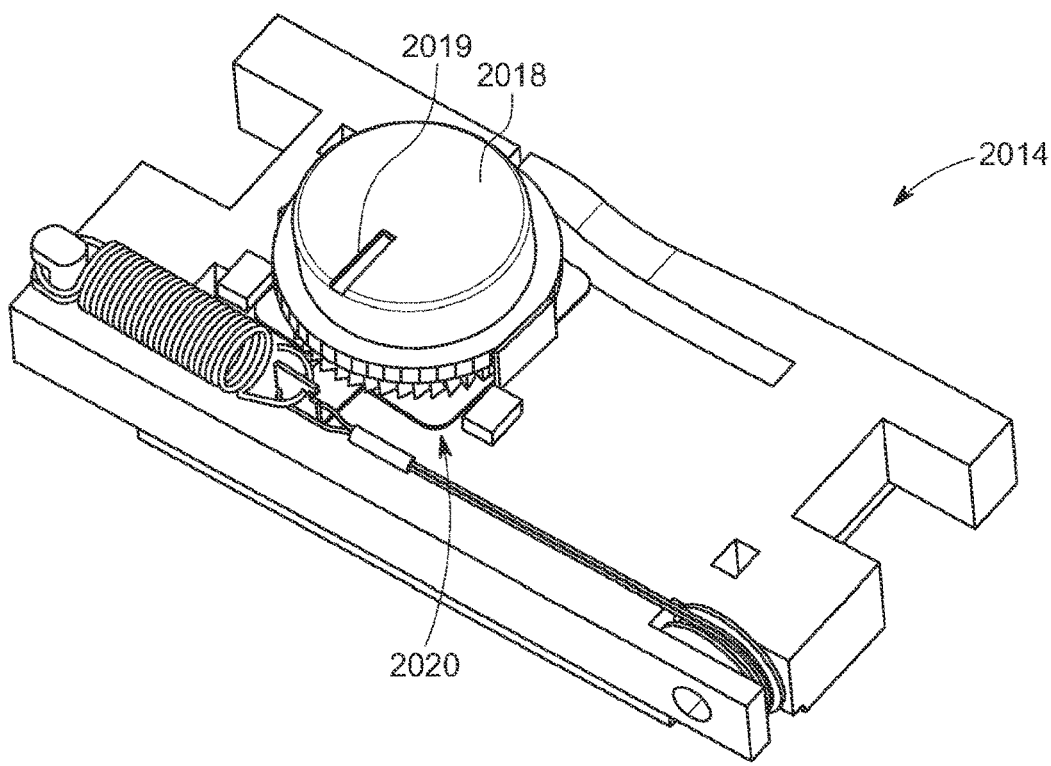
FIG. 20A is a perspective view of a device for recording a reprocessing procedure according to an exemplary embodiment of the present disclosure with a housing omitted to show internal components.
Figure 20B:
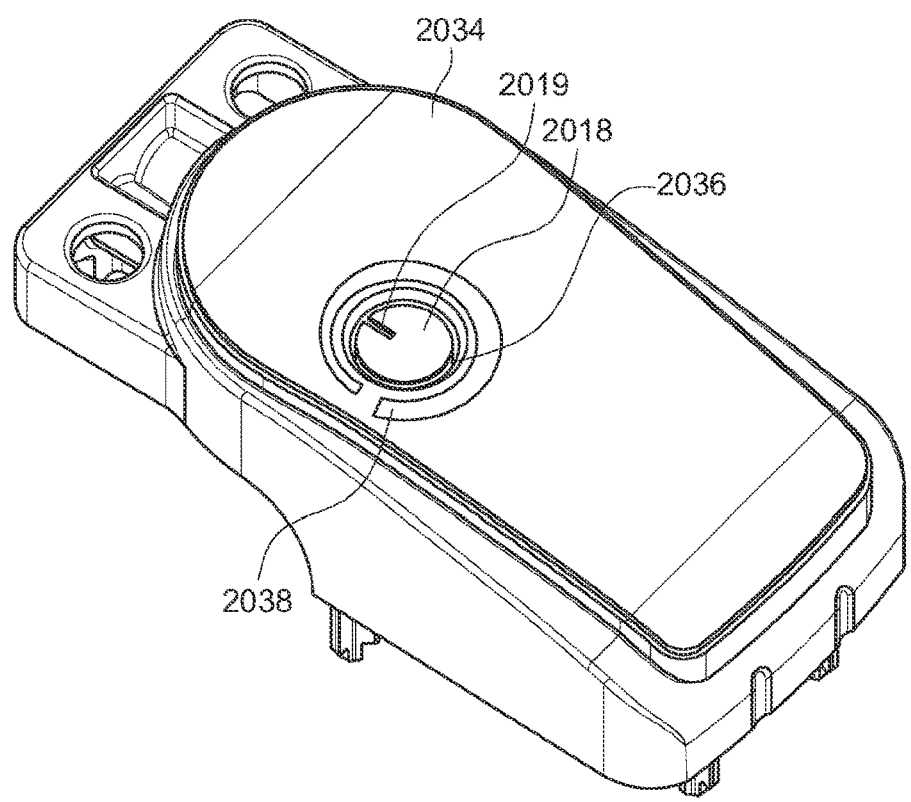
FIG. 20B is a perspective view of the device of FIG. 20A with a housing portion in place.

FIGS. 20A and 20B provide an example of a mechanical visual indicator according to an exemplary embodiment of the present disclosure, which may be used in conjunction with an instrument when a counter mechanism of the recording device is contained in a housing or as another internal part of an instrument. Referring now to FIG. 20A, a reprocessing recording device 2014 similar to recording device 1214 in FIGS. 17, 18A, and 18B is shown. The reprocessing recording device 2014 includes an indicator 2018 coupled with a ratcheting mechanism 2020 that functions like the ratcheting mechanism 1220 discussed in connection with FIGS. 17, 18A, and 18B. In this particular embodiment, the indicator 2018 comprises a pointer 2019 that is arranged to rotate with the ratcheting mechanism 2020 as the ratcheting mechanism 2020 responds to temperature excursions in the manner discussed in connection with FIGS. 17, 18A, and 18B.

The indicator 2018 may be used in conjunction with additional indications or other markings of the instrument to provide information regarding the number of times the instrument has been subjected to a temperature excursion, such as that associated with a reprocessing procedure. For example, referring now to FIG. 20B, an instrument housing 2034 includes an aperture 2036 through which a visual indicator 2018 is visible. The visual indicator 2018 may be coupled to, or be a portion of, a component of a recording device, such as reprocessing recording devices 1214 (FIGS. 17, 18A, and 18B) or 1414 (FIG. 19) discussed above.

The instrument housing 2034 can be provided with additional visual indicia that, when viewed in conjunction with the visual indicator 2018, reflects information regarding the number of temperature excursions to which the instrument has been exposed. For example, the information can represent the remaining number of reprocessing procedures to which the instrument can be subjected, the number of reprocessing procedures to which the instrument has been exposed, or other information. In the device of FIG. 20B, the visual indicia comprise a generally circular band 2038 that decreases in thickness (is tapered) as it extends around the aperture 2036. The pointer 2019 or other marker on the visual indicator 2018 points to a portion of the circular band 2038, with the thickness of the circular band 2038 at that point corresponding to the number of remaining reprocessing procedures to which the instrument can be subjected. In operation, as the instrument undergoes subsequent reprocessing procedures, the rotary visual indicator 2018 points to successively more narrow portions of the circular band 2038 to indicate use of the possible reprocessing procedures. It is also envisioned that in lieu of the tapered band 2038, a series of dots changing in size could be used as the visual indicia on the housing.

As an alternative to the graphical, fraction-type indicators discussed above, some devices according to the present disclosure can include indicators that include integer numbers that represent the possible reprocessing procedures to which the instrument can be subjected. For example, as shown in FIG. 21, a rotary visual indicator 2118 can be provided with a line 2119 or other marker that points to either successively higher or lower integer numbers provided on a housing 2134 as the instrument is exposed to temperature excursions, such as associated with reprocessing, and actuation of the temperature-responsive state-change element and counter mechanism described above occurs.

As discussed above, the number of times that an instrument can be subjected to a reprocessing procedure can depend on many factors, including regulatory requirements. The various reprocessing recording devices and indicators discussed herein can be configured to provide an indication of the number of times an instrument has been reprocessed. The total number of reprocessing procedures to which an instrument can be subjected can vary from, e.g., a single reprocessing procedure, to tens, hundreds, thousands, or more reprocessing procedures, and the various indicators described herein can be configured to indicate those numbers accordingly. As one non-limiting, exemplary range, the number of reprocessing procedures to which an instrument can be subjected can be, depending on various factors, in a range of from about 15 procedures to about 40 procedures, and the associated indicators can be configured accordingly.

Additionally, rather than including the visual indicia on the housing and a marker on the indicator, the visual indicia could be provided on the indicator and the marker on the housing, or only the portion of the indicator having visual indicia could be made visible through the aperture. For example, a series of integer numbers could be provided on the indicator, and the aperture could be sized such that only one of the numbers is visible, the visible number being indicative of the remaining reprocessing cycles available. Yet other indicator configurations are possible, as will be apparent to those having ordinary skill in the art, such as an indicator scheme based on color (for example, moving successively through green, yellow, orange, red as reprocessing procedures occur) or other indicator schemes.

Figure 21:
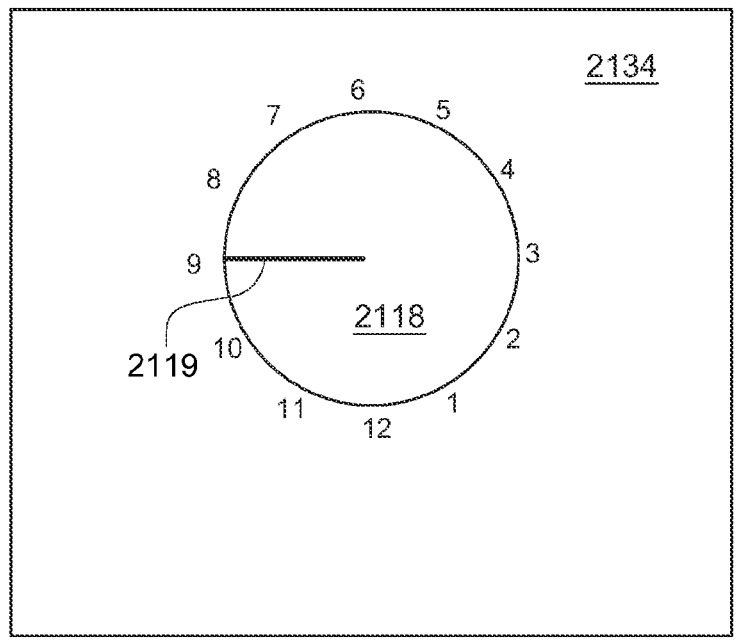
FIG. 21 is a plan view of a housing of an instrument with visual indicia according to another exemplary embodiment of the present disclosure.

While the embodiments of FIGS. 19-21 include various rotary visual indicators 1418, 2018, 2118, different configurations of ratcheting mechanisms and visual indicators are within the scope of the disclosure. For example, linear ratcheting mechanisms and linear indicators are contemplated that operate with a similar ratcheting action, as would be apparent to those having ordinary skill in the art. Such linear ratcheting mechanisms and linear indicators could be implemented with any of the temperature-responsive elements discussed herein, such as the shape-memory alloy wire 1216, the wax motor 1416, or other temperature-responsive elements.

Figure 22:
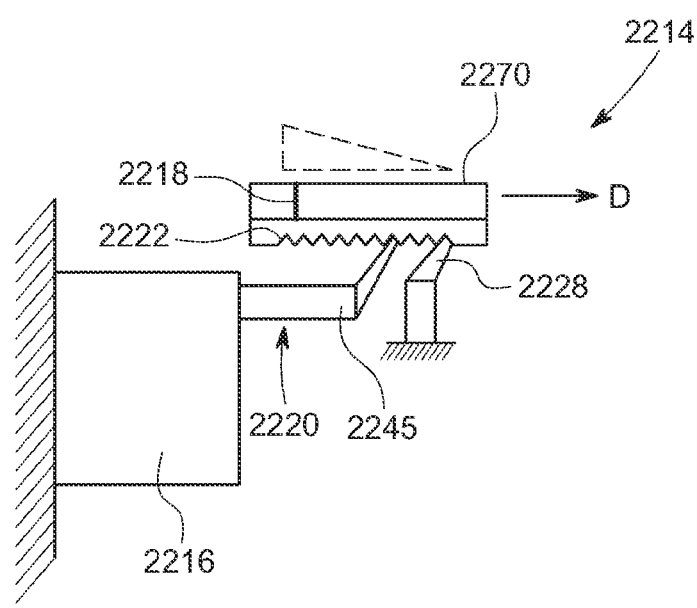
FIG. 22 is a schematic side view of a device for recording a reprocessing procedure according to another exemplary embodiment of the present disclosure.

Referring now to FIG. 22, a schematic view of one embodiment of a reprocessing recording device 2214 with a linear ratcheting mechanism 2220 and associated indicator 2218 is shown. The embodiment of FIG. 22 is shown implemented with a wax motor 2216 temperature-responsive state-change element, but as noted above, any other temperature-responsive state-change element could be used. The wax motor 2216 includes a drive pawl 2245 engaged with a rack 2270 that comprises ratchet teeth 2222. A locking pawl 2228 is biased in engagement with the ratchet teeth 2222 by any of the configurations discussed elsewhere herein. The rack 2270 includes the indicator 2218 which, in the device of FIG. 22, is a line or other pointer indicator. However, any of the other configurations of indicia disclosed elsewhere herein can be used with the device of FIG. 22.

Based on a temperature excursion associated with, e.g., exposure to a reprocessing procedure, the wax motor 2216 extends the drive pawl 2245 to advance the rack 2270 in direction D. Upon return to initial temperature conditions, e.g., conclusion of a reprocessing cycle, the wax motor 2216 causes the drive pawl 2245 to retract. The locking pawl 2228 maintains the rack 2270 in the position to which it was advanced by the drive pawl 2245 as the drive pawl 2245 retracts. The rack 2270 and associated indicator 2218 thereby advance based on the occurrence of temperature excursions substantially as discussed above in connection with the recording devices 2214 and 2214.

In some embodiments, user-accessible storage devices can be or include electronic circuitry that provides an electronic indication of the number of reprocessing cycles to which the instrument has been, or can be, subjected. Use of electronics and electrical sensors on the instrument to detect temperature cycles or otherwise recognize a cleaning or sterilization cycle involves certain challenges that exemplary embodiments of the present disclosure seek to address. For example, if the instrument is configured for use with a computer-assisted surgical system, the instrument is normally disconnected from the system and power source prior to reprocessing, and no source of power is available to operate the electronics. Likewise, if the instrument is manually operated, the instrument may have no source of electrical power to operate the electronics during reprocessing. Additionally, some electrical componentry can be particularly susceptible to exposure to high temperatures, chemicals, humidity, or other conditions of a reprocessing procedure. For example, batteries can be sensitive to elevated or reduced temperatures, and temperature extremes can negatively impact battery life in terms of both electrical power and mechanical integrity.

The present disclosure contemplates electronic recording devices including both passive devices, which are powered only upon connection to an outside source of power, or active circuits, which include an integrated power source. Passive devices can include electronic user-accessible storage devices that can be operably coupled to mechanical recording devices according to the present disclosure, such as the reprocessing recording devices 1214 (FIGS. 17, 18A, and 18B), 1914 (FIG. 19), and 2214 (FIG. 22). In addition, such devices can be used without limitation on any of the use recording devices, reprocessing recording devices, and instruments including both use recording devices (such as those disclosed in connection with FIGS. 1-15) and reprocessing recording devices disclosed herein.

One example of a passive electronic user-accessible storage device is one in which a moveable electrical contact is coupled to generate contact between a plurality of unique patterns of conductive traces as the electrical contact moves. A passive integrated circuit can be operably coupled with the contacts and can be configured to assign a specific address, number, or other unique identifier to each of a plurality of unique combinations of conductive traces contacted by the electrical contact. In this way, the movable electrical contact serves as the counter mechanism by virtue of its electrical connection to various combinations of conductive traces, while the integrated circuit provides an indication of the number of reprocessing procedures to which the instrument has been, or can be, subjected. Such electronic arrangements can be used in addition to, or in place of, visual indicators.

Figure 23A:
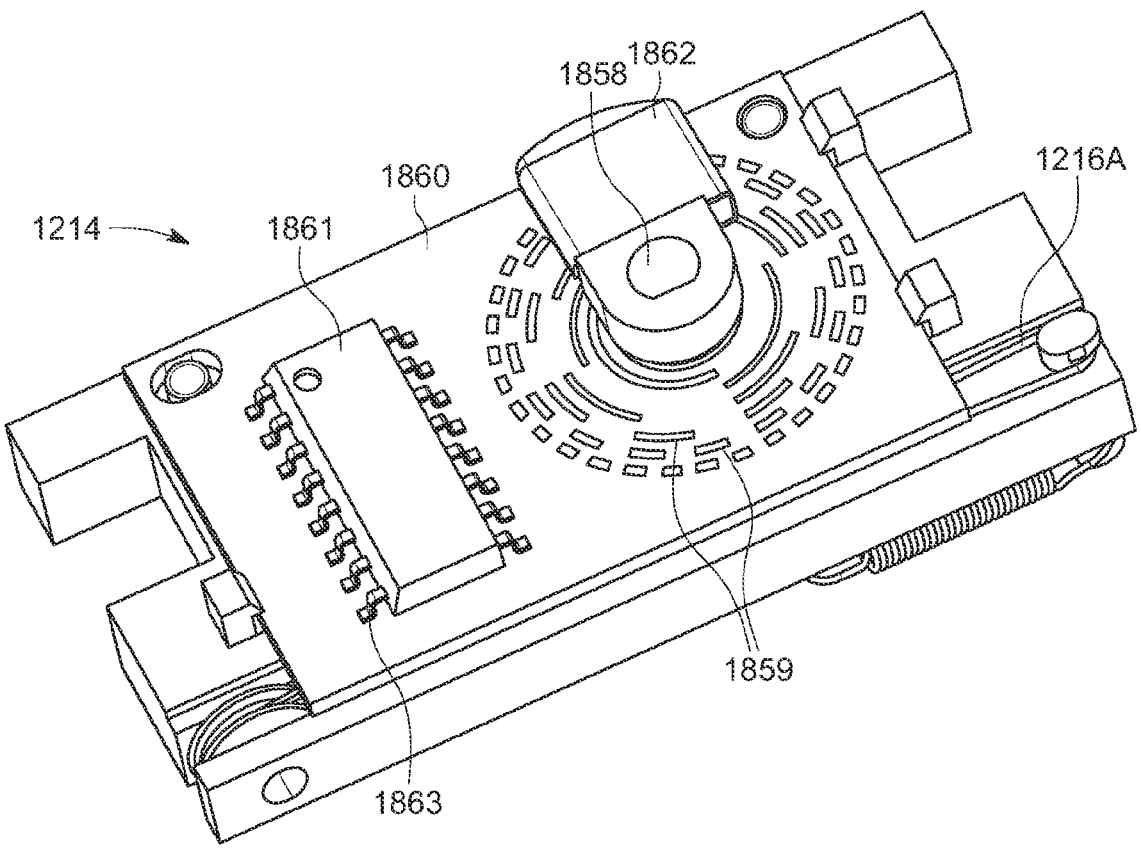
FIG. 23A is a perspective view of a device to store and provide information regarding reprocessing procedure to which an instrument is subjected according to an exemplary embodiment of the present disclosure.
Figure 23B:
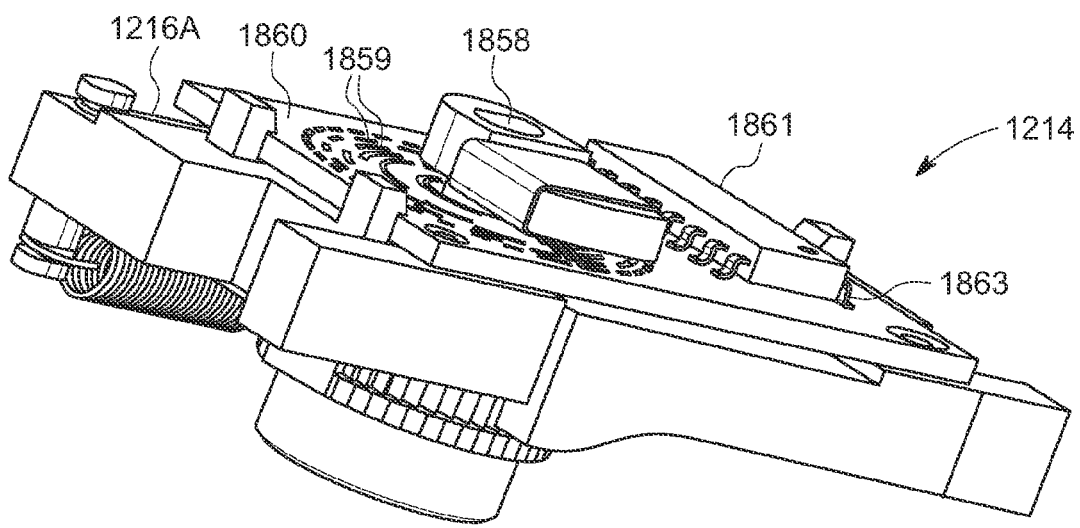
FIG. 23B is another perspective view of the device shown in FIG. 23A.

For example, referring now to FIGS. 23A and 23B, various perspective views of the recording device 1214 of FIGS. 17, 18A, and 18B are shown. The views of FIGS. 23A and 23B show the side of the recording device 1214 opposite to the plan views of FIGS. 18A and 18B. While the passive electronic recording device is shown in connection with the recording device 1214 discussed in connection with FIGS. 17, 18A, and 18B, such electronic recording devices can be used in conjunction with any of the other mechanical recording device embodiments disclosed herein.

Passive electronic recording devices according to the disclosure can include electrical components that are coupled with mechanical components of mechanical recording devices, components similar to those discussed above in connection with FIGS. 17, 18A, and 18B. In the embodiment of FIGS. 23A and 23B, the ratchet wheel 1221 (FIG. 2) is coupled with a shaft 1858 that extends through a printed circuit board (PCB) 1860. The PCB 1860 includes a plurality of conductive traces 1859 circumferentially inscribed as arc segments around the shaft 1858. The conductive traces 1859 are conductively coupled with various pins 1863 of an integrated circuit (IC) 1861, e.g., by conductive paths (not shown) of the PCB between the PCB pins 1863 and the conductive traces 1859. A contact arm 1862 is coupled to and extends radially outward from the shaft 1858. Rotation of the shaft 1858 (e.g., due to operation of the ratcheting mechanism 1220 (FIGS. 17, 18A, and 18B) based on temperature excursions) causes the contact arm 1862 to move, creating a conductive path between various conductive traces 1859 as it sweeps around the PCB. Thus, as a result of exposure of the recording device 1214 to temperature excursions, such as elevated or reduced temperatures associated with reprocessing procedures such as washing (e.g., ultrasonic washing) or autoclave cycles, the contact arm 1862 rotates around the PCB.

The IC 1861 can assign a unique identifier, such as an integer number, with the position of the moveable contact arm 1862 based on the particular combination of conductive traces 1859 that are in conductive contact via the moveable contact arm 1862. Upon connection of the instrument to a powered electronic device, such as an electrical interface at a manipulator arm of a teleoperated, computer-assisted surgical system or other interface, the unique identifier assigned by the IC 1861 can be read and, for example, displayed on a display, which may be associated with a surgical system, and/or entered into a database (or other processor/controller) of instrument information used to track reprocessing and other uses of instruments.

As an alternative to the conductive traces 1859 and movable contact arm 1862 discussed in connection with FIGS. 23A and 23B, other embodiments of passive electronic recording devices can include an analog configuration. For example, the passive electronic recording device can be or include a device similar to a potentiometer, with a resistive pad on the PCB 1860 and a moveable contact arm with a sweeper in contact with the resistive pad. Resistance between the sweeper and the conductive pad varies depending on the rotational position of the sweeper. In such an embodiment, the IC 1861 can exhibit capability to convert resistance detected between the conductive pad and the sweeper to a discrete value associated with a number of exposures to reprocessing procedures. As discussed above, when operably connected to a surgical system, the IC can provide information about the number of reprocessing procedures to which the device has been subjected, e.g., through a user interface of the surgical system. Other alternative components and configurations of passive electronic recording devices can include, for example, position-sensitive magnetic or inductive couplings, optical encoders, or other devices.

While the passive electronic recording device discussed in connection with FIGS. 23A and 23B is shown used in conjunction with the visual-type recording device of FIGS. 17, 18A, and 18B, a person of ordinary skill in the art will readily appreciate that the passive electronic recording device of FIGS. 23A and 23B can be used as a stand-alone device, or in combination with other recording devices described herein, such as the recording device 1414 disclosed in connection with FIG. 19, the recording device 2214 (FIG. 22), or other devices, such as, without limitation, the use recording devices disclosed in connection with FIGS. 1-15.

As discussed above, exposure to extreme temperatures can negatively impact lifetimes of batteries. In particular, when batteries are required to operate under extreme temperature conditions for extended times, the life of the battery and the mechanical integrity of the battery packaging can potentially be compromised. Accordingly, devices according to the disclosure can include voltage sources such as batteries, energy harvesting devices, or other voltage sources in a configuration that mitigates degradation of the voltage source.

Figure 24:
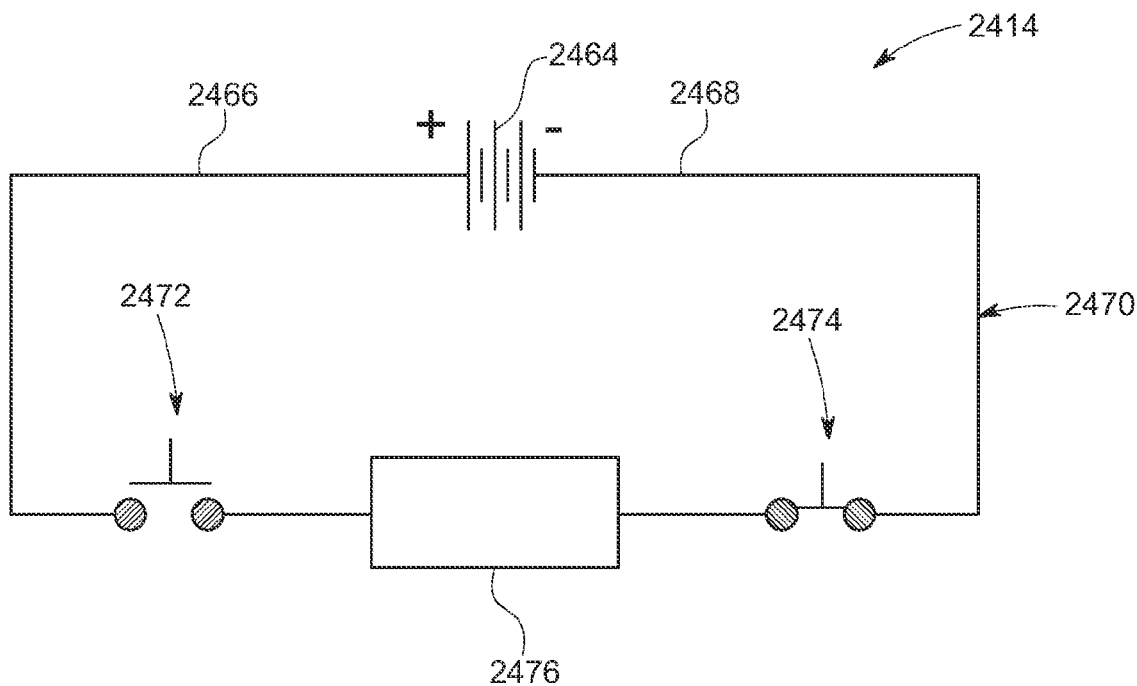
FIG. 24 is a schematic circuit diagram of a device to store and provide information regarding a reprocessing procedure of an instrument according to another exemplary embodiment of (the present disclosure.

Referring now to FIG. 24, a circuit diagram of an active electronic reprocessing recording device 2414 is shown. The active electronic reprocessing recording device 2414 is configured to enable use of batteries in an instrument by limiting the amount of time the batteries are required to be operational during a reprocessing cycle, and by only operating the batteries in a temperature range where battery performance is not seriously compromised.

The reprocessing recording device 2414 includes a voltage source comprising a battery 2464 with a positive terminal 2466 and a negative terminal 2468 forming a circuit 2470. Two temperature-operated switches, a first switch 2472 and a second switch 2474, are positioned in the circuit 2470. First switch 2472 is a normally open switch that closes at a first temperature. Second switch 2474 is a normally closed switch that opens at a second temperature, higher than the first temperature.

Positioned between the first switch 2472 and second switch 2474 is an memory device 2476, which may be in the form of an integrated circuit that records (e.g., on non-volatile memory) electronic data indicative of a number of times a voltage is applied to the memory device 2476.

Under operating conditions such as those to which the instrument is subjected during use, the first switch 2472 remains open, while the second switch 2474 remains closed.

The circuit 2470 is in an open condition, and the battery 2464 generates no current flow. The first switch 2472 can be configured to close at a specified first elevated temperature below a maximum temperature associated with a reprocessing cycle, such as, for example, 80° C. When the temperature reaches the first elevated temperature, the first switch 2472 closes, completing the circuit 2470. The voltage potential across the positive 2466 and negative 2468 terminals of the battery is thereby applied to the memory device 2476. The memory device 2476 records the instance of applied voltage, e.g., by incrementing a record held on non-volatile memory. The second switch 2474 can be configured to open at a specified second elevated temperature above the first elevated temperature but below a temperature at which the recording device 2414 will be held for a significant period of time. For example, if the first switch 2472 is configured to close at 80° C., the second switch 2474 can be configured to open at 90° C. Once the temperature reaches the specified second elevated temperature, the second switch 2474 opens, thereby opening the circuit 2470 for the duration of the reprocessing cycle, which may be carried out at a temperature above the specified second temperature, such as, for example, 121° C.

Because the circuit 2470 is only closed and the battery 2464 operational for a relatively short period of time, e.g., during the transition from a temperature during use of the instrument to an elevated temperature associated with a reprocessing cycle, the battery 2464 is only required to operate for a short period of time at the predetermined (e.g., elevated) temperatures. The battery life is thereby increased as compared to a battery required to operate throughout the entirety of a reprocessing procedure. That is, the configuration of the circuit 2470 reduces (e.g., minimizes) the time for which the battery is required to operate under heightened (or reduced) temperature conditions. While the circuit 2470 is shown in an arrangement for recording reprocessing procedures, the first and second temperature-operated switches can be used in a similar manner to prolong battery life in any instrument or device exposed to high temperatures. Further, while the first switch 2472 and second switch 2474 are shown positioned on either side of the memory device 2476, any other arrangement of the first switch 2472 and the second switch 2474 is within the scope of the disclosure. For example, both the first switch 2472 and second switch 2474 could be positioned on a same leg of the circuit, i.e., both switches in series between the positive or negative terminals of the battery 2464 and the memory device 2476, or can be rearranged in any order in which closing the first switch 2472 closes the circuit 2470 and opening the second switch 2474 opens the circuit.

Information stored in the non-volatile memory of the memory device 2476 can be retrieved from the memory device when the instrument is in use or otherwise coupled to a powered surgical system, such as a teleoperated, computer-assisted surgical system or other interface. Alternatively or additionally, the instrument could include an LCD, e-ink, or other electronic display that would show the number of reprocessing procedures the instrument has been subjected to and/or the remaining number of reprocessing procedures to which the instrument can be subjected. To maintain the conservation of battery life provided by the arrangement of the circuit 2470, the display could be operably coupled to the battery by, e.g., a user-actuated pushbutton such that the display would only operate when the pushbutton was depressed. Additionally or alternatively, a temperature-operated switch similar to switches 2472 and 2474 discussed above could be configured to remove power from the display when a certain elevated temperature is reached.

Some embodiments of active electronic recording devices can include voltage sources that operate based on conditions occurring during reprocessing procedures, such as application of heat and associated elevated temperatures, mechanical energy such as ultrasonic vibration, application of pressure, or other conditions. For example, an active electronic recording device can include a voltage source that can be or include and energy harvesting device that converts thermal energy, pressure, and/or mechanical energy to an electrical current.

Figure 25:
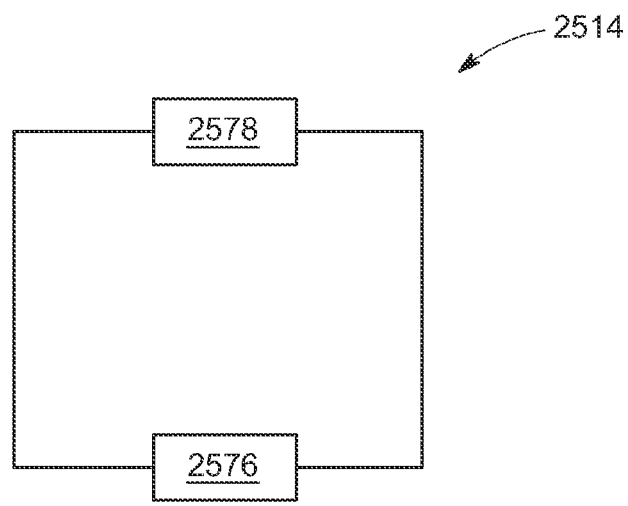
FIG. 25 is a block diagram of a device to store and provide information regarding a reprocessing procedure to which an instrument is subjected according to yet another exemplary embodiment of the present disclosure.

Referring now to FIG. 25, a block diagram of an embodiment of an environment exposure recording device 2514 including an energy harvesting device 2578 is shown. The energy harvesting device 2578 can be or include, for example, a piezoelectric element that generates an electrical current based on mechanical vibrations, or a thermocouple or plurality of thermocouples (e.g., a thermopile) device that generates an electrical current in response to exposure to a temperature differential, or another type of energy harvesting device. The energy harvesting device 2578 can be operably coupled to an memory device 2576 (similar to the memory device 1976 discussed in connection with FIG. 24).

In the exemplary embodiment of FIG. 25, the energy harvesting device 2578 is a piezo-type energy harvesting device. Upon exposure to vibration, such as ultrasonic vibration, the energy harvesting device 2578 generates an electrical current that, applied to the memory device 2576, causes the memory device 2576 to increment a record of the event on non-volatile memory, substantially as discussed in connection with FIG. 24.

Other embodiments can include an energy harvesting device 2578 that operates based on exposure to a temperature gradient. For example, the energy harvesting device can be or include a thermocouple or thermopile, or another temperature-actuated device. Upon exposure to elevated temperature conditions associated with a reprocessing procedure, the energy harvesting device 2578 generates an electrical current that causes the memory device 2576 to increment a record of the event on non-volatile memory.

Temperature-responsive state-change elements such as those discussed above can additionally be operably coupled with components configured to disable an instrument that is not designed to withstand conditions associated with an autoclave procedure. For example, referring now to FIG. 26A, a wax motor 2616 is coupled with a locking device 2648. The locking device 2648 includes gear teeth 2650 configured to engage with a gear 2649 of a rotational instrument input, such as an input disc 2651 of an instrument configured for use with a computer-assisted, tele-operated surgical system. FIG. 26B shows a side view of the system of FIG. 26A. The locking device 2648 includes locking pawls 2654 that can engage with complementary pawls 2656 on a housing or other fixed portion of the instrument.

Upon exposure to elevated temperature conditions, such as during a washing procedure, autoclave cycle, or other reprocessing procedure, the wax motor 2616 pushes the locking device 2648 into contact with the gears 2649 of the input disc 2651, and the locking pawls 2654 engage the complementary pawls 2656, thereby preventing use of the instrument. While a wax motor is shown in the device of FIGS. 26A and 26B, a nitinol wire, bimetallic component, or other temperature-responsive device could be used in a similar manner to immobilize the instrument and render it unusable.

Figure 26A:
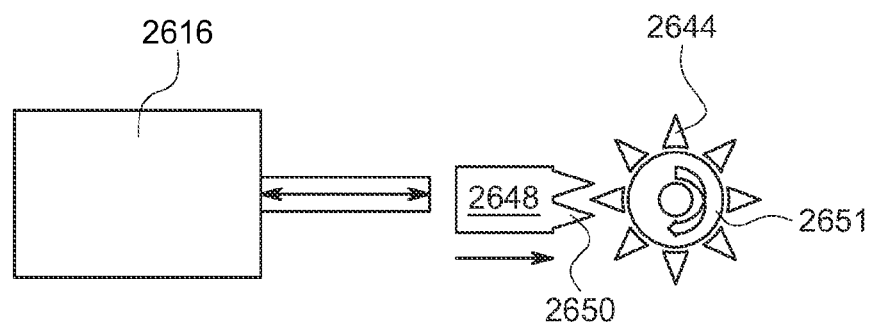
FIG. 26A is a schematic plan view of a lockout device according to an exemplary embodiment of the present disclosure.
Figure 26B:
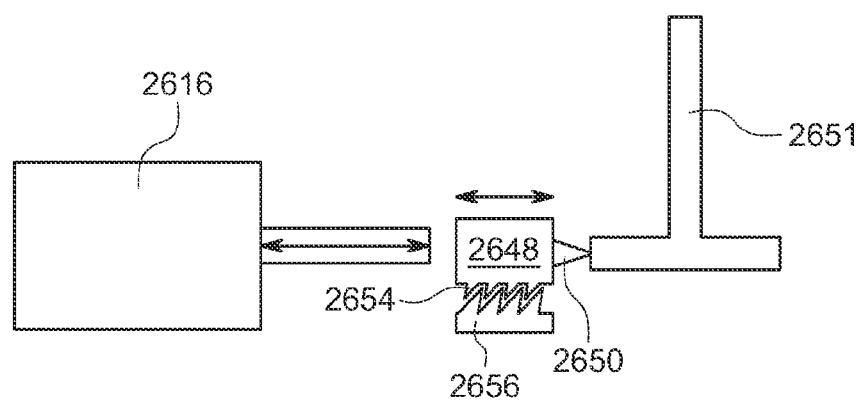
FIG. 26B is a schematic side view of the lockout device of FIG. 26A.

Further, locking device 2648 of the device of FIGS. 26A and 26B can be used with any of the devices disclosed elsewhere herein to render a device unusable if it reaches a specified number of reprocessing procedures. For example, a locking device similar to locking device 2648 could be integrated with a visual indicator, such that when the visual indicator reaches a position associated with a total number of reprocessing cycles having taken place, the locking device is in position to lock out use of the instrument, as discussed above in the embodiment of FIGS. 26A and 26B. Alternatively, systems like those described in connection with FIGS. 26A and 26B can be used in disposable instruments not designed to withstand autoclaving such that the instrument is immediately disabled on a first exposure to autoclave conditions, or any specified temperature threshold.

Referring now to FIGS. 27A-27E, another exemplary embodiment of a recording device 2714 including a counter mechanism 2713 is shown. The recording device 2714 includes a visual indicator 2718 that includes visual indicia in the form of integer numbers to be exposed through an aperture of an instrument housing, as shown in FIGS. 27A-27E, or any other type or configuration of indicia as discussed elsewhere herein. The visual indicator 2718 is operably coupled with a toothed wheel 2780. In the device of FIGS. 27A-27E, the visual indicator 2718 is coaxial with the toothed wheel 2780, but in alternative configurations, the toothed wheel 2780 can be coupled to the visual indicator 2718 by drive components such as gears, belts and pulleys, or other mechanisms.

The toothed wheel 2780 includes a first set of teeth 2782 on a first surface 2783 of the toothed wheel 2780 and a second set of teeth 2784 on a second surface 2785 of the toothed wheel 2780. The first teeth 2782 each feature a radially outward facing ramped surface 2786 and the second teeth 2784 each feature a radially inward facing ramped surface 2787. A plunger 2788 includes a first arm 2789 positioned adjacent the first teeth 2782 and a second arm 2790 positioned adjacent the second teeth 2784.

The plunger 2788 is operably coupled to a temperature-responsive state-change element (not shown in the view of FIGS. 27A-27E) that imparts reciprocating linear motion to the plunger 2788, such as a wax motor similar to the wax motor 1416 discussed in connection with FIG. 19. However, the temperature-responsive element can be or include any of the state-change components and devices discussed elsewhere herein, such as, but not limited to, shape-memory alloy components, wax motors or other bladder- or reservoir-type devices, bimetallic components, pressure-responsive actuators, or any other device that can be configured to provide reciprocating linear motion.

Figure 27A:
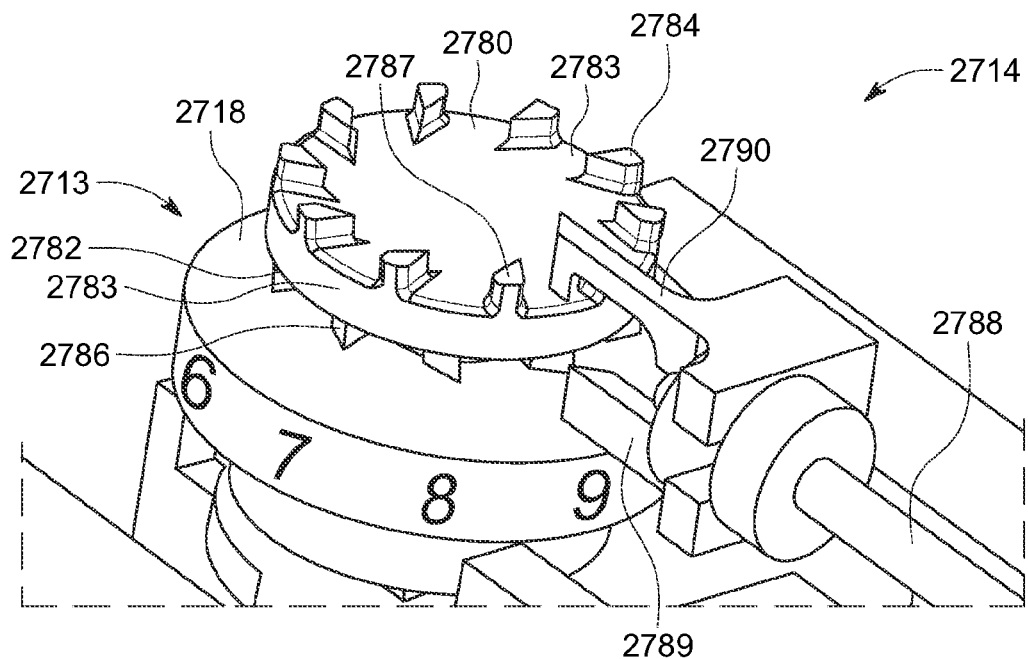
FIGS. 27A-27E are perspective detailed views of a device to store and provide information regarding a reprocessing procedure to which an instrument is subjected according to yet another exemplary embodiment of the present disclosure.
Figure 27B:
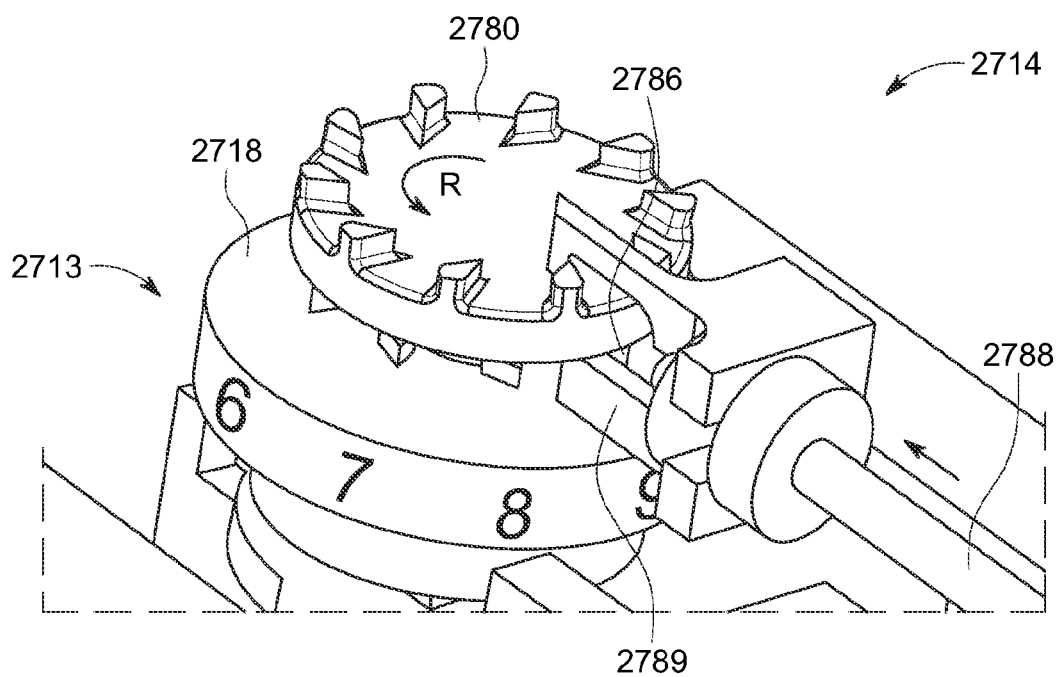
Figure 27C:
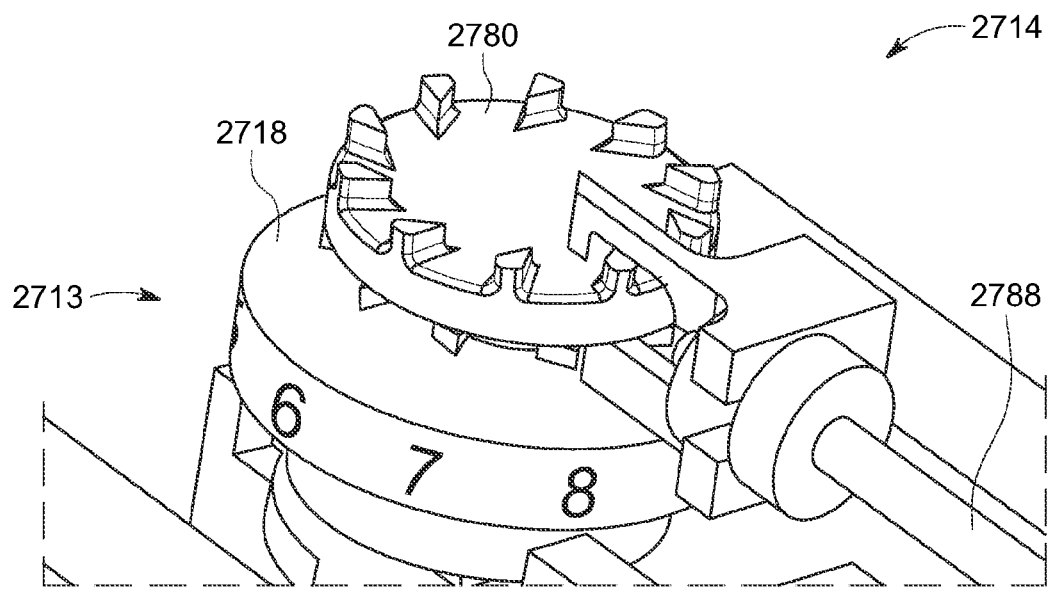

Referring now to FIG. 27A, the reprocessing recording device 2714 is shown in an initial position with the plunger 2788 retracted from the toothed wheel 2780. Upon exposure of the device to elevated temperature conditions (e.g., associated with a reprocessing procedure) sufficient to actuate the temperature-responsive element, the temperature-responsive element causes the plunger 2788 to advance toward the toothed wheel 2780. As the plunger 2788 advances toward the toothed wheel 2780, the first arm 2789 contacts the radially outward facing ramped surface 2786 of a tooth of the first set of teeth 2782, as shown in FIG. 27B, causing rotation of the toothed wheel in direction R to the state shown in FIG. 27C.

Figure 27D:
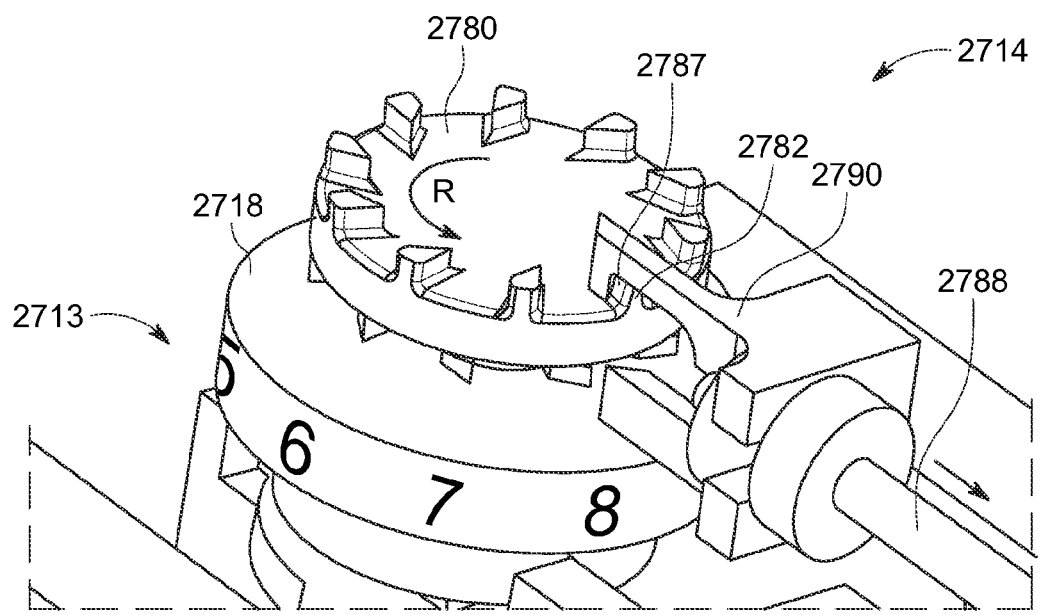
Figure 27E:
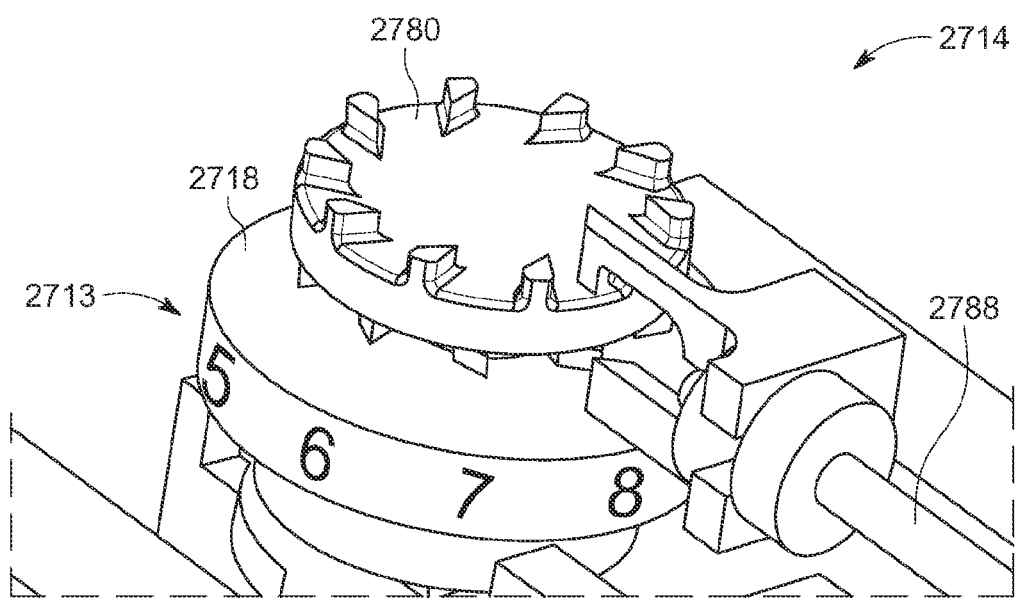

Upon cessation of the elevated temperature conditions, the temperature-responsive element causes the plunger 2788 to begin retracting from the toothed wheel 2780 (i.e., the plunger 2788 begins returning to the position shown in FIG. 27A) as shown in FIG. 27D. As the plunger 2788 retracts, the second arm 2790 contacts radially-inward facing ramped surface 2787 of a tooth of the first set of teeth 2782, causing further rotation of the toothed wheel 2780 in direction R. The plunger 2788 retracts fully to the position shown in FIG. 27E, and the recording device 2714 has completed recording of the temperature excursion to the elevated temperature.

The total angular rotation of the toothed wheel 2780 through the sequence shown in FIGS. 27A-27E is the same as the angular separation of the indicia of the visual indicator 2718, such that after one sequence as shown in FIGS. 27A-27E, the indicia visible decrements (or increments depending on the arrangement) by a single integer. As discussed elsewhere herein, various other configurations of indicia are within the scope of the disclosure, such as graph-type indicators, color-based indicators, non-consecutive integer sequences, and other arrangements.

While the embodiment of FIGS. 27A-27E is described as having a temperature-responsive state-change element, any state-change elements discussed above can be used without departing from the scope of the disclosure, such as, but not limited to, pressure-responsive elements, vibration-responsive elements, or other state change elements that undergo a change in physical dimension, position, phase, or other characteristic under changes in environmental conditions.

Figure 28:
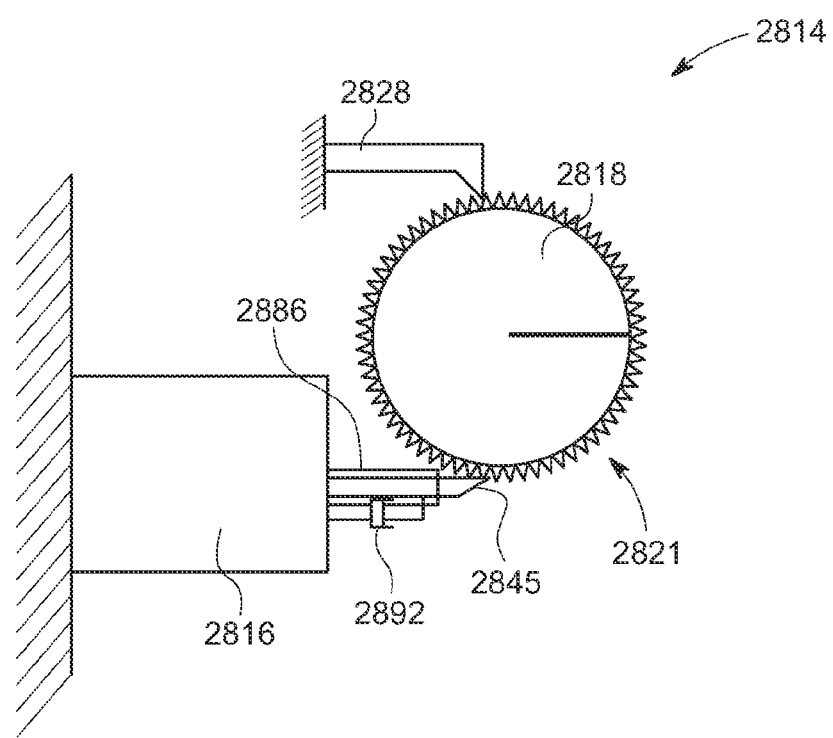
FIG. 28 is a schematic side view of another device to store and provide information regarding a reprocessing procedure to which an instrument is subjected according to yet another exemplary embodiment of the present disclosure.

FIG. 28 shows a schematic view of another embodiment of a reprocessing recording device that includes a pressure-responsive state-change element instead of a temperature-responsive state change element. The reprocessing recording device 2814 includes a pressure-responsive state-change element 2816 which can be or include, for example, a pressure-responsive actuator including a diaphragm, a piston-cylinder device, or other type of pressure-responsive element. The pressure-responsive state-change element 2816 can be operably coupled with a plunger 2886 that is coupled to a drive pawl 2845. The drive pawl 2845 is positioned adjacent a ratchet wheel 2821 such that extension of the plunger 2886 in response to actuation of the pressure-responsive element 2816 (e.g., due to pressure conditions above or below atmospheric pressure) causes rotation of the ratchet wheel 2821 in direction R. A locking pawl 2828 holds the ratchet wheel 2821 in the new rotational orientation as the plunger 2886 and drive pawl 2845 retract upon a return to atmospheric pressure. The ratchet wheel 2821 can include or be coupled to a visual indicator 2818 in any of the forms and configurations discussed herein.

As discussed above, some autoclave and other reprocessing procedures involve rapid cycles of pressure and/or temperature. Accordingly, the recording device 2814 can be configured such that the response time of the pressure-responsive element 2816 is such that it actuates once for an entire autoclave or other reprocessing procedure. For example, the recording device 2814 can include a damper 2892 configured to mechanically slow the response of the pressure-responsive element 2816 to the desired degree. Other approaches to tailor the response time of the pressure-responsive element 2816 can include thermally insulating the pressure responsive element, metering a flow rate of environmental fluids (air, steam, etc.) to the pressure responsive element, or other approaches as would be apparent to one having skill in the art.

In some situations, it may be desired to clearly indicate to a user via a use counting device or a reprocessing recording device that the instrument has been subjected to the maximum permissible number of reprocessing cycles. In some devices herein, such as use recording devices and reprocessing recording devices, the devices can be configured to provide an indication qualitatively different from the count indication once the maximum permissible number of uses and/or reprocessing cycles has been met. For example, the use recording device or reprocessing recording device, or both, can optionally include a component such as an indicator flag that appears when the maximum permissible number of uses or reprocessing cycles are met. In devices in which the recording device indicates the number of uses or reprocessing cycles via visual indicia, the indicator flag can optionally be configured to obscure the visual indicia and clearly indicate to the user that the number of permissible uses or reprocessing cycles has been met and the instrument cannot acceptably be subjected to any further use or reprocessing cycles. The indicator flag can be configured with a warning message, such as words or indicia indicating that the instrument cannot permissibly be subjected to further use or reprocessing cycles, universal warning indicia such as the color red, or other features.

Some instruments or systems may not be configured to positively prevent continued use of the instrument once the maximum permissible number of uses or reprocessing cycles has been met. Thus, the warning that the maximum permissible number of uses or reprocessing cycles has been met may not be heeded and use of the instrument and/or subject the instrument to reprocessing cycles may continue, contrary to the applicable recommendations and/or regulations. In some cases, it may be desirable to track uses or reprocessing cycles occurring after the maximum permissible number, even in instruments that include an indicator flag obscuring the visual indicia.

Figure 29:
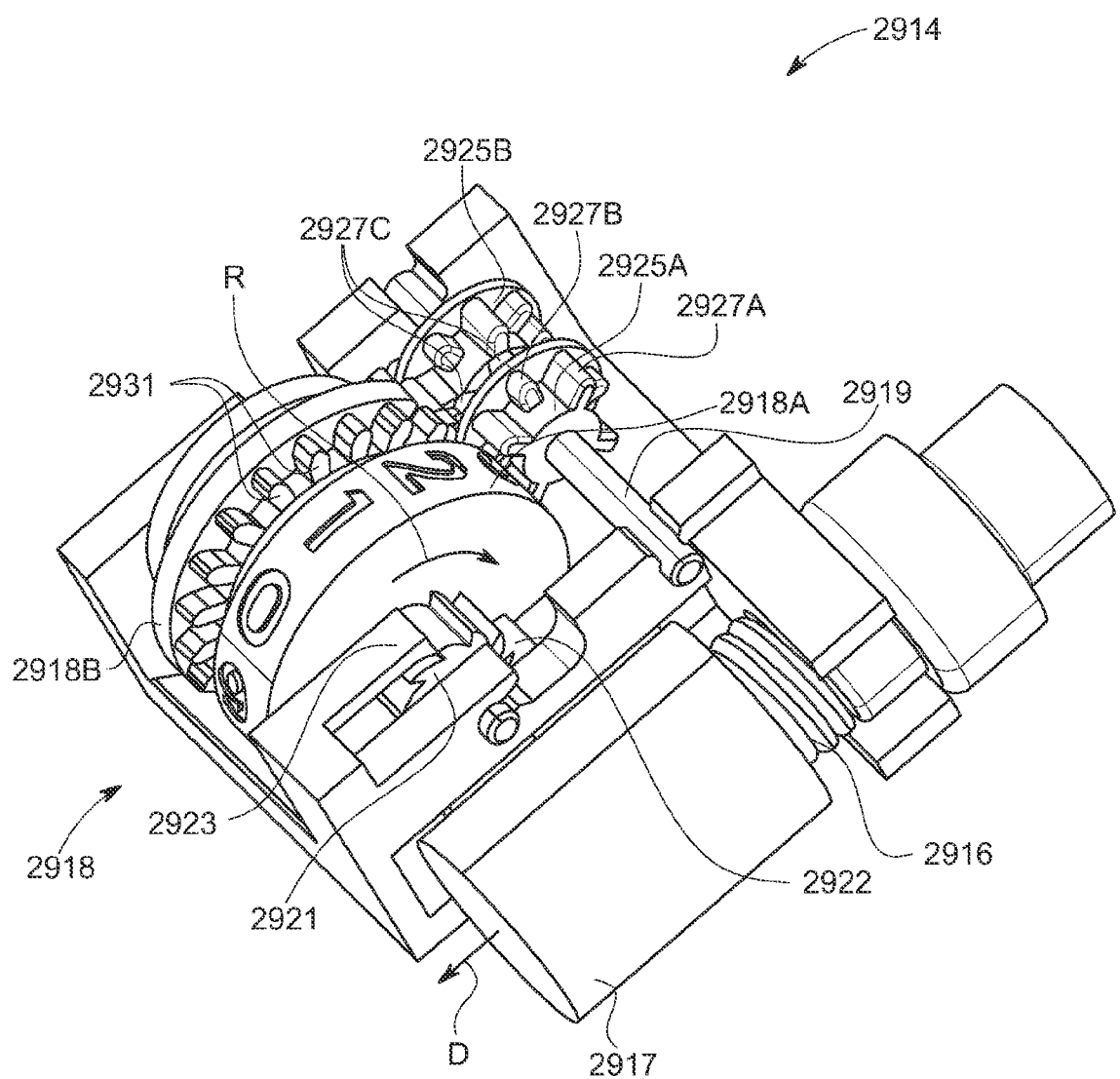
FIG. 29 is a perspective view of a device for recording a reprocessing procedure to which and instrument is subjected according to another exemplary embodiment of the present disclosure.

Referring now to FIGS. 29-32, another embodiment of a reprocessing recording device 2914 is shown. While the device of FIGS. 29-32 is a reprocessing recording device, various features, components, and arrangements of the reprocessing recording device 2914 are also applicable to use recording devices disclosed herein. The reprocessing recording device 2914 includes various features similar to those disclosed in connection with the recording devices disclosed in connection with FIGS. 16-28, such as a state change element 2916 and a counter mechanism with a visual indicator 2918. In the device of FIG. 29, the state change element 2916 comprises a wax motor. However, other state change elements, such as, without limitation, other temperature and/or pressure responsive elements as discussed herein, can optionally be used in connection with the device 2914.

In various devices of the embodiments of FIGS. 1-28, a visual indicator comprises a single component including visual indicia to indicate to the user the number of remaining reprocessing cycles to which the instrument can be exposed, or alternatively the number of cycles to which the instrument has already been exposed. In some devices, the visual indicia can include multiple components to indicate different numerical place values. Said another way, two or more counter mechanisms can be used with differing numbers of environment exposures or uses that trigger the movement to the next visual indicator. For example, a recording device of the present disclosure can optionally include separate components with separate indicia for counting single uses, tens of reprocessing cycles, hundreds of reprocessing cycles, etc. The recording device 2914 shown in FIGS. 29 and 30 includes a visual indicator 2918 comprising a ones counter wheel 2918A and a tens counter wheel 2918B. The ones counter wheel 2918A can be provided with indicia indicating individual reprocessing cycles, and the tens counter wheel 2918B can be provided with indicia indicating tens of reprocessing cycles. For example, the ones counter wheel 2918A can display cycles 0-9, while the tens counter wheel 2918B can display cycles 0-2, 0-3, 0-4, up to 0-9, etc., depending on the total number of cycles to which the instrument can permissibly be exposed. As with other embodiments disclosed herein, indicia of the ones counter wheel 2918A and tens counter wheel 2918B can be configured to be exposed through an aperture in a housing of the instrument (not shown). While the device of FIGS. 29 and 30 includes a ones counter and tens counter, other embodiments can include additional counters, such as hundreds, thousands, etc. depending on the total number of uses and/or reprocessing cycles permissible. Additionally, counters need not utilize base-ten numbering, and counters employing other base numbers, hexadecimal numbering, or other numbering systems are within the scope of the disclosure. Using separate counters representing different positional numbering places can contribute to an overall smaller device for a given total number of uses or reprocessing cycles and/or can facilitate a greater number of uses or reprocessing cycles being recorded.

In an embodiment, the ones counter wheel 2918A and tens counter wheel 2918B are mechanically coupled in a manner similar to a mechanical odometer, a tally counter, or other similar mechanism. That is, rotation of the ones counter wheel 2918A and tens counter wheel 2918B are coupled such that for a full rotation of the ones counter wheel 2918A, the tens counter wheel 2918B increments (i.e., displays a greater or lesser indicia, depending on whether the counter is counting up to a maximum or counting down to zero) once. For example, the ones counter wheel 2918A and tens counter wheel 2918B are engaged with first lobed wheel 2925A and second lobed wheel 2925B rotatably held by a countershaft 2919. The first lobed wheel 2925A and second lobed wheel 2925B are rotatable independently from one another. For example, both the first lobed wheel 2925A and the second lobed wheel 2925B can be freely rotatable on the countershaft 2919. The first lobed wheel 2925A and second lobed wheel 2925B are provided with engagement lobes configured to engage various features of the ones counter wheel 2918A and tens counter wheel 2918B, as will be discussed further in relation to operation of the recording device 2914.

Figure 30:
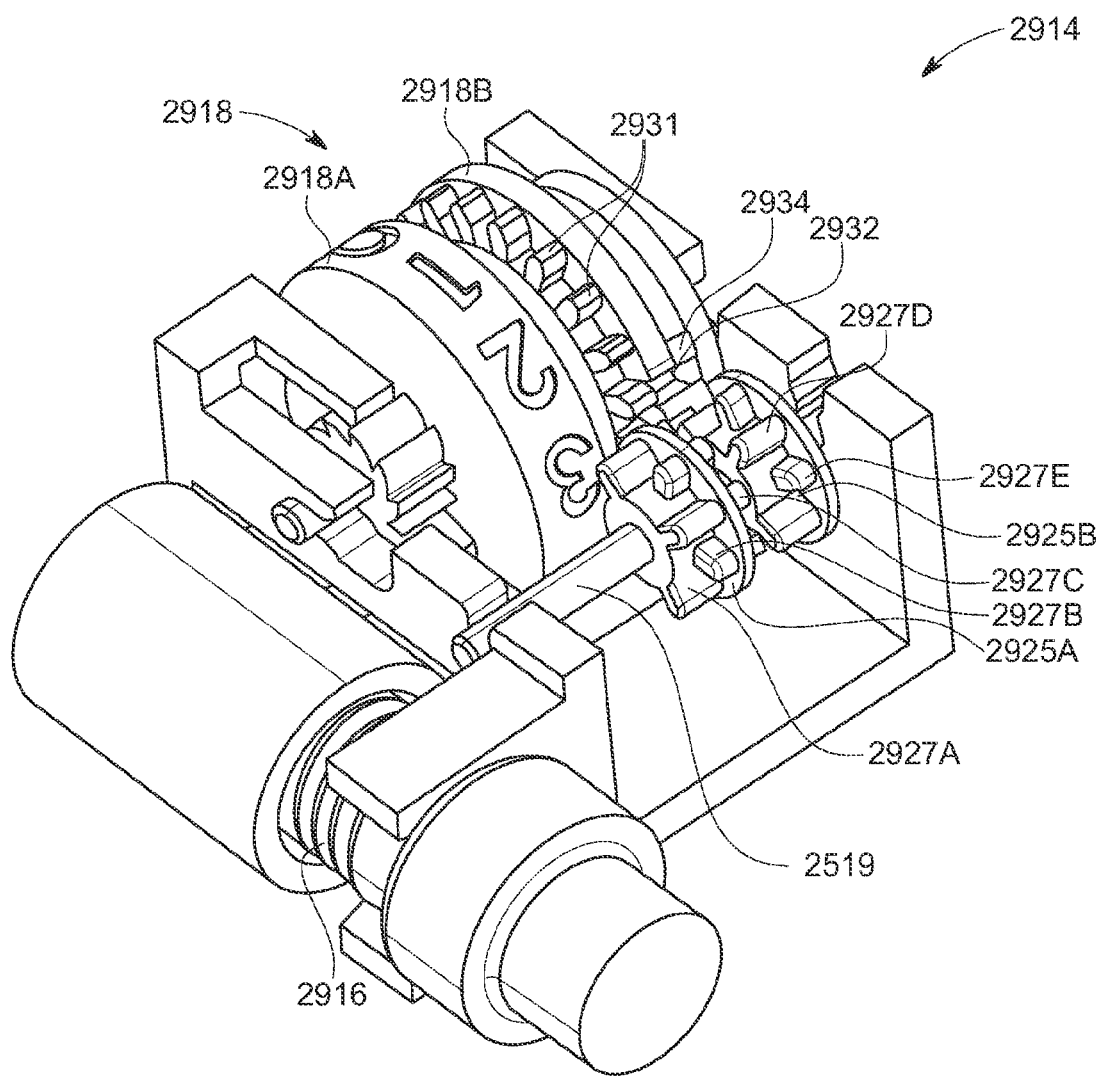
FIG. 30 is another perspective view of the device of FIG. 29.
Figure 31:
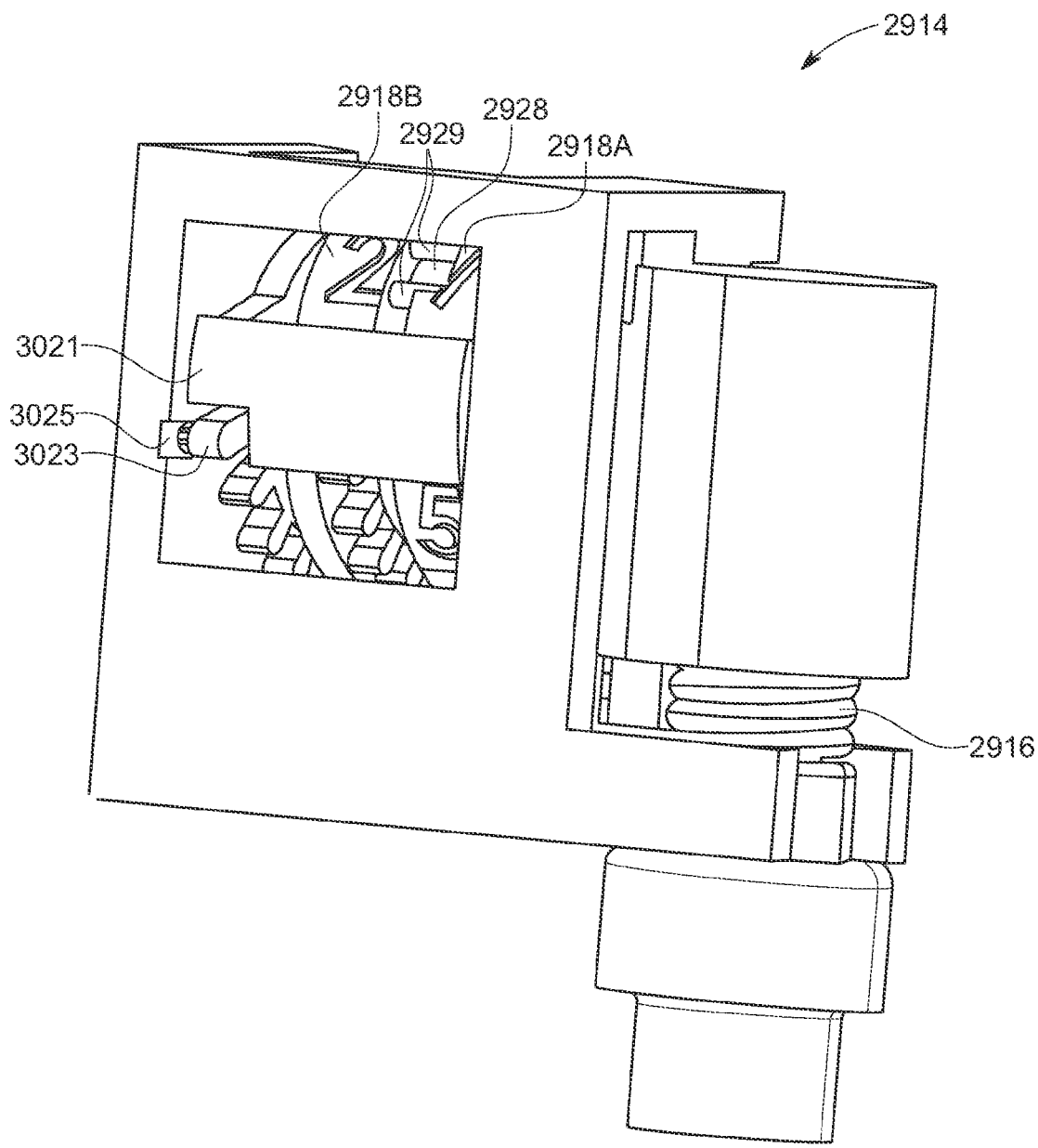
FIG. 31 is yet another perspective view of the device of FIG. 29.

As discussed above, some embodiments of use recording device and/or reprocessing recording devices may include indicator flags that indicate that the maximum permissible number of uses or reprocessing cycles has been met. Referring now to FIG. 31, a perspective view of the recording device 2914 shows a side of the recording device 2914 generally opposite the side primarily shown in the views of FIGS. 29 and 30. In the view of FIG. 31, an indicator flag 3021 is shown in a deployed position, i.e., a position in which it covers the user's view of the ones counter wheel 2918A and tens counter wheel 2918B. The indicator flag 3021 can be configured to be reliably retained in the deployed position such that the indicator flag 3021 does not inadvertently shift from the deployed position during handling. For example, in the device 2914, the indicator flag 3021 includes a resilient retaining member 3023 that engages a detent 3025 to hold the indicator flag 3021 in the deployed position.

In use, exposure to elevated temperatures, such as temperatures associated with a reprocessing cycle or a portion thereof, actuate the state change element 2916. In the device 2914, the state change element 2916 is a wax motor with a reservoir of material that expands upon exposure to elevated temperature. Referring again to FIGS. 29 and 30, the ones counter wheel 2918A includes a ratchet wheel 2921 engaged with a drive pawl 2922 and an anti-backup pawl 2923. The state change element 2916 includes a movable portion 2917 that is mechanically coupled to the drive pawl 2922 engaged with the ratchet wheel 2921. Actuation of the state change element 2916 causes the movable portion 2917 of the state change element to translate in direction D, causing the drive pawl 2922 to rotate the ones counter wheel 2918A in direction R, advancing the ones counter wheel 2918A, e.g., 1/10 of a rotation to reflect a single additional reprocessing cycle. Upon cessation of the elevated temperature conditions, the movable portion 2917 retracts, while the anti-backup pawl 2923 prevents reverse rotation of the ones counter wheel 2918A as the movable portion 2917 retracts. The state change element 2916 and the ones counter wheel 2918A can be configured so that exposure to a single reprocessing cycle results in the ones counter incrementing by one, i.e., reflecting one more reprocessing cycle having been carried out on the instrument or one fewer reprocessing cycles left to which the instrument can be exposed.

Interaction between the ones counter wheel 2918A, the tens counter wheel 2918B, and the first lobed wheel 2925A and second lobed wheel 2925B held by the countershaft 2912 is arranged to advance the tens counter wheel 2918B to display an additional ten reprocessing cycles for every full revolution of the ones counter wheel 2918A. As shown in FIG. 29, the first lobed wheel 2925A includes alternating long lobes 2927A and short lobes 2927B on a first side of the first lobed wheel 2925A. Referring now to FIG. 31, the ones counter wheel 2918A includes a notch 2928 configured to receive long lobes 2927A. Two protrusions 2929 on either side of the notch 2928 are arranged to engage the short lobes 2927B. The notch 2928 is positioned such that as the ones counter wheel 2918A rotates responsive to actuation of the state change element 2916 around a full rotation, one of the short lobes 2927B contacts a protrusion of the two protrusions 2929, causing the first lobed wheel 2925A to rotate counter to rotation of the ones counter wheel 2918A as one of the long lobes 2927A enters the notch 2928. Continued rotation of the ones counter wheel 2918A causes rotation of the first lobed wheel 2925A until the long lobe 2927A exits the notch 2928.

The first lobed wheel 2925A includes secondary short lobes 2927C constantly meshed with corresponding lobes 2931 on the tens counter wheel 2918B. Thus, as the first lobed wheel 2925A rotates in response to the notch 2928 of the ones counter wheel engaging with the first lobed wheel 2925A, the tens counter wheel 2918B rotates also. In the device of FIGS. 29-31, for every full rotation of the ones counter wheel 2918A, the tens counter wheel 2918B increments once.

The indicator flag 3021 can be actuated in response to movement of the tens counter wheel 2918B using an arrangement similar to the arrangement operably coupling the tens counter wheel 2918B and the ones counter wheel 2918A. With reference to FIG. 30, the tens counter wheel 2918B includes a notch 2932 and two protrusions 2934. The second lobed wheel 2925B is engaged with the tens counter wheel 2918B. As the tens counter wheel 2918B rotates responsive to rotation of the first lobed wheel 2925A, long lobes 2927D and short lobes 2927E of the second lobed wheel 2925B engage the notch 2932 and protrusions 2934 of the tens counter wheel 2918B. On condition of engagement of the notch 2932 and protrusions 2934 of the tens counter wheel with the long lobes 2927D and short lobes 2927E of the second lobed wheel 2925B rotation of the tens counter wheel 2918B drives rotation of the second lobed wheel 2925B.

Figure 32:
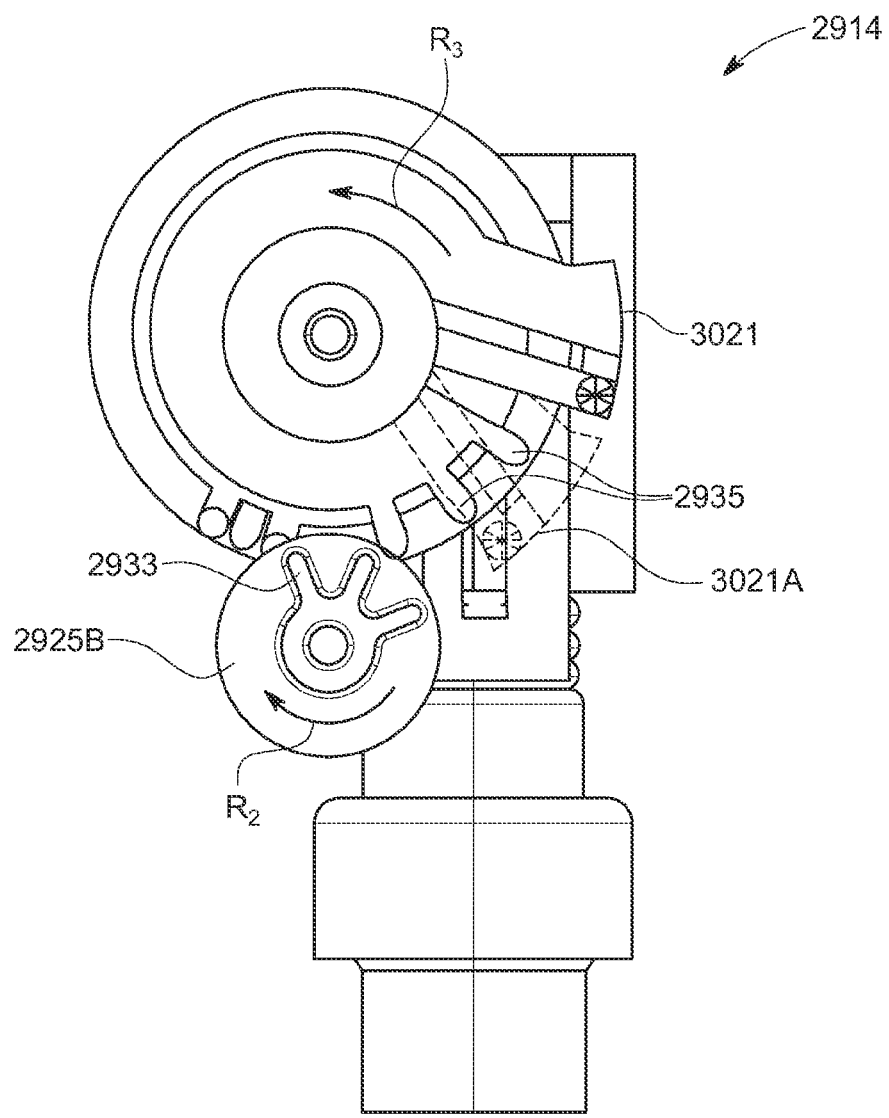
FIG. 32 is a partial side view of the device of FIG. 29.

Referring to FIG. 32, which shows a side cutaway view of the recording device 2914, the second lobed wheel 2925B includes a sector gear 2933 that intermeshes with teeth 2935 on the indicator flag 3021. Rotation of the second lobed wheel 2925B in direction $R_2$, e.g., in response to rotation of the tens counter wheel 2918B as discussed above, rotates the indicator flag 3021 in direction $R_3$ from a retracted position (indicated by hidden lines 3021A in FIG. 32) to the deployed position shown in FIG. 32.

After the indicator flag 3021 reaches the deployed position, the ones counter wheel 2918A and tens counter wheel 2918B can continue to rotate and increment in the manner described above responsive to exposure of the instrument to reprocessing cycles. The sector gear 2933 of the second lobed wheel 2925B is disengaged from the teeth 2935 of the indicator flag 3021, and the indicator flag 3021 remains in the deployed position shown in the drawings regardless of the further movement of the ones counter wheel 2918A or tens counter wheel 2918B. Thus, the device 2914 continues to mechanically record reprocessing cycles to which it may be exposed while providing a clear indication to the user that the permissible number of reprocessing cycles has been met.

Embodiments of the present disclosure provide reliable and robust devices that record the number of times an instrument is subjected to reprocessing cycles and are easily viewable by a user handling the instrument, and/or readable by systems to which the instrument may be connected.

In some embodiments, instruments according to the present disclosure can include multiple kinds of recording and indicator devices, such as both environment exposure recording and use recording devices as disclosed above in connection with the embodiments of FIGS. 16-32 herein. Accordingly, some instruments according to the present disclosure can include both a use recording device, such as any of the various embodiments of use counters disclosed herein, and a reprocessing recording device for recording occurrence of a change in environmental conditions to which the instrument is subjected, such as conditions associated with a reprocessing procedure, according to the various embodiments disclosed herein. As discussed herein, such devices can include one or more state-change elements, such as, but not limited to, temperature-responsive elements, pressure-responsive elements, or vibration-responsive elements, that undergo a change of state in response to a change in an environmental condition.

The state-change element(s) can be operably coupled with a counter mechanism that records the occurrence of an event associated with a predetermined change in conditions to which the state-change element is responsive to cause it to change state. As a non-limiting example, the event may be one associated with a reprocessing procedure. The counter mechanism and the state-change element can be operably coupled such that as the instrument comprising the recording device undergoes a reprocessing procedure, the counter mechanism increments to reflect the occurrence that the instrument was subjected to such reprocessing procedure. For example, the counter mechanism can be incrementally movable in response to each change in state of the state-change element from the first state to the second state. That is, the counter mechanism can record a number of transitions of the state-change element from the first state to the second state. The counter mechanism is a form of user-accessible storage device that records and provides information to the user regarding the number of changes of an environmental condition, such as that associated with a reprocessing procedure.

Figure 33:
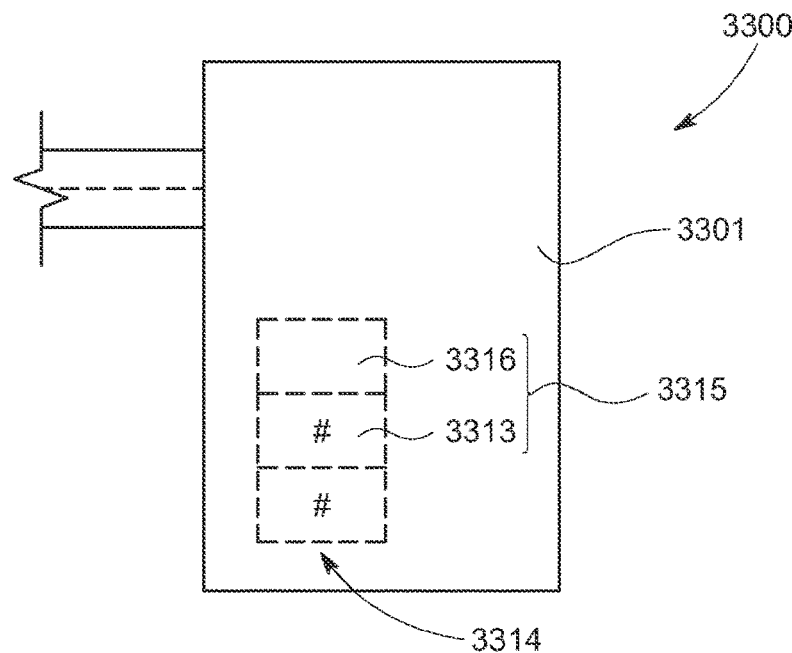
FIG. 33 is a schematic side view of a portion of an instrument according to an exemplary embodiment of the disclosure comprising a device for recording use of the instrument and a device for recording reprocessing procedures to which the instrument has been subjected.

FIG. 33 shows a schematic view of an instrument 3300 according to the present disclosure including both a use recording device 3314 and a device 3315 for recording reprocessing procedures (or other changes in environmental conditions). As shown in FIG. 33, the instrument 3300 includes the use recording device 3314 and the reprocessing recording device 3315 adjacent to one another on a side exterior of the housing 3301 of the instrument 3300. Alternatively, in other embodiments, the use recording device 3314 and the reprocessing recording device 3315 can be positioned in different locations on the same side of the instrument, or on different sides of the housing 3301 of the instrument 3300. The reprocessing recording device 3315 comprises a state-change element 3316 operably coupled to a counter mechanism 3313, which includes indicia displaying information related to the number of times the instrument has been subjected to a reprocessing procedure or other change in environmental conditions.

Figure 34:
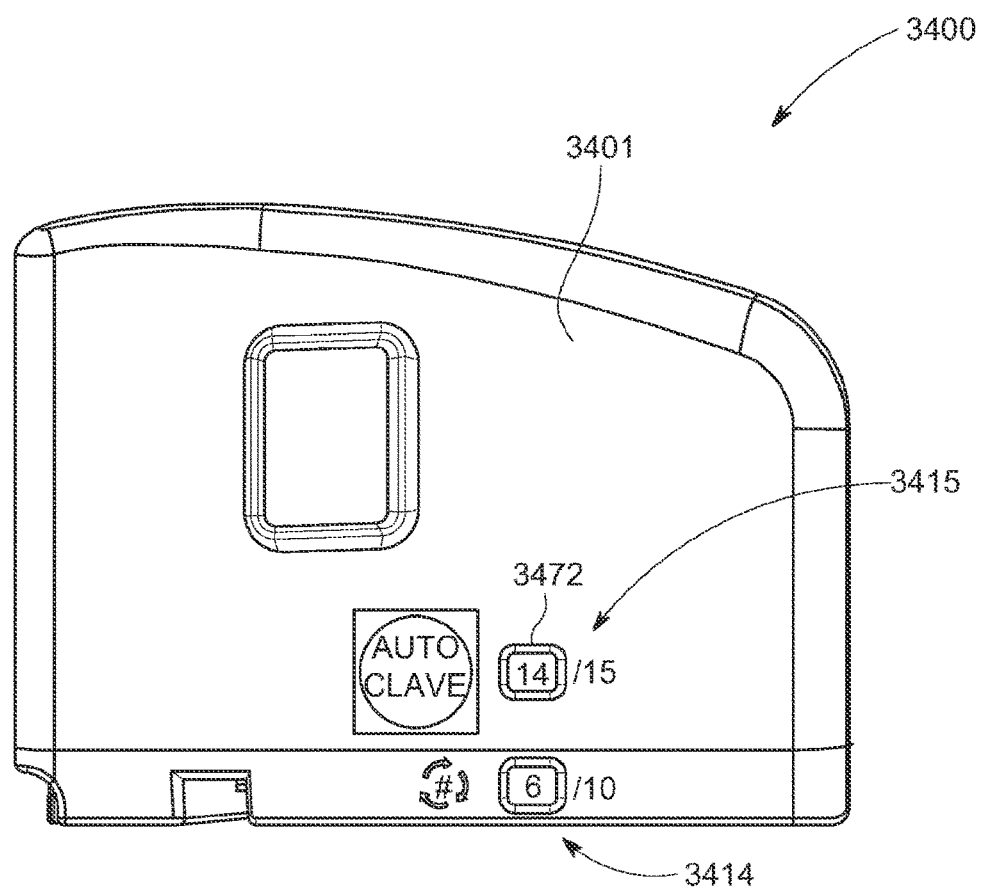
FIG. 34 is a side view of a portion of an instrument according to an exemplary embodiment of the disclosure comprising a device for recording use of the instrument and a device for recording reprocessing procedures to which the instrument has been subjected.

Referring now to FIG. 34, another exemplary embodiment of an instrument 3400 including both a use recording device 3414 and a reprocessing recording device 3415 is shown. In FIG. 34, only the respective indicator portions of the use recording device 3414 and reprocessing recording device 3415 are shown, the other components of the devices being obscured by a housing of the instrument 3400. As discussed above in connection with the various embodiments of use recording devices disclosed herein, the use recording device 3414 includes indicia to indicate to the user a number of remaining uses available for the instrument. The reprocessing recording device 3415 includes indicia that indicates to the user a remaining number of reprocessing procedures to which the instrument 3400 can be exposed. While the use recording device 3414 and reprocessing recording device 3415 both include indicia comprising consecutive numerical indicators that count down from a maximum number of available uses or reprocessing procedures, respectively, to which the instrument 3400 can be subjected, other indicia and indicator schemes are possible, as discussed in detail above. For example, indicator schemes including tapered graphs, bar graphs, color-based indicators, text indicators, or any other type of indicator are within the scope of the disclosure. Further, the indicia used for the use recording device and the reprocessing recording device can be similar, as in the instrument 3400, or can be dissimilar. That is, one of the use recording device 3414 and the reprocessing recording device 3415 can feature one indicator scheme, such as the consecutive numbering scheme shown in FIG. 34, while the other of the use recording device 3414 and the reprocessing recording device 3415 can feature another indicator scheme, such as a graphical indicator, color indicator, etc., as discussed above. Alternatively, both the use recording device 3414 and the reprocessing recording device 3415 could use non-numerical indicators as discussed herein, such as graphical indicators, color-based indicators, or other indicator schemes as disclosed herein in any desired combination.

The reprocessing recording device 3415 can include, without limitation, state-change elements including temperature-responsive elements, pressure-responsive elements, or vibration-responsive elements that are operable to change a state in response to temperature thresholds being reached. These changes of state can then be used to convert motion or actuation of other elements in order to provide a counter mechanism that advances as the instrument is subjected to the predefined temperature thresholds, triggering a reprocessing or other "use" of the instrument associated with a preset environmental condition or set of conditions to which the instrument is subjected. Such state-change elements can be or include shape-memory alloy components, material reservoirs such as wax motors, pressure-sensitive diaphragms, or other components. The use recording device 3414 can be or include the rotatable disc 218 as discussed in connection with FIGS. 2-4 herein. Due to the potentially small overall size and low component count of use recording devices employing the rotatable disc 218, such a use recording device can be relatively easily packaged in combination with the various reprocessing recording devices disclosed herein. However, any of the various embodiments of use recording devices disclosed herein can be used in combination with any of the reprocessing recording devices disclosed herein.

Figure 35:
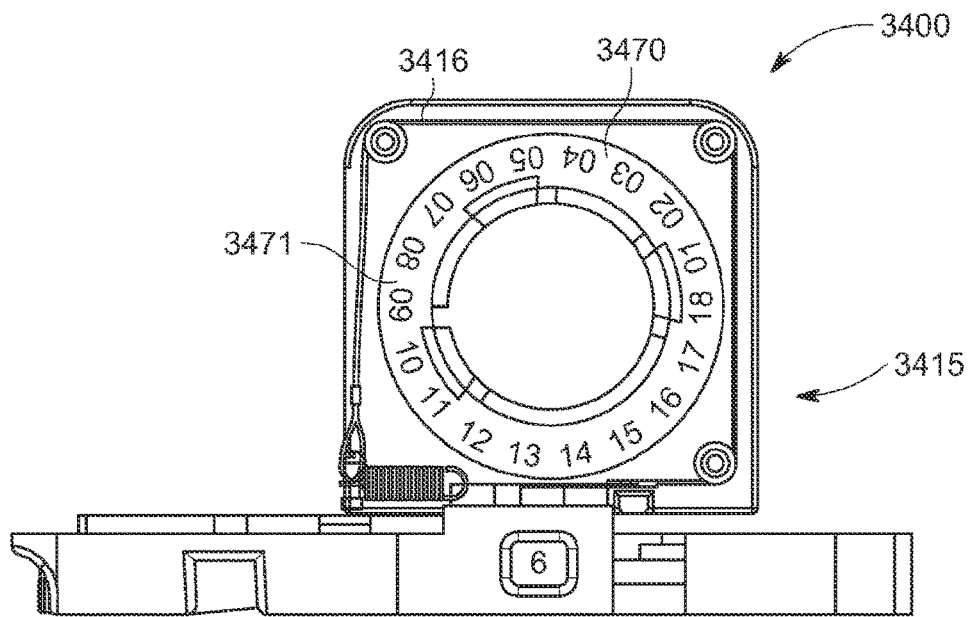
FIG. 35 is a side view of the portion of the instrument of FIG. 34 with the housing omitted.

Referring now to FIG. 35, an interior view of the instrument 3400 is shown with the housing 3401 (FIG. 34) omitted to reveal the internal components of the instrument 3400. In the embodiment shown, the reprocessing recording device 3415 includes a state-change element 3416 that comprises a shape memory alloy wire operably coupled to an indicator wheel 3470 with visual indicia 3471 in the form of consecutive numbers displayed individually through an aperture 3472 (FIG. 34) in the housing 3401 (FIG. 34) of the instrument 3400. The state-change element 3416 can be operably coupled to the indicator wheel 3470 by mechanical components as discussed herein, such as a ratcheting system that advances the indicator wheel by a specified amount upon exposure of the instrument to a reprocessing procedure (e.g., to advance the indicator wheel 3470 to subsequently display lower numbers of remaining reprocessing cycles to which the instrument can be exposed).

The temperature-responsive element can be or include materials that change in physical configuration, such as one or more of a physical dimension (e.g., length, width, height, shape, and/or volume, etc.), or another change in state (e.g., position, rigidity, electrical charge, color, and/or phase) in response to exposure to a temperature above (or below) a specified threshold temperature. The threshold temperature can be defined by the conditions of a reprocessing procedure to which the instrument will be subjected. For example, the threshold temperature can be chosen to be greater than temperatures to which the instrument will be subjected during normal use and below a maximum temperature to which the instrument will be subjected during reprocessing. For example, an autoclave procedure may involve temperatures at or above 120° C. for a specified period of time, while a washing (e.g., ultrasonic washing) process may include temperatures elevated beyond normal ambient (e.g., room) temperatures but below autoclaving temperatures, or even below 100° C. The threshold temperature of the temperature-responsive element can be chosen such that the recording device only records an autoclave procedure, such as by choosing a threshold temperature above, e.g., 100° C., or to record both washing at elevated temperatures and autoclaving, such as by choosing a threshold temperature above the temperature used for washing, (such as a temperature in a range of, for example, from 70° C. to 90° C., depending on the temperature used during the washing process). Those having ordinary skill in the art will appreciate how to design and configure devices according to the present disclosure to respond to more than one type of temperature excursion if desired, such as to record differing types of reprocessing procedures with differing temperature characteristics using differing temperature-responsive, state-change elements.

Figure 36:
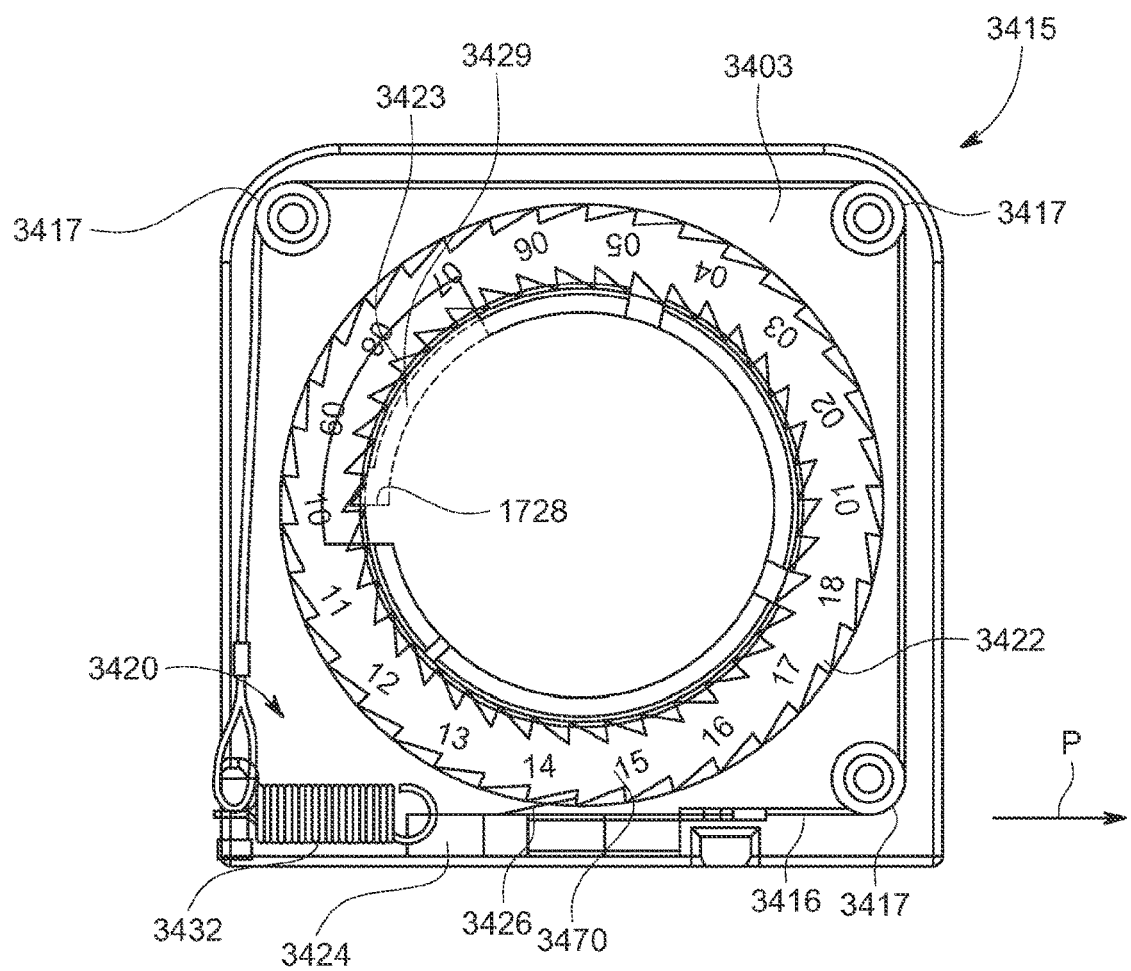
FIG. 36 is an enlarged side view of the device for recording reprocessing procedures of the instrument of FIG. 34.

FIG. 36 is an enlarged view of the reprocessing recording device 3415 shown in FIG. 35. In the exemplary device of FIGS. 35 and 36, the state-change element 3416 is a wire, cable, or other similar member, made from a shape memory metal, such as nickel-titanium alloy (e.g., nitinol). The state-change element 3416 is routed by a series of pulleys 3417. Other embodiments can include other temperature-responsive elements, including but not limited to, wax motors, bimetallic components, temperature-sensitive electronic switches, or other components. These temperature-responsive elements can be configured to undergo a change in state upon a change in temperature, such as heating to at least a threshold temperature. The state-change element 3416 is operably coupled with a counter mechanism such that the counter mechanism records a change of state of the shape-memory wire state-change element 3416 resulting from exposure to temperatures elevated above the specified threshold temperature.

The counter mechanism is configured to incrementally move based on a change of state of the state-change element 3416. For example, in the embodiment of FIGS. 35 and 36, the counter mechanism comprises a ratchet mechanism 3420. The ratchet mechanism 3420 comprises the indicator wheel 3470, which includes ratchet teeth 3422 that engage with one or more drive pawls 3426 mounted to a drive pawl carrier 3424. The indicator wheel 3470, through engagement of the ratchet teeth 3422 with the drive pawls 3426 and operation of the drive pawl carrier 3424, moves incrementally for each temperature excursion above the specified threshold temperature. As discussed in greater detail below, the ratchet mechanism 3420 can include or be operably coupled with a user-accessible storage mechanism, such as the exemplary indicator wheel 3470, or other user-accessible storage mechanisms as discussed herein.

The drive pawl carrier 3424 is movable in translation in direction P shown in FIG. 36. The drive pawl carrier 3424 carries at least one drive pawl 3426, but such configuration is not limiting and other numbers and arrangements of drive pawls would be apparent to those having ordinary skill in the art. An end portion of the state-change element 3416 is fixed to the drive pawl carrier 3424 in any appropriate manner. For example, in the embodiment of FIG. 36, an end portion of the state-change element 3416 is crimped to form a loop and the loop is secured to the drive pawl carrier 3424.

The ratchet mechanism 3420 can include features configured to prevent back-driving of the ratchet mechanism 3420. For example, the ratchet mechanism 3420 can include a locking pawl 3428 configured to engage with anti-backup ratchet teeth 3423. The locking pawl 3428 allows movement of the indicator wheel 3470 in the drive direction but prevents the indicator wheel 3470 from rotating in a direction opposite the drive direction once advanced (e.g., the locking pawl 3428 permits movement of the ratchet wheel in the counterclockwise direction as shown in FIGS. 35 and 36 and prevents the indicator wheel 3470 from rotating clockwise). While in the embodiment of FIGS. 35 and 36, the locking pawl 3428 engages with anti-backup ratchet teeth 3423, in other exemplary embodiments the locking pawl 3428 can be configured to engage with ratchet teeth 3422. That is, in some designs, both the drive pawls 3426 and locking pawl 3428 can engage the same set of ratchet teeth, as will be apparent to one of ordinary skill in the art.

The locking pawl 3428 can be coupled to (e.g., integrated with) a flexure arm 3429. In FIG. 36, the flexure arm 3429 is shown in hidden lines. Elastic deformation of the flexure arm 3429 permits rotation of the indicator wheel 3470 in the drive direction as the anti-backup ratchet teeth 3423 deflect the locking pawl 3428 away from the indicator wheel 3470. As would be readily understood, the flexure arm 3429 could alternatively be hinged, and one or more biasing members, such as springs, provided to ensure the locking pawl 3428 returns to an un-deflected position in engagement with the anti-backup ratchet teeth 3423 to prevent back-driving of the indicator wheel 3470.

The drive pawl carrier 3424 is biased to an initial position (e.g., the position shown in FIG. 36). A biasing element in the form of an extension spring 3432 is coupled to the drive pawl carrier 3424 to bias the drive pawl carrier 3424 in the position shown in FIG. 36. The extension spring 3432 is fixed to the base 3403 of the reprocessing recording device 3415 at one end and to the drive pawl carrier 3424 at an opposite end. The extension spring 3432 generally extends and retracts along the direction the state-change element 3416 extends and contracts.

Operation of the counter mechanism 3413 is effected by the state-change element 3416's exposure to temperature excursions. For example, the state-change element 3416 reduces in length when heated to or above the specified threshold temperature, due to a transition from martensitic state to austenitic state of the nitinol material. As the state-change element 3416 shortens, tension generated in the state-change element 3416 acts against the biasing force of the extension spring 3432, extending the extension spring 3432 and causing the drive pawl carrier 3424 to translate in direction P. The drive pawls 3426 engage the ratchet teeth 3422 of the indicator wheel 3470 and rotate the indicator wheel 3470 in the counterclockwise direction, as viewed in FIG. 36.

As the indicator wheel 3470 rotates counterclockwise due to engagement of the drive pawl 3426 with the ratchet teeth 3422, the locking pawl 3428 rides over one or more of the anti-backup ratchet teeth 3423 as the indicator wheel 3470 assumes a new position of a plurality of unique positions. Each position is provided with indicia associated with a change in environmental condition such as associated with a reprocessing cycle. Once the indicator wheel 3470 assumes the new position, the locking pawl 3428 prevents counter-rotation (e.g., in the clockwise position as described above) of the indicator wheel 3470. As will be apparent to one of ordinary skill in the art, the described ratcheting functionality of the drive pawl 3426 and locking pawl 3428 in conjunction with the ratchet teeth 3422 and anti-backup ratchet teeth 3423 can be obtained by the profile of the respective teeth, the orientation and shape of the pawls, and other factors of which those having ordinary skill in the art would readily appreciate.

Upon cooling from the elevated temperature to resume its martensitic state, the state-change element 3416 lengthens, removing the force exerted against the biasing force of the extension spring 3432 and allowing the extension spring 3432 to retract and return the drive pawl carrier 3424 in a direction opposite the direction P. The indicator wheel 3470 remains in the new rotated position due to engagement of the locking pawl 3428 with the ratchet teeth 3422.

Rotational advancement of the indicator wheel 3470 can correspond to a change in the indicated number of reprocessing cycles available for the instrument to be subjected to (or the number of indicated reprocessing cycles the instrument has undergone), as advancement of the indicator wheel 3470 results in a different indicium being shown through the aperture 3472 (FIG. 34).

In the embodiment of FIGS. 35 and 36, the state-change element 3416 is a wire made from a shape memory metal, such as nickel-titanium alloy (e.g., nitinol). Other embodiments can include other temperature-responsive elements, including but not limited to, wax motors, bimetallic components, temperature-sensitive electronic switches, bladders or other reservoirs containing substances that undergo phase changes, dimension changes, position changes, volume changes, or other changes in response to temperature changes, or other components. These temperature-responsive elements can be configured to undergo a change in state upon heating to the specified threshold temperature.

Figure 37:
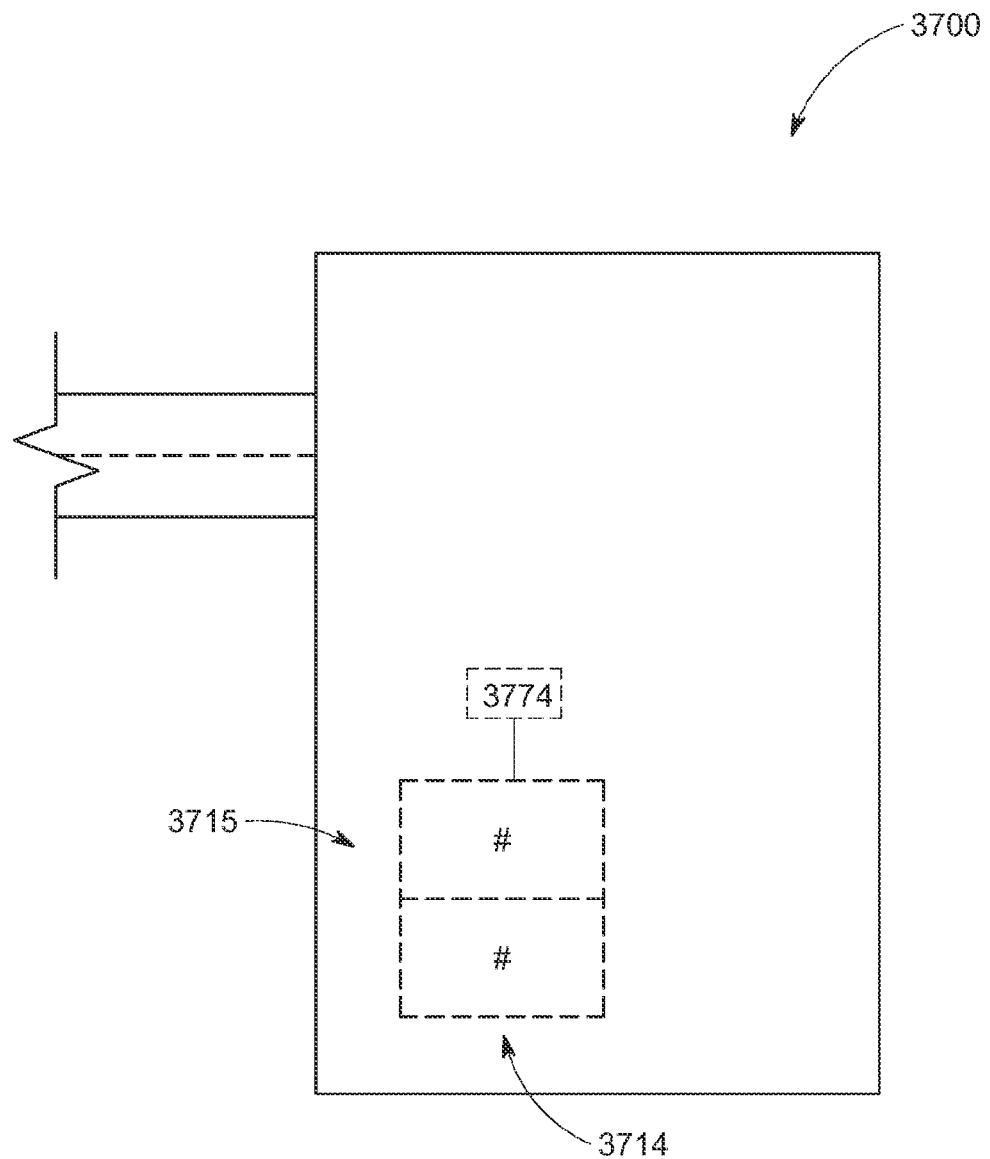
FIG. 37 is a schematic side view of a portion of an instrument according to another exemplary embodiment of the disclosure comprising a device for recording use of the instrument and a device for recording reprocessing procedures to which the instrument has been subjected.

For example, referring now to FIG. 37, an exterior schematic view of another instrument 3700 according to yet another exemplary embodiment of the present disclosure is shown, with components of the instrument represented schematically by dashed lines. The instrument 3700 comprises a reprocessing recording device 3715 that includes a reservoir 3774 containing a state-change material (such as a wax motor) operably coupled to a user-accessible storage device such as an indicator wheel (not shown), which may be generally similar to indicator wheel 3470 discussed in connection with FIGS. 35 and 36. The reservoir 3474 can be a wax motor or other reservoir that actuates movement of the indicator wheel upon exposure of the instrument 3700 to a predetermined temperature threshold, such as associated with a reprocessing procedure, as discussed herein.

Embodiments described herein may be used, for example, with remotely operated, computer-assisted systems (such, for example, teleoperated surgical systems) such as those described in, for example, U.S. Pat. No. 9,358,074 (filed May 31, 2013) to Schena et al., entitled "Multi-Port Surgical Robotic System Architecture", U.S. Pat. No. 9,295,524 (filed May 31, 2013) to Schena et al., entitled "Redundant Axis and Degree of Freedom for Hardware-Constrained Remote Center Robotic Manipulator", and U.S. Pat. No. 8,852,208 (filed Aug. 12, 2010) to Gomez et al., entitled "Surgical System Instrument Mounting", each of which is hereby incorporated by reference in its entirety. Further, embodiments described herein may be used, for example, with a da Vinci® Surgical System, such as the da Vinci Si® Surgical System, da Vinci X® Surgical System, the da Vinci Xi® Surgical System, all with or without Single-Site® single orifice surgery technology, or the daVinci SP® Surgical System, all commercialized by Intuitive Surgical, Inc., of Sunnyvale, California The embodiments described herein are not limited to the surgical systems noted above, and various other teleoperated, computer-assisted surgical system configurations may be used with the embodiments described herein. Further, although various embodiments described herein are discussed in connection with a manipulating system of a teleoperated surgical system, the present disclosure is not limited to use with a teleoperated surgical system. Various embodiments described herein can optionally be used in conjunction with hand-held, manual instruments.

As discussed above, in accordance with various embodiments, surgical instruments of the present disclosure are configured for use in teleoperated, computer-assisted surgical systems employing robotic technology (sometimes referred to as robotic surgical systems). Referring now to FIG. 13, an embodiment of a manipulator system 1300 of a computer-assisted surgical system, to which surgical instruments are configured to be mounted for use, is shown. Such a surgical system may further include a user control system, such as a surgeon console (not shown) for receiving input from a user to control instruments coupled to the manipulator system 1300, as well as an auxiliary system, such as auxiliary systems associated with the da Vinci® systems noted above.

As shown in the embodiment of FIG. 13, a manipulator system 1300 includes a base 1320, a main column 1340, and a main boom 1360 connected to main column 1340. Manipulator system 1300 also includes a plurality of manipulator arms 1310, 1311, 1312, 1313, which are each connected to main boom 1360. Manipulator arms 1310, 1311, 1312, 1313 each include an instrument mount portion 1322 to which an instrument 1330 may be mounted, which is illustrated as being attached to manipulator arm 1310.

Instrument mount portion 1322 comprises a drive assembly 1323 to which a transmission mechanism 1334 (which may generally correspond to the transmission mechanism 110 discussed in connection with FIG. 1) of the instrument 1330 connecting with the drive assembly 1323, according to an embodiment. Drive assembly 1323 contains a variety of drive and other mechanisms that are controlled to respond to input commands at the surgeon console and transmit forces to the transmission mechanism 1334 to actuate the instrument 1330. Although the embodiment of FIG. 13 shows an instrument 1330 attached to only manipulator arm 1310 for ease of viewing, an instrument may be attached to any and each of manipulator arms 1310, 1311, 1312, 1313.

Other configurations of surgical systems, such as surgical systems configured for single-port surgery, are also contemplated. For example, with reference now to FIG. 14, a portion of an embodiment of a manipulator arm 2140 of a manipulator system with two surgical instruments 2300, 2310 in an installed position is shown. The surgical instruments 2300, 2310 can generally correspond to instruments discussed above, such as instrument 100 disclosed in connection with FIG. 1. For example, the embodiments described herein may be used with a da Vinci SP® Surgical System, commercialized by Intuitive Surgical, Inc. of Sunnyvale, California. The schematic illustration of FIG. 14 depicts only two surgical instruments for simplicity, but more than two surgical instruments may be mounted in an installed position at a manipulator system as those having ordinary skill in the art are familiar with. Each surgical instrument 2300, 2310 includes a shaft 2320, 2330 that at a distal end has a moveable end effector or an endoscope, camera, or other sensing device, and may or may not include a wrist mechanism (not shown) to control the movement of the distal end.

Transmission mechanisms 2385, 2390 (which may generally correspond to transmission mechanism 110 disclosed in connection with FIG. 1) are disposed at a proximal end of each shaft 2320, 2330 and connect through a sterile adaptor 2400, 2410 with drive assemblies 2420, 2430. Drive assemblies 2420, 2430 contain a variety of internal mechanisms (not shown) that are controlled by a controller (e.g., at a control cart of a surgical system) to respond to input commands at a surgeon side console of a surgical system to transmit forces to the transmission mechanisms 2385, 2390 to actuate surgical instruments 2300, 2310.

The embodiments described herein are not limited to the embodiments of FIG. 13 and FIG. 14, and various other teleoperated, computer-assisted surgical system configurations may be used with the embodiments described herein.

This description and the accompanying drawings that illustrate various embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. An instrument, comprising:
a shaft comprising a proximal end portion and a distal end portion;
an end effector at the distal end portion of the shaft;
a transmission mechanism at the proximal end portion of the shaft, the transmission mechanism comprising:
a driven input device engageable with an external drive mechanism, and
an indicator operably coupled to the driven input device and moveable through each of a plurality of consecutive positions,
wherein each of the plurality of consecutive positions is associated with a unique indicia of a non-zero number of available uses left of the instrument, and
wherein in response to the driven input device being driven by the external drive mechanism, the indicator moves from a current position of the plurality of positions to a subsequent position of the plurality of positions; and
a device configured to record occurrence of a change in an environmental condition to which the instrument is subjected.

2. The instrument of claim 1, wherein the subsequent position is associated with indicia indicating a fewer number of available uses than indicia associated with the current position.

3. The instrument of claim 2, wherein the subsequent position indicates one fewer available uses than the current position.

4. The instrument of claim 1, wherein the driven input device comprises a rotatable disc.

5. The instrument of claim 4, wherein the indicator comprises visual indicia on the rotatable disc, wherein the visual indicia are on a lateral sidewall or a planar face of the disc.

6. The instrument of claim 5, wherein the visual indicia comprise a series of integer numbers.

7. The instrument of claim 6, wherein the series comprises a series of consecutive integer numbers.

8. The instrument of claim 6, wherein the series comprises a series of non-consecutive integer numbers.

9. The instrument of claim 5, wherein the visual indicia comprise a graph indicator.

10. The instrument of claim 5, wherein:
the instrument comprises a housing in which the transmission mechanism is located;
the housing comprises an aperture; and
the visual indicia are visible through the aperture.

11. The instrument of claim 1, wherein the driven input device comprises a locking mechanism configured to maintain the indicator in a given position of the plurality of consecutive positions on the condition the driven input device is not driven by the external drive mechanism.

12. The instrument of claim 11, wherein:
the instrument comprises a housing in which the transmission mechanism is located, the housing comprising a plurality of notches, and
the locking mechanism comprises a plurality of flexural members engageable with the notches.

13. The instrument of claim 12, wherein the flexural members further comprise cam surfaces engageable with the external drive mechanism to deflect the plurality of flexural members into a disengaged state with the notches in the housing.

14. The instrument of claim 1, further comprising a state-change element transitionable between a first state and a second state in response to a predetermined change in the environmental condition.

15. The instrument of claim 14, further comprising a counter mechanism operably coupled to the state-change element, the counter mechanism being incrementally movable in response to transition of the state-change element from the first state to the second state.

16. The instrument of claim 1, wherein the device further comprises a user-accessible storage device configured to store and provide information regarding a number of changes in environmental conditions to which the instrument has been subjected.

17. A medical device comprising:
a first indicator moveable through a first plurality of positions; and
a second indicator movable through a second plurality of positions;
wherein each position of the first plurality of positions is associated with a unique indicia of a number of available uses remaining on the medical device; and
wherein each position of the second plurality of positions is associated with an occurrence of a change in an environmental condition to which the medical device is subjected.

18. The medical device of claim 17, wherein the change in the environmental condition is a change in temperature during an autoclave cycle.

19. A device for recording occurrence of a change in an environmental condition to which a medical instrument is subjected, the device comprising:
a state-change element transitionable between a first state and a second state in response to a predetermined change in the environmental condition;
a counter mechanism operably coupled to the state-change element, the counter mechanism being incrementally movable in response to transition of the state-change element from the first state to the second state; and
a user-accessible storage device operably coupled to the counter mechanism, the user-accessible storage device being configured to store and provide information representing a number of transitions of the state-change element.

20. The device of claim 19, wherein the state-change element comprises a temperature-responsive element.

* * * * *